US010858381B2

(12) United States Patent
Cui et al.

(10) Patent No.: US 10,858,381 B2
(45) Date of Patent: Dec. 8, 2020

(54) ANTIOXIDANT COMPOUNDS AND THEIR USE

(71) Applicant: University of Pittsburgh—Of the Commonwealth System of Higher Education, Pittsburgh, PA (US)

(72) Inventors: Xinyan Cui, Wexford, PA (US); Noah Snyder, Glenshaw, PA (US); Kasey Catt, Pittsburgh, PA (US); James Eles, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/513,064

(22) Filed: Jul. 16, 2019

(65) Prior Publication Data

US 2019/0337972 A1    Nov. 7, 2019

Related U.S. Application Data

(62) Division of application No. 15/239,473, filed on Aug. 17, 2016, now Pat. No. 10,385,082.

(60) Provisional application No. 62/206,748, filed on Aug. 18, 2015.

(51) Int. Cl.
| | |
|---|---|
| *C07F 13/00* | (2006.01) |
| *A61L 27/34* | (2006.01) |
| *A61L 27/54* | (2006.01) |
| *A61L 31/10* | (2006.01) |
| *A61L 31/16* | (2006.01) |
| *C07D 487/22* | (2006.01) |
| *C07F 3/02* | (2006.01) |
| *C07F 15/02* | (2006.01) |
| *A61L 27/28* | (2006.01) |
| *A61B 5/04* | (2006.01) |
| *A61B 17/68* | (2006.01) |
| *A61C 8/00* | (2006.01) |
| *A61F 2/24* | (2006.01) |
| *A61F 2/82* | (2013.01) |
| *A61L 26/00* | (2006.01) |
| *A61L 27/52* | (2006.01) |
| *A61M 25/00* | (2006.01) |
| *A61N 1/36* | (2006.01) |
| *C08K 5/3432* | (2006.01) |
| *C09D 5/16* | (2006.01) |
| *A61N 1/362* | (2006.01) |
| *A61B 17/00* | (2006.01) |

(52) U.S. Cl.
CPC ........ *C07F 13/005* (2013.01); *A61B 5/04001* (2013.01); *A61B 17/68* (2013.01); *A61C 8/0013* (2013.01); *A61F 2/24* (2013.01); *A61F 2/82* (2013.01); *A61L 26/008* (2013.01); *A61L 27/28* (2013.01); *A61L 27/34* (2013.01); *A61L 27/52* (2013.01); *A61L 27/54* (2013.01); *A61L 31/10* (2013.01); *A61L 31/16* (2013.01); *A61M 25/0017* (2013.01); *A61N 1/3605* (2013.01); *C07D 487/22* (2013.01); *C07F 3/02* (2013.01); *C07F 15/025* (2013.01); *C08K 5/3432* (2013.01); *C09D 5/1625* (2013.01); *A61B 2017/00889* (2013.01); *A61B 2017/00893* (2013.01); *A61F 2250/0067* (2013.01); *A61L 2300/404* (2013.01); *A61M 2205/0205* (2013.01); *A61N 1/3629* (2017.08)

(58) Field of Classification Search
CPC ........... C08L 77/00; C07D 487/22; C07F 3/02
See application file for complete search history.

(56) References Cited

U.S. PATENT DOCUMENTS

| | | | |
|---|---|---|---|
| 5,826,369 A | 10/1998 | Jordan | |
| 8,183,364 B2 | 5/2012 | Batinic-Haberle et al. | |
| 8,355,802 B2 | 1/2013 | Keitel et al. | |
| 8,946,202 B2 | 2/2015 | Crapo et al. | |
| 9,416,282 B2 | 8/2016 | Wilker et al. | |
| 2008/0199506 A1 | 8/2008 | Horres et al. | |
| 2013/0034671 A1 | 2/2013 | George et al. | |
| 2014/0080797 A1 | 3/2014 | Batinic-Haberle et al. | |

FOREIGN PATENT DOCUMENTS

| | | | |
|---|---|---|---|
| DE | 102005021622 | 11/2006 | |
| WO | WO 2005/114720 | 12/2005 | |
| WO | WO 2015/034777 | 3/2015 | |
| WO | WO-2015034777 A1 * | 3/2015 | ............... A61K 8/58 |

OTHER PUBLICATIONS

Asayama, S. et al. "Chemical modification of manganese porphyrins with biomolecules for new functional antioxidants" J. Biomater. Sci. Polymer Edn, vol. 14, No. 11, pp. 1169-1179 (2003) (Year: 2003).*

Meyer-Roscher, B. et al. "Tetraphenylporphyrins as Coupling Reagents and Corrosion Inhibitors" Adv. Mater. 1992, 4 (7/8), pp. 496-498 (Year: 1992).*

(Continued)

*Primary Examiner* — Andrew S Rosenthal

(74) *Attorney, Agent, or Firm* — Klarquist Sparkman, LLP

(57) ABSTRACT

Disclosed herein are novel amine-functionalized porphyrin compounds, as wells as pharmaceutically acceptable salts or esters thereof. The disclosed compounds can be used to impart antioxidant, anti-inflammatory, anti-microbial, and/or cell-adhesion specificity to a surface or material in need thereof, such as a surface of an indwelling medical implant, or a marine surface.

7 Claims, 15 Drawing Sheets

(56) References Cited

OTHER PUBLICATIONS

Asayama et al., "Chemical modification of manganese porphyrins with biomolecules for new functional antioxidants," *J. Biomater. Sci. Polymer Edn.*, 2003, 14(11), pp. 1169-1179.

Azemi et al., "Surface immobilization of neural adhesion molecule L1 for improving the biocompatibility of chronic neural probes: In vitro characterization," *Acta Biomater*, Sep. 2008, 4(4), pp. 1208-1217.

Chang et al., "Cell and protein compatibility of parylene-C surfaces," *Langmuir*, Nov. 6, 2007, 23(23), pp. 11718-11725.

Dental Implants, downloaded from http://www.knoxterracedental.com.au/dental-services/dental-implants/single-tooth-implant, Dec. 8, 2014, pp. 1-3.

International Search Report, dated Nov. 9, 2016, mailed by the ISA in International Application No. PCT/US2016/047290, 6 pp.

Kiselev, BA and Kozlov, YN, "Photoelectrochemistry of chlorophyll monolayers," *Journal of Electroanalytical Chemistry and Interfacial Electrochemistry*, 1980, 116, p. 247-254.

Lewicki, "A review of methods for spike sorting: the detection and classification of neural action potentials," *Network: Comput. Neural Syst.*, 9, 1998, R53-R78, 26 pp.

Luo et al., "Pure graphene oxide doped conducting polymer nanocomposite for bio-interfacing," *J. Mater. Chem. B*, 2013, 1(1), pp. 1340-1348.

Miriyala et al., "Manganese superoxide dismutase, MnSOD and its mimics," *Biochim. Biophys. Acta*, May 2012, 1822(5), pp. 794-814.

Potter-Baker et al., "Development of superoxide dismutase mimetic surfaces to reduce accumulation of reactive oxygen species for neural interfacing applications," *J. Mater. Chem. B. Mater. Biol. Med.*, Apr. 28, 2014, 2(16): pp. 2248-2258.

Rogers et al., "Tandem dispersion and killing of bacteria from a biofilm," *Org. Biomol. Chem.*, 2009, 7, pp. 603-606.

Sia et al., "Microfluidic devices fabricated in poly-dimethylsiloxane) for biological studies," *Electrophoresis*, Nov. 2003, 24(21), pp. 3563-3576.

Snyder et al., "Antioxidant Effects of a SOD mimic Functionalized on Neural Implants Surfaces," Abstract and Poster Presentation 893.10/OO17, Oct. 17, 2012, Society for Neuroscience Annual Meeting, New Orleans, LA.

What is a Dental Post? downloaded from http://drstonedds.com/what-is-a-dental-post, Aug. 19, 2013, pp. 1-3.

Written Opinion of the International Searching Authority, dated Nov. 9, 2016, mailed by the ISA in International Application No. PCT/US2016/047290, 10 pp.

Zhang et al., "Chemical surface modification of parylene C for enhanced protein immobilization and cell proliferation," *Acta Biomater.*, 2011, 7(10), pp. 3746-3756.

\* cited by examiner

FIG. 14A
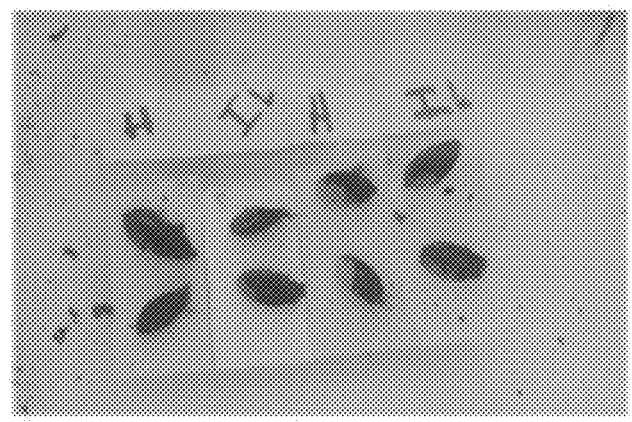
0 hrs
24 hrs
24 hrs

FIG. 14B
Algae accumulation after 1 month
incubation in freshwater tank
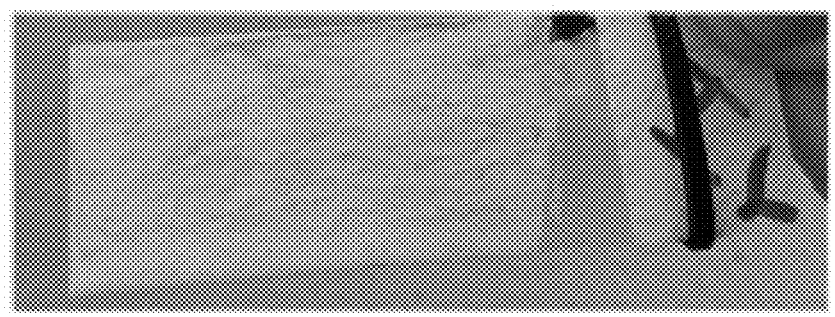
Marine Epoxy coating
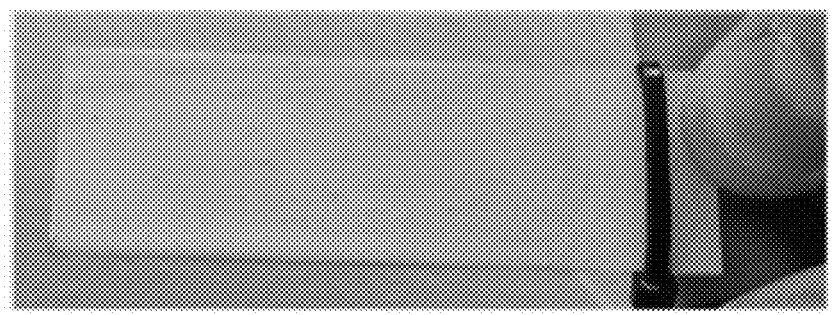
Marine Exopy + 1% w/v iSODm coating

ANTIOXIDANT COMPOUNDS AND THEIR USE

CROSS REFERENCE TO RELATED APPLICATIONS

This application is a divisional of U.S. application Ser. No. 15/239,473, filed Aug. 17, 2016, issued as U.S. Pat. No. 10,385,082 on Aug. 20, 2019, which claims priority to U.S. Provisional Application No. 62/206,748, filed Aug. 18, 2015. The above-listed applications are herein incorporated by reference in their entirety.

ACKNOWLEDGMENT OF GOVERNMENT SUPPORT

This invention was made with government support under Grant No. NS062019, awarded by the National Institutes of Health. The government has certain rights in the invention.

FIELD

The present disclosure relates to antioxidant compounds and the use thereof. In some embodiments, the antioxidant compounds can be used in a coating on a medical implant to reduce oxidation and/or inflammation of tissue in a subject, or as a coating on industrial surfaces to reduce biofouling.

BACKGROUND

Cationic porphyrins that mimic the structure of endogenous superoxide dismutase (SOD) proteins are known to have antioxidant properties. However, incorporation of such compounds into medical and industrial surfaces and materials where antioxidant activity is desired has been difficult.

SUMMARY

Disclosed herein are novel amine-functionalized porphyrin compounds, as well as pharmaceutically acceptable salts or esters thereof. The disclosed compounds can be used to impart antioxidant, anti-inflammatory, and/or anti-microbial properties to a surface or material in need thereof, such as a surface of an indwelling medical device, or a marine surface. Accordingly, in some embodiments, materials and surfaces coated with one or more of the disclosed amine-functionalized porphyrin compounds can provide a reduction in biofouling, a reduction in biofilm accumulation, and/or a reduction in oxidative corrosion compared to uncoated surfaces and materials.

In some embodiments the amine-functionalized porphyrin compound is a compound or salt or ester thereof comprising a structure as set forth as one of:

Formula I

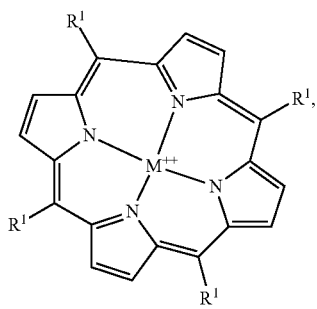

Formula II

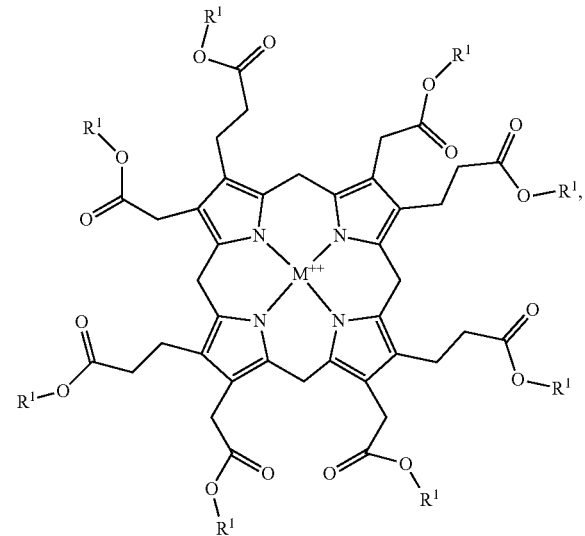

Formula III

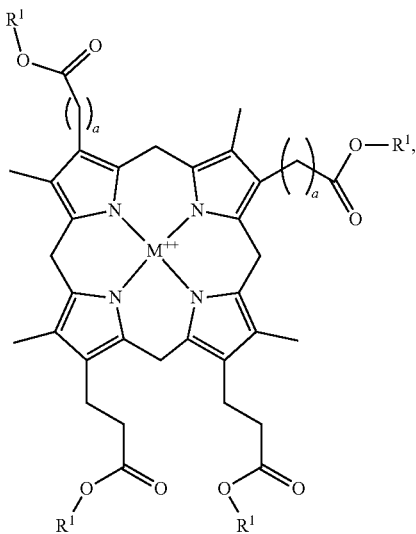

Formula IV

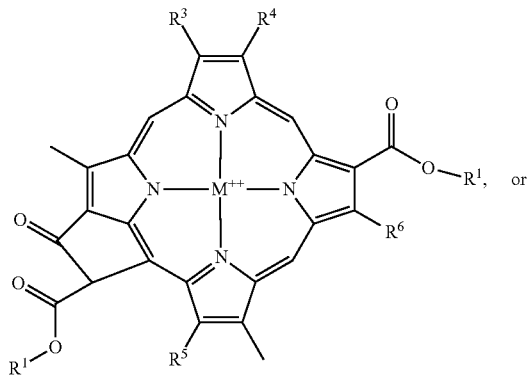

or

Formula V

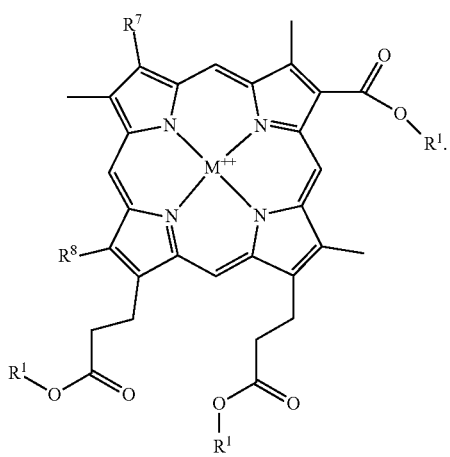

In Formulas I-V:

R[1] independently comprises the structure:

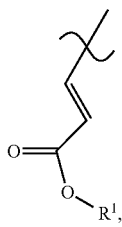

A is independently an optionally substituted N-heterocyclic aromatic ring;

x, is independently an integer from 0 to 6;

a, if present, is independently 0 or 1;

R[2] is independently an aminoalkyl or aminoaryl; and

R[3], R[4], R[5], and R[6], if present, are selected from one of (a)-(e):

(a) ethyl, methyl,

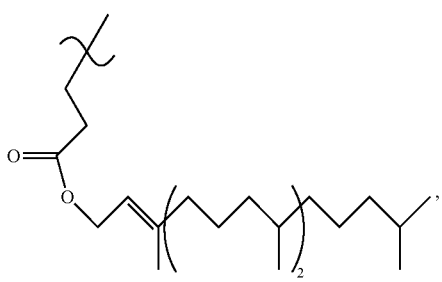

and methyl, respectively (Chlorophyll A, D);

(b) ethyl,

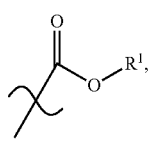

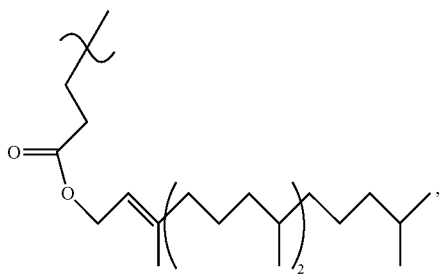

and methyl, respectively (Chlorophyll B);

(c) ethyl, methyl,

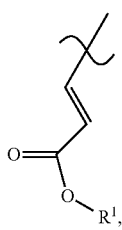

and methyl, respectively (Chlorophyll C1);

(d)

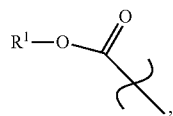

methyl,

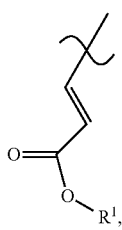

and methyl, respectively (Chlorophyll C2);

(e) ethyl, methyl,

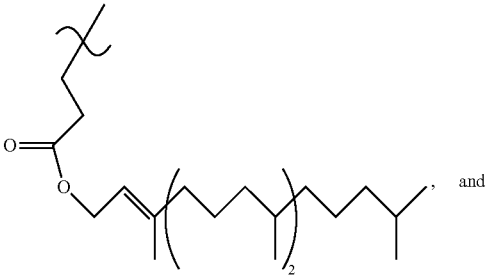

and

-continued

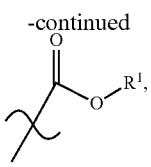

respectively (Chlorophyll F);
$R^7$ and $R^8$, if present, are selected from one of (f)-(h):
(f)

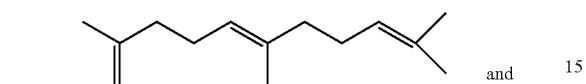 and respectively (Heme A);
(g)

and methyl, respectively (Heme B);
(h)

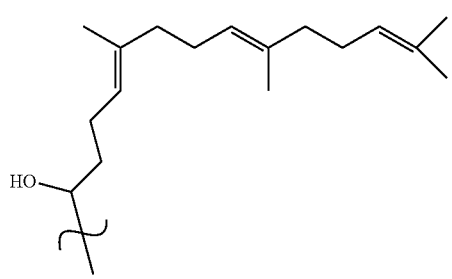 [SMILES: CCC(O)CC/C=C(\C)CC/C=C(\C)CCC=C(C)C]

and methyl, respectively, (Heme O); and
M is a metal selected from the group consisting of manganese, iron, copper, cobalt, nickel, magnesium, and zinc, and optionally is not present.

In some embodiments the amine-functionalized porphyrin compound comprises a structure of any one of Formulas I-V, and ring A can be independently an optionally substituted azetyl, an optionally substituted pyrrolyl, an optionally substituted pyridinyl, an optionally substituted azepinyl, or an optionally substituted azocinyl. In some embodiments, ring A is an optionally substituted pyridinyl.

In some embodiments the amine-functionalized porphyrin compound comprises a structure of any one of Formulas I-V, and $R^1$ comprises:

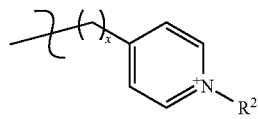

and x is 0 or 1. In additional embodiments, $R^1$ comprises

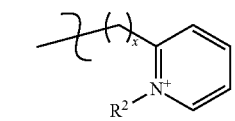

and x is 0 or 1. In some embodiments the amine-functionalized porphyrin compound comprises a structure of any one of Formulas I-V, and $R^2$ is aminoethyl.

In some embodiments the amine-functionalized porphyrin compound comprises a structure set forth as any one of Structure 5-39, such as any one of:

Structure 7

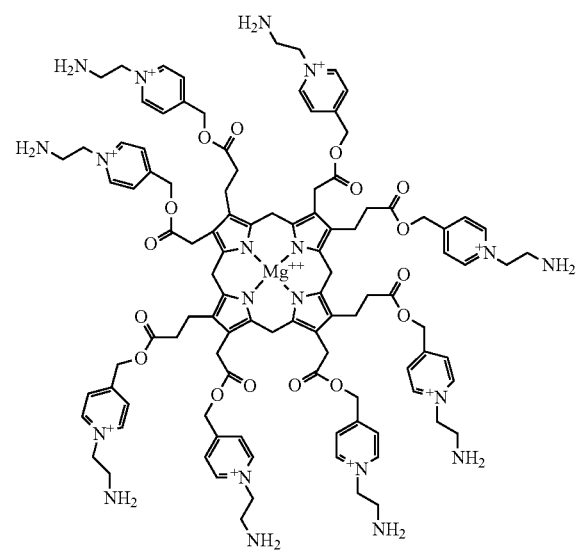

Structure 12
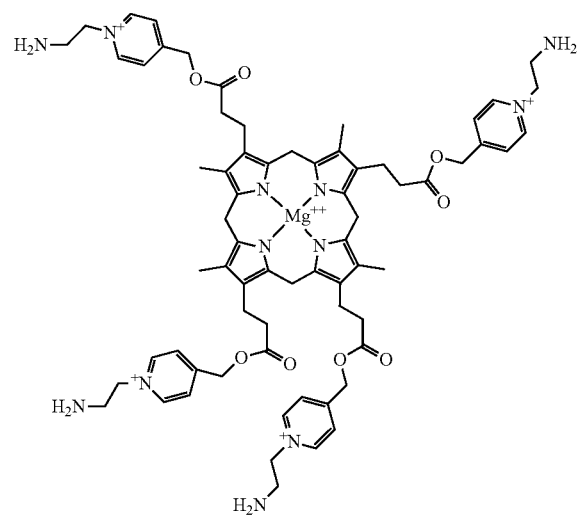
Structure 13
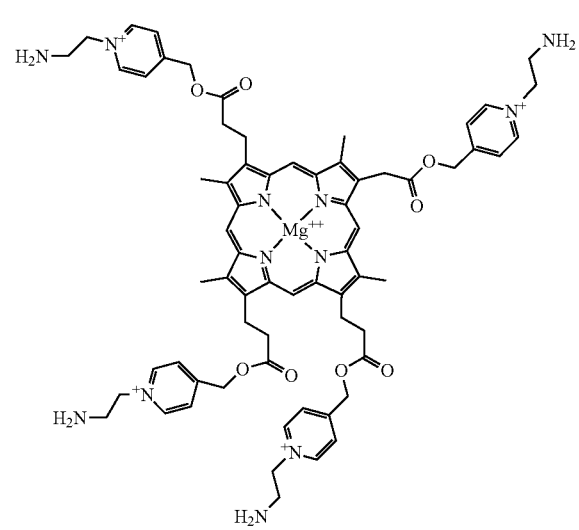
Structure 29
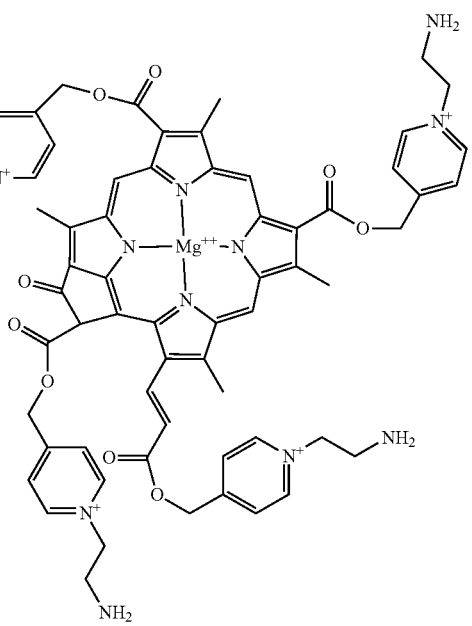
Structure 39
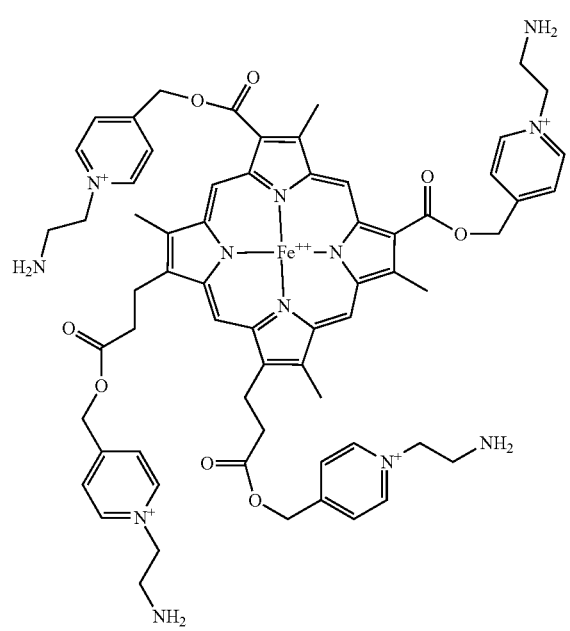

-continued

Structure 3

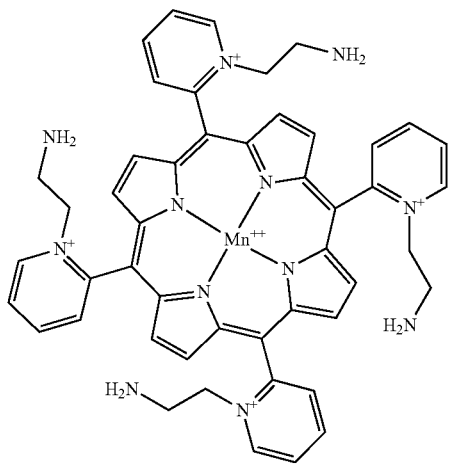

In several embodiments, a medical implant is provided, the implant comprising a surface for contacting a tissue in a subject, wherein the surface is coated with or linked to an effective amount of a disclosed amine functionalized porphyrin compound. The medical implant can be, for example, a dental implant, a heart valve, a vascular stent, a neural tissue implant, an orthopedic implant, a pacemaker, an electoral lead, a neural probe for recording and/or stimulating a neural signal, or a medical catheter. In some embodiments, the medical implant can comprise a surface for contacting a tissue in a subject comprising from about 0.1 ng/mm$^2$ to about 10 ng/m$^2$ of the amine functionalized porphyrin compound.

In additional embodiments, an epoxy, a nylon, or a hydrogel is provided, comprising a disclosed amine functionalized porphyrin compound. In some embodiments, the epoxy, the nylon, or the hydrogel can comprise from about 0.1 mg/ml to about 10 mg/ml of the compound. Addition of the amine functionalized porphyrin compound imparts antioxidant properties to the epoxy, the nylon, or the hydrogel.

In some embodiments, a method of reducing biofilm formation and/or biofouling on a surface is provided, comprising coating the surface with an effective amount of a amine functionalized porphyrin compound. In some embodiments, the surface is a surface of a medical device, for example an indwelling medical device such as an implant for example a catheter. In additional embodiments, the surface is a marine surface, for example, all or part of the surface of a hull, a pipe, a heat exchanger, or a valve, of a ship.

The foregoing and other objects, features, and advantages of the embodiments will become more apparent from the following detailed description, which proceeds with reference to the accompanying figures.

BRIEF DESCRIPTION OF THE FIGURES

(FIG. 1A) Alkylation of an 'ortho' position pyridyl results in a three dimensional structure that prevents intercalation with negatively charged biomolecules and subsequent toxicity. (FIG. 1B) The functional (primary amine) group on the iSODm compound can be linked to a silica surface using heterobifunctional crosslinker chemistry for immobilization purposes.

FIGS. 14A and 14B are digital images illustrating that an epoxy containing iSODm has anti-fouling properties. (FIG. 14A) Zebra mussels were placed on substrate coated with a marine epoxy coating (IL) or the same coating with 1% w/v iSODm additive (H) and were incubated in a freshwater tank. After 24 hours, the zebra mussels remained attached to the IL-coated substrate, but not the H coated-substrate. (FIG. 14B) The coated substrates were placed in a freshwater tank and algal growth was allowed to accumulate for one month. As shown in the figure, less algae accumulation was observed on substrate with the iSODm epoxy coating.

DETAILED DESCRIPTION

Figure 1A:
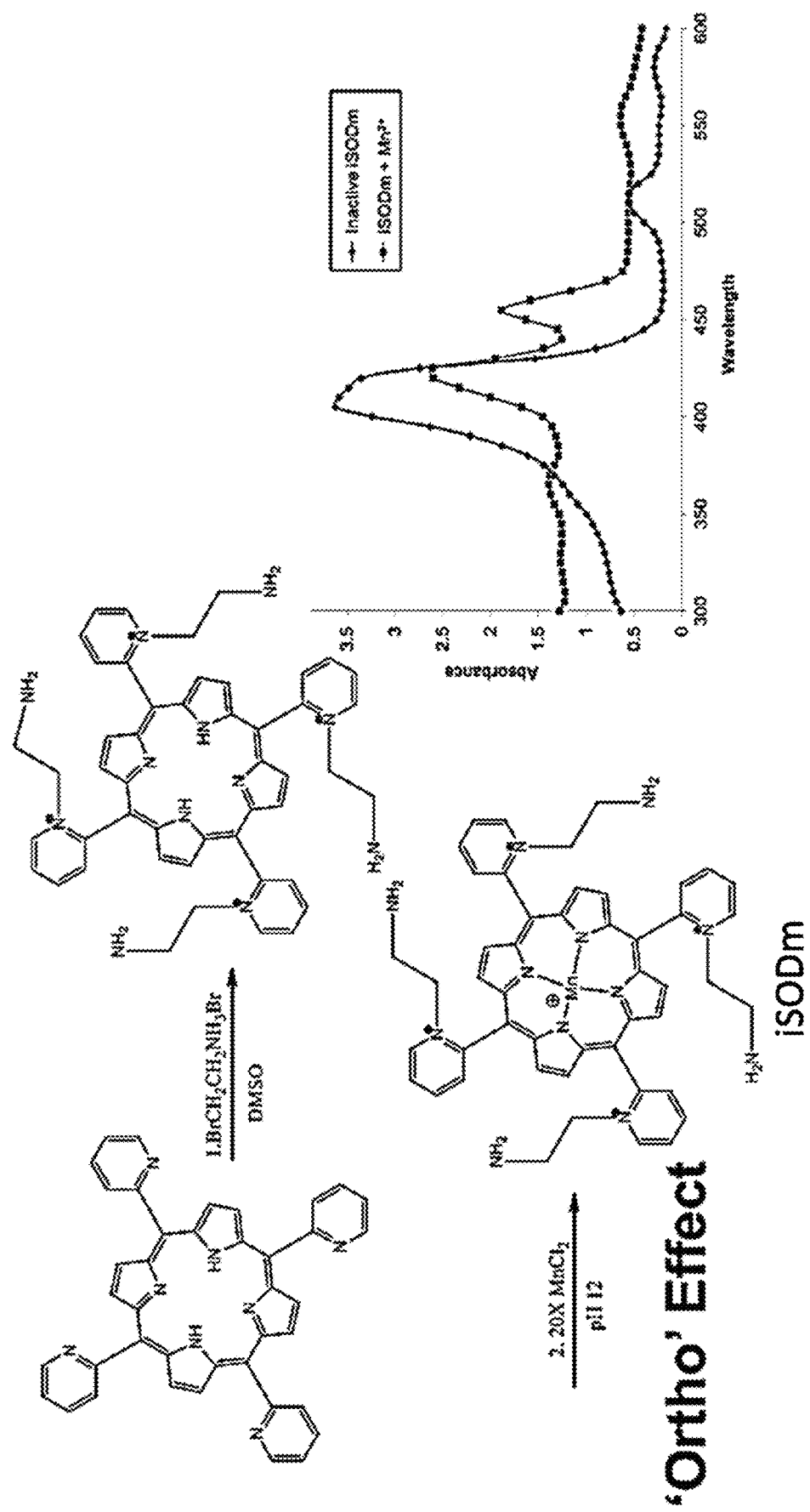
FIGS. 1A and 1B illustrate an exemplary synthesis scheme, structure, and conjugation method concerning a novel amine-functionalized porphyrin compound. The compound is an immobilizable superoxide dismutase mimic, termed iSODm.

Disclosed herein are novel amine-functionalized porphyrin compounds, and pharmaceutically acceptable salts or esters thereof. In several embodiments, the compounds can be used to impart antioxidant, anti-inflammatory, anti-microbial, and/or cell-adhesion specificity to a surface or material in need thereof, such as a surface of an indwelling medical implant, or a marine surface.

In some embodiments, the amine-functionalized porphyrin compounds can be applied to a surface as a self-assembled monolayer. Such coated surfaces have a wide variety of applications. Because self-assembled monolayers can be applied to both glass based substrates and metal based substrates there are many applications in both medical and industrial sectors. For example, surfaces coated with an amine-functionalized porphyrin can be used on indwelling medical devices, for example medical implants (such as neuronal probes or dental implants) as well as other medical surfaces (hospital surfaces, tools, etc.).

Several unique and unexpected properties were observed by incorporating the amine-functionalized porphyrin into a self-assembled monolayer surface coating. For example, surfaces coated with a disclosed amine-functionalized porphyrin exhibited increased attachment of neuronal and astrocyte cells, but decreased attachment of inflammatory cells, compared to uncoated surfaces. Further, an unexpectedly high density of neuronal cells was observed around implanted neuronal probes coated with the amine-functionalized porphyrin compared to uncoated probes in an in vivo model. Based on the disclosed in vitro and in vivo results, materials containing or coated with the amine-functionalized porphyrin can have an 'adhesion specificity' for non-inflammatory cells, such as neurons and astrocytes, compared to inflammatory cells, such as microglia. One non-limiting explanation for the cell-adhesive specificity is that this characteristic is due to synergy of the antioxidant performance, charge, and steric characteristics of the amine-functionalized porphyrin compound.

Further, materials containing or coated with a disclosed amine-functionalized porphyrin are shown to have anti-fouling properties. For example, such materials can reduce growth of biological contaminants such as micro-contaminants (e.g., bacteria and fungi) and macro-contaminant (e.g., mussels and barnacles). Accordingly, the amine-functionalized porphyrin compounds can be used on coatings or materials (such as marine coatings or materials) to reduce biofouling, such as glass materials (e.g., for fish tanks, underwater cameras, etc.) and metal materials (e.g., ship hulls, propellers, underwater hardware, etc.).

I. Summary of Terms

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting. To facilitate review of the various embodiments, the following explanations of terms are provided:

About: With reference to a numerical parameter, the term "about" refers to a plus or minus 5% range around the numerical parameter. For example, "about 5%" refers to "4.75% to 5.25%."

Acyl: A group having the structure —C(O)R, where R may be, for example, optionally substituted alkyl, optionally substituted aryl, or optionally substituted heteroaryl. Lower acyl groups are those that contain one to six carbon atoms.

Acyloxy: A group having the structure —OC(O)R—, where R may be, for example, optionally substituted alkyl, optionally substituted aryl, or optionally substituted heteroaryl. Lower acyloxy groups contain one to six carbon atoms.

Aliphatic: A group including alkyl, alkenyl, alkynyl, halogenated alkyl and cycloalkyl groups. A lower aliphatic group is a branched or unbranched aliphatic group having from one to ten carbon atoms.

Alkanediyl, cycloalkanediyl, aryldiyl, alkanearyldiyl: A divalent radical derived from aliphatic, cycloaliphatic, aryl, and alkanearyl hydrocarbons.

Alkenyl: A cyclic, branched or straight chain group containing only carbon and hydrogen, and containing one or more double bonds that may or may not be conjugated. Alkenyl groups may be unsubstituted or substituted. Lower alkenyl groups contain one to six carbon atoms.

Alkoxy: A straight, branched or cyclic hydrocarbon configuration and combinations thereof, including from 1 to 20 carbon atoms, preferably from 1 to 6 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

Alkoxycarbonyl: An alkoxy substituted carbonyl radical, —C(O)OR, wherein R represents an optionally substituted alkyl, aryl, aralkyl, cycloalkyl, cycloalkylalkyl or similar moiety.

Alkyl: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A lower alkyl group is a saturated branched or unbranched hydrocarbon having from 1 to 6 carbon atoms. Preferred alkyl groups have 1 to 4 carbon atoms. Alkyl groups may be substituted alkyls wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

Alkynyl: A cyclic, branched or straight chain group containing only carbon and hydrogen, and unless otherwise mentioned typically contains one to twelve carbon atoms, and contains one or more triple bonds. Alkynyl groups may be unsubstituted or substituted. A lower alkynyl group is one that contains one to six carbon atoms.

Amine or Amino: A group of the formula —NRR', where R and R' can be, independently, hydrogen or an alkyl, alkenyl, alkynyl, aryl, aralkyl, cycloalkyl, halogenated alkyl, or heterocycloalkyl group.

Aminoalkyl: An alkyl group where at least one hydrogen atom is replaced with an amino group (e.g., —$CH_2$—$NH_2$).

Aminoaryl: An aryl group where at least one hydrogen atom is replaced with an amino group (e.g., —$CH_2$—$NH_2$).

Aminocarbonyl: A group that, alone or in combination, includes an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

Amide or Amido: A group that is represented by the formula —C(O)NRR', where R and R' independently can be a hydrogen, alkyl, alkenyl, alkynyl, aryl, aralkyl, cycloalkyl, halogenated alkyl, or heterocycloalkyl group.

Analog: A molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

Antioxidant: A substance that, when present in a mixture or structure containing an oxidizable substrate molecule (for example, an oxidizable biological molecule), significantly delays or prevents oxidation of the oxidizable substrate molecule. Antioxidants can act by scavenging biologically important reactive free radicals or other reactive oxygen species (ROS), or by preventing their formation, or by catalytically converting the free radical or other ROS to a less reactive species. Cells have endogenous antioxidant machinery, such as superoxide dismutase. In several embodiments, a disclosed amine-functionalized porphyrin compound is an antioxidant.

Aralkyl: An alkyl group wherein an aryl group is substituted for a hydrogen of the alkyl group. An example of an aralkyl group is a benzyl group.

Aryl: A monovalent unsaturated aromatic carbocyclic group having a single ring (e.g., phenyl) or multiple condensed rings (e.g., naphthyl or anthryl), which can optionally be unsubstituted or substituted. A heteroaryl group is an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

Biofilm: A mass, aggregation, or community of microorganisms attached to a non-living surface (such as a surface of a medical implant, a household surface, a food preparation object, or a fluid-conducting device having a lumen, such as a pipe, tubing, or a catheter), and the associated extracellular substances produced by one or more of the attached microorganisms. The extracellular substances are typically polymeric substances that include a matrix of complex polysaccharides, proteinaceous substances, nucleic acids, and glycopeptides. The microorganisms in a biofilm may include, but are not limited to, bacteria, fungi and protozoa. The nature of a biofilm, such as its structure and composition, may depend on the particular microorganisms present in the biofilm.

Biofouling: Accumulation of microorganisms, plants, and/or animals on a surface exposed to wet conditions, such as a marine surface exposed to seawater or a surface of an indwelling medical implant exposed to biological fluid or tissue. Biofouling includes microbiofouling, such as formation of a biofilm including microorganisms, and macrobiofouling, such as attachment of plants and/or animals (for example barnacles or mussels) to a marine surface.

Coat: A layer of material that partially or fully covers a surface. In several embodiments, a medical implant can include an external surface with a coat containing of an effective amount of an amine-functionalized porphyrin as disclosed herein. In additional embodiments, a disclosed amine-functionalized porphyrin can be coated onto a surface for industrial use, for example to provide anti-biofouling properties to a marine surface. The surface does not need to be completely coated with the amine-functionalized porphyrin (and in many cases is partially coated). Further, the amount of amine-functionalized porphyrin included in the coating can vary according to the application parameters, e.g., time of use, exposure, level of signals, levels of noise, desired compound density, etc.

Coating material can be applied to an underlying surface in various ways known in the art and describe herein. Non-limiting examples of methods that can be used to apply the amine-functionalized porphyrin to the external surface of the implant include coating methods such as dipping, spraying, painting, vacuum deposition, conjugation to an external surface of the device, or by any other method known to those of ordinary skill in the art.

Cycloalkyl: A non-aromatic carbon-based ring composed of at least three carbon atoms. Examples of cycloalkyl groups include, but are not limited to, cyclopropyl, cyclobutyl, cyclopentyl, cyclohexyl, and the like. A heterocycloalkyl group is a cycloalkyl group as defined above where at least one of the carbon atoms of the ring is substituted with a heteroatom such as, but not limited to, nitrogen, oxygen, sulfur, or phosphorous.

Effective amount: The amount of a compound (such as an amine-functionalized metalloporphyrin) that alone, or together with one or more additional compounds, induces the desired response, such as, for example, an increase in antioxidant activity, an increase in anti-inflammatory activity, an increase in anti-microbial activity, a reduction in biofouling, a reduction in biofilm accumulation, and/or cell-adhesion specificity, to a surface or material in need thereof, such as a surface of an indwelling medical implant, or a marine surface.

The effective amount of an amine-functionalized porphyrin will depend on the particular amine-functionalized porphyrin, the substrate to which the amine-functionalized porphyrin is conjugated (if any), the particular application of the amine-functionalized porphyrin, and the like.

Electrode: An electric conductor through which an electric current can pass. An electrode can also be a collector and/or emitter of an electric current. In some embodiments, an electrode is a solid and comprises a conducting metal as the conductive layer. Non-limiting examples of conducting metals include noble metals and alloys, such as stainless steel and tungsten. An "array of electrodes" refers to a device with at least two electrodes formed in any pattern. The electrodes can be either interconnected or independently wired.

Epoxy: Cross-linked epoxy resin. Epoxy resins contain pre-polymer moieties containing free epoxide groups. Addition of appropriate cross-linker (or curing agent) to the epoxy resin cross-links the epoxide groups to form the epoxy. In some embodiments, the amine-functionalized porphyrin compounds disclosed herein (such as iSODm) can be used as a curing agent for an epoxy containing an epoxy resin that can be crosslinked using a compound containing multiple primary-amines. In some embodiments, the amine-functionalized porphyrin compounds disclosed herein (such as iSODm) can be included as an additive in a curing agent composition for an epoxy for an epoxy containing an epoxy resin that can be crosslinked using a compound containing multiple primary-amines Implanting: Completely or partially placing a medical implant (such as a catheter or a neural probe) within a subject, for example, using surgical techniques. A medical implant is partially implanted when some of the implant reaches, or extends to the outside of, a subject. In some embodiments, a medical implant may be a neuronal implant that can be implanted into neural tissue, such as the central nervous system, more particularly the brain, for treatment of different medical conditions and for various time periods (such as for a short term duration (e.g., one or two days or less) or for long-term or chronic duration (e.g., one month or more)).

Indwelling medical device: A device for medical treatment or diagnosis that is designed for prolonged placement within or partially within a living body.

Inflammation: When damage to tissue occurs, the body's response to the damage is usually inflammation. For example, the damage may be due to insertion of a medical device into the body, such as a neural implant. This generalized response by the body includes the release of many components of the immune system (for instance, IL-1 and TNF), attraction of cells to the site of the damage, swelling of tissue due to the release of fluid and other processes. Inflammation may be measured by many methods well known in the art, such as the number of leukocytes, the number of polymorphonuclear neutrophils (PMN), a measure of the degree of PMN activation, such as luminal enhanced-chemiluminescence, or a measure of the amount of cytokines present.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

Medical Implant: Any device intended to be partially or wholly introduced, inserted, or implanted within a subject's body for one or more therapeutic or prophylactic purposes, such as for restoring physiological function, alleviating symptoms associated with disease, delivering therapeutic agents, detecting changes (or levels) in the internal environment, and/or repairing or replacing or augmenting damaged or diseased organs and tissues.

Non-limiting examples of medical implants include intravascular catheters (for example, intravenous and intra-arterial), right heart flow-directed catheters, Hickman catheters, arteriovenous fistulae, catheters used in hemodialysis and peritoneal dialysis (for example, silastic, central venous, Tenckhoff, and Teflon catheters), vascular access ports, indwelling urinary catheters, urinary catheters, silicone catheters, ventricular catheters, synthetic vascular prostheses (for example, aortofemoral and femoropopliteal), prosthetic heart valves, orthopedic implants, penile implants, neural tissue implants (for example spinal cord meshes, cranioplasty meshes, shunts (for example, Scribner, Torkildsen, central nervous system, portasystemic, ventricular, ventriculoperitoneal), intrauterine devices, dental implants, stents (for example, ureteral stents), artificial voice prostheses, tympanostomy tubes, gastric feeding tubes, endotracheal tubes, pacemakers, implantable defibrillators, bioelectronic devices such as intracochlear or intracranial electronic devices, including neural probes, ossiculoplastic implants; middle ear implants including incus, malleus, stages, incus-stapes, malleus-incus, malleus-incus-stapes; cochlear implants; implants for retention of hearing aids; implants for external fixation; tubing, cannulas, probes, blood monitoring devices, needles, mouth guards, night guards, dentures, orthodontic retainers, contact lenses, and the like.

The medical implant can be wholly embedded in the subject (for example, a prosthetic joint, a prosthetic heart valve, or a pacemaker). In some embodiments, the medical implant can be partially embedded in the subject and has both internal and external parts, relative to the subject (for example, a urinary catheter, a gastric feeding tube, or a dental implant).

In some embodiments, a medical implant can be surgically implanted (for example, a pacemaker, dental implants, prosthetic joints, vascular prostheses, or shunts). In other embodiments, a medical implant can be inserted into the subject by a medical professional using non-surgical means (for example, an intrauterine device, an endotracheal tube, or a urinary catheter). In yet other embodiments, a medical implant includes devices that are routinely inserted and removed by the subject (for example, an inserted medical implant) without intervention or aide by a medical professional (for example, a mouth guard, a night guard, removable dentures, an orthodontic retainer, or a contact lens).

Medical implants can be introduced by any suitable means, for example, by percutaneous, intravascular, intraurethral, intra-orbital, intra-oral, intra-tracheal, intra-esophageal, stomal, or other route, or by surgical implantation, for example intra-articular placement of a prosthetic joint.

In some embodiments, the medical implant can be an orthopedic implant, which is a medical implant that replaces anatomy or restores a function of the musculoskeletal system such as the femoral hip joint; the femoral head; acetabular cup; elbow including stems, wedges, articular inserts; knee, including the femoral and tibial components, stem, wedges, articular inserts or patellar components; shoulders including stem and head; wrist; ankles; hand; fingers; toes; vertebrae; spinal discs; artificial joints; orthopedic fixation devices such as nails, screws, staples and plates.

In some embodiments, the medical implant can be a dental implant, which is any device intended to be implanted into the oral cavity of a vertebrate animal, in particular a mammal such as a human, in tooth restoration procedures. Generally, a dental implant is composed of one or several implant parts. For instance, a dental implant typically includes a dental fixture (or post) coupled to secondary implant parts, such as an abutment and/or a dental restoration such as a crown, bridge or denture. However, any device, such as a dental fixture, intended for implantation may alone be referred to as an implant even if other parts are to be connected thereto.

In some embodiments, the medical implant can be a neural implant, which can be any medical implant including one or more electrodes that can be placed in contact with neuronal tissue in an animal host and can record and/or stimulate neural signals from or to the neuronal tissue. Neural probes typically include conductive and non-conductive surfaces designed for contact with neuronal tissue when implanted in a subject, and can include one or more electrodes that can be independently monitored from other conductive surfaces on or off the probe) for recording and/or stimulating neural signals. In several embodiments, the disclosed probes are included in a device (such as an array or a deep brain stimulator) for recording and/or stimulating a neural signal in a subject. Methods of making electrodes for recording and/or stimulating a neural signal that are coated (fully or partially) with an insulting layer (including a parylene C insulating layer) are known in the art; see, e.g., U.S. Pat. No. 8,355,802 and WO 2005/114720, which are incorporated by reference herein in their entirety.

N-heterocyclic: Mono-cyclic rings that include at least one nitrogen heteroatom. The rings generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Non-limiting examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl.

Non-limiting examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Neural signal: An electrical signal originating in the nervous system of a subject. "Recording a neural signal" refers to recording an electrical signal that independently exists outside of the membrane or wall of a cell. "Stimulating a neural signal" refers to application of an electrical current to the neural tissue of a subject in such a way as to cause neurons in the subject to produce an electrical signal (e.g., an action potential). An extracellular electrical signal can, however, originate in a cell, such as one or more neural cells. An extracellular electrical signal is contrasted with an intracellular electrical signal, which originates, and remains, in a cell. An extracellular electrical signal can comprise a collection of extracellular electrical signals generated by one or more cells. The person of ordinary skill in the art is familiar with methods for recording electrical signals using a device including an implanted electrode.

Nylon: A synthetic polymer or copolymer including aliphatic or aromatic polyamides. A polymer is a molecule of repeating structural units (e.g., monomers) formed via a chemical reaction, i.e., polymerization. In some embodiments, a nylon can include an effective amount of a disclosed amine-functionalized porphyrin.

Porphyrin: A family of heterocyclic compounds including four modified pyrrole groups interconnected via their α carbon atoms by methine bridges. Porphyrins can complex positively charged metal ions, such as manganese, magnesium, and iron, via the nitrogen atoms of the four pyrrole groups. Porphyrins include synthetic porphyrins (such as meso-Tetra(2-pyridyl) porphine) as well as naturally occurring Heme porphyrins (animal based, iron containing porphyrins), such as Heme A, Heme B, Heme C, or Heme O, and naturally occurring Chlorophyll porphyrins (plant based, magnesium containing porphyrins), such as Chlorophyll A, Chlorophyll B, Chlorophyll $C_1$, Chlorophyll $C_2$, Chlorophyll D, or Chlorophyll F. Additional examples of porphyrins include precursors of Heme and Chlorophyll, such as Uroporphyrinogen III, Coproporphyrinogen III, Protoporphyrinogen IX, or Protoporphyrin IX. In several embodiments, porphyrin compounds include functional groups such as carboxylic acids, esters, and terminal alkenes, that can be targeted for modification to make an amine-functionalized porphyrin compound as described herein.

Subject: Living multi-cellular vertebrate organisms, a category that includes human and non-human mammals, including non-human primates, rats, mice, guinea pigs, cats, dogs, cows, horses, and the like. Thus, the term "subject" includes both human and veterinary subjects.

Substituted or Substitution: Replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$ alkyl, $C_{2-6}$alkenyl, $C_{2-6}$alkynyl, $C_{3-8}$acycloalkyl, hydroxyl, oxo, $C_{1-6}$alkoxy, aryloxy, $C_{1-6}$-alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, $arC_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

Surface: An external aspect of an object, device, tissue, or organ that can interact with its surrounding environment.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." Therefore, comprising "A" or "B" refers to including A, including B, or including both A and B. Although methods and materials similar or equivalent to those described herein can be used in the practice or testing of the present disclosure, suitable methods and materials are described herein. In case of conflict, the present specification, including explanations of terms, will control. In addition, the materials, methods, and examples are illustrative only and not intended to be limiting.

II. Compounds

Disclosed herein are novel amine-functionalized porphyrin compounds, as wells as pharmaceutically acceptable salts or esters thereof. In several embodiments, these compounds can be used to impart antioxidant, anti-inflammatory, anti-microbial, and/or cell-adhesion specificity to a surface or material in need thereof, such as a surface of an indwelling medical device (for example, a medical implant), or a marine surface.

The amine-functionalized porphyrin compounds can be applied to a surface as a self-assembled monolayer. Such coated surfaces have a wide variety of applications. Because self-assembled monolayers can be applied to any 'oxide' surface, such as glass based substrates and metal based substrates, there are many applications in both medical and industrial sectors. For example, surfaces coated with an amine-functionalized porphyrin can be used in medical implants (such as neuronal implants or dental implants) as well as other medical surfaces (hospital surfaces, tools, etc.).

Materials containing or coated with an amine-functionalized porphyrin are shown to have anti-fouling properties, that is, such materials exhibit reduced growth of microorganism contaminants such as bacteria and fungi, as well as macro contaminants, such as mussels and barnacles). Accordingly, amine-functionalized porphyrin compounds can be used on coatings and/or materials with applications in aquatic environments, such as glass materials (e.g., for fish tanks, underwater cameras, etc.) and metal materials (e.g., ship hulls, propellers, underwater hardware, etc.).

In some embodiments, the disclosed amine-functionalized porphyrin compound can be an amine-functionalized metalloporphyrin compound. The embodiments include both metal-free and metal-bound porphyrin compounds. In the case of metal-bound porphyrin, manganese-substituted porphyrins are preferred, however, metals other than manganese such as iron (II or III), copper (I or II), cobalt (II or III), nickel (I or II), magnesium, or zinc can also be used. It will be appreciated that the metal selected can have various valence states, for example, manganese II, III or V can be used.

The amine-functionalized porphyrin compound can be based on any suitable porphyrin. Non-limiting examples of porphyrin compounds that can be modified to make the amine-functionalized porphyrin include synthetic porphyrins, as well as plant and animal based porphyrins. In some embodiments, the amine-functionalized porphyrin can be a modified form of a Heme (an iron containing porphyrin), such as Heme A, Heme B, Heme C, or Heme O. In additional embodiments, the amine-functionalized porphyrin can be a modified form of a Chlorophyll (a magnesium containing porphyrin), such as Chlorophyll A, Chlorophyll B, Chlorophyll $C_1$, Chlorophyll $C_2$, Chlorophyll D, or Chlorophyll F. In additional embodiments, the amine-functionalized porphyrin can be a modified form of a precursor of a Chlorophyll or a Heme, such as Uroporphyrinogen III, Uroporphyrin III, Coproporphyrinogen III, Coproporphyrin III, Protoporphyrinogen IX, or Protoporphyrin IX. These naturally occurring porphyrin containing compounds include functional groups such as carboxylic acids, esters, and terminal alkenes, that can be targeted for modification to make an amine-functionalized porphyrin compound as described herein. A non-limiting illustration of the chemistry that can be used to modify these compounds to add amine groups is provided in FIG. 13 (in the context of chlorophyll C2 and Heme B). In a non-limiting example, these porphyrin compounds can be amino-derivatized via esterification of carboxylic acid groups and/or vinyl groups.

In some embodiments, there is disclosed herein a compound, or a pharmaceutically acceptable salt or ester thereof, having a structure of:

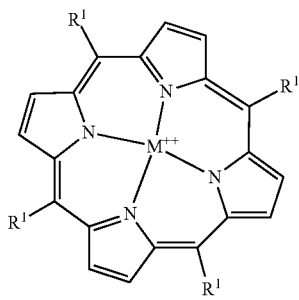

Formula I wherein R¹ independently comprises the structure:

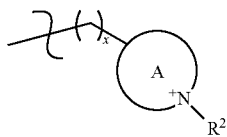

and A is independently an optionally substituted N-heterocyclic aromatic ring; x is independently an integer from 0 to 6 (such as 0); R² is independently an aminoalkyl or an aminoaryl; and M is a metal selected from the group consisting of manganese, iron, copper, cobalt, nickel, magnesium, and zinc, and optionally is not present. In embodiments where M is not present, the surrounding nitrogen atoms can be fully, partially, or not, hydrogenated. In several such embodiments, M is manganese. In some embodiments of Formula I, A is independently an optionally substituted 4 to 7 membered N-heterocyclic aromatic ring. In some embodiments of Formula I, A is independently an optionally substituted azetyl, an optionally substituted pyrrolyl, an optionally substituted pyridinyl, an optionally substituted azepinyl, or an optionally substituted azocinyl. In some embodiments of Formula I, A is an optionally substituted pyridinyl.

In some embodiments of Formula I,

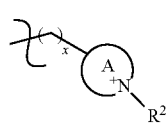

can be one of:

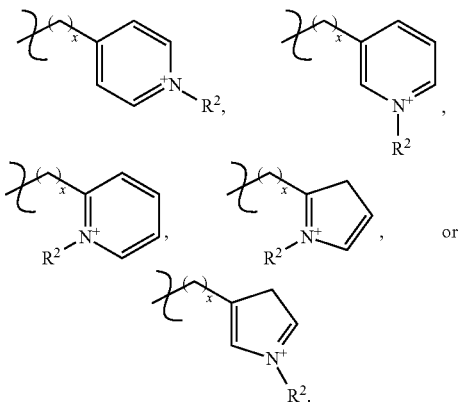

In several such embodiments, x can be 0 or 1.

In some embodiments of Formula I, R² can be independently a lower aminoalkyl or lower aminoaryl. In some embodiments of Formula I, R² can be aminoethyl. In some embodiments, R¹ is independently selected from one of:

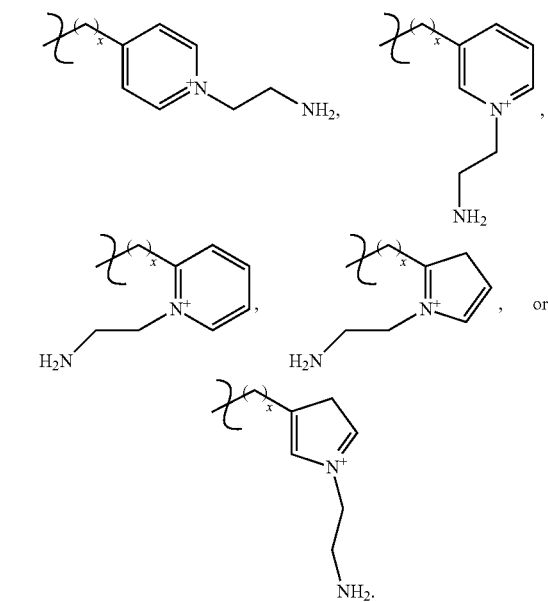

In several such embodiments, x can be 0 or 1.

In some embodiments of Formula I, R² can be

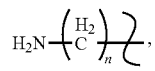

wherein n is from 0 to 10. For example, in some embodiments of Formula I, R² can be any one of:

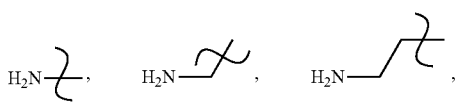

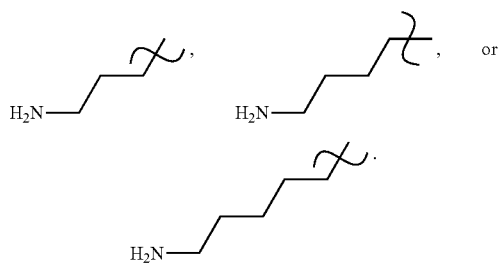

In some embodiments of Formula I, $R^2$ can have a formula of

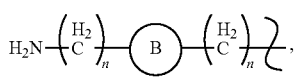

wherein n is independently 0 to 10 and B is selected from a 4 to 7 membered cycloaliphatic, optionally-substituted heterocycloaliphatic, optionally-substituted aryl, or optionally-substituted heteroaryl. In some embodiments of Formula I, $R^2$ can have a formula of

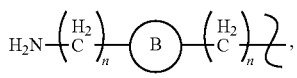

wherein n is independently 0 to 10 and B is selected from optionally-substituted pyrrolidine, optionally-substituted imidizolidine, optionally-substituted pryazolidine, optionally-substituted pyrrole, optionally-substituted diazole, optionally-substituted triazole, optionally-substituted piperidine, optionally-substituted pyridine, optionally-substituted diazine, optionally substituted triazine, optionally-substituted piperazine, optionally-substituted azepane, or optionally-substituted azepine.

In some embodiments of Formula I, the compound can have a structure set forth as one of:

Structure 1

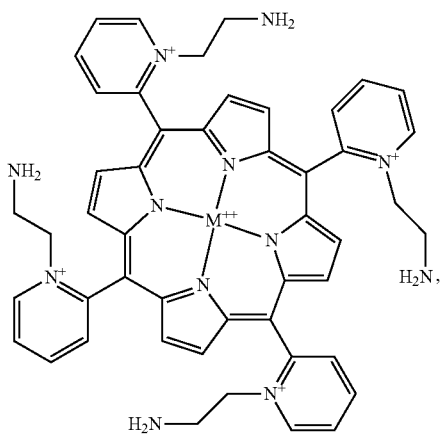

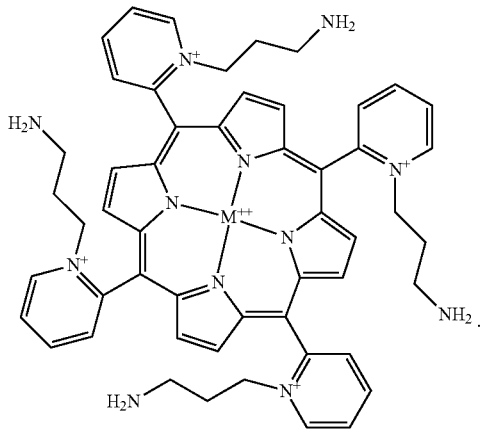

Structure 2

In some such embodiments, M is manganese. In some embodiments of Formula I, the compound can have a structure set forth as one of:

Structure 3

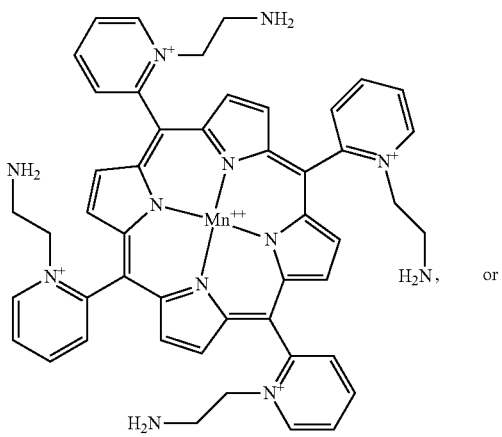

Structure 4

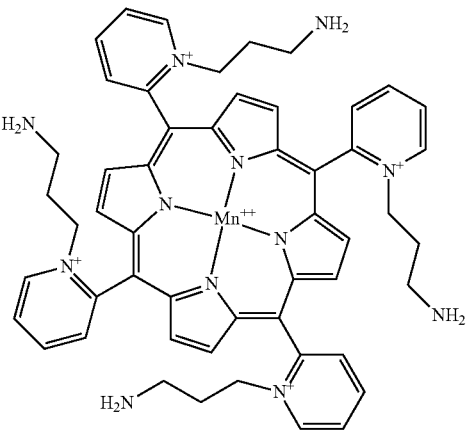

Amine Functionalization of Protoporphyrin IX and its Precursors

In some embodiments, the amine-functionalized porphyrin compound can be based on Uroporphyrinogen III or its dehydrogenated form, Uroprophyrin III. For example, in some embodiments, there is disclosed herein a compound, or a pharmaceutically acceptable salt or ester thereof, having a structure of:

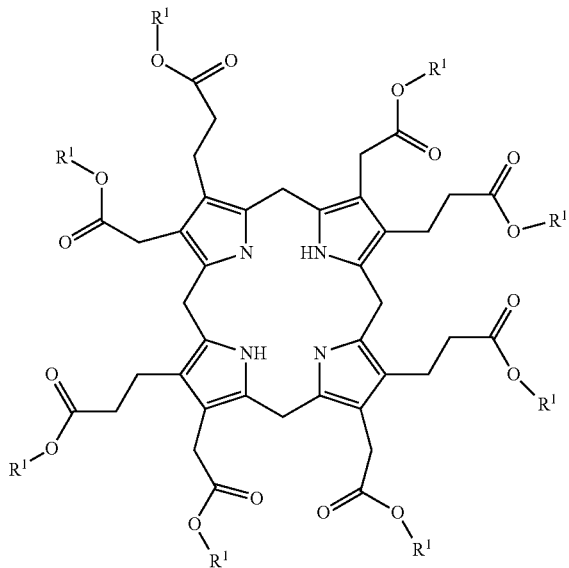

Formula II

In some embodiments, the amine-functionalized porphyrin compound can be based on Coproporphyrinogen III or Protoporphyrinogen IX, or their dehydrogenated forms, Coproporphyrin III or Protoporphyrin IX, respectively. For example, in some embodiments, there is disclosed herein a compound, or a pharmaceutically acceptable salt or ester thereof, having a structure of:

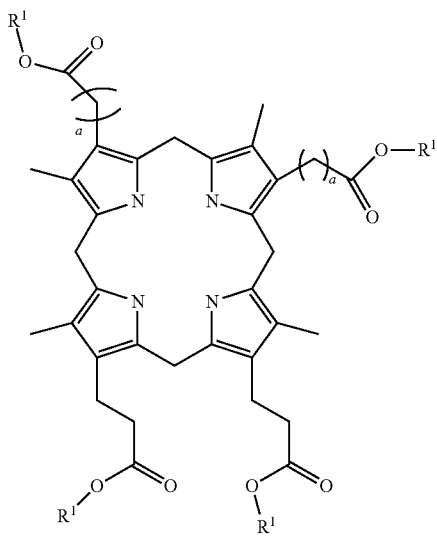

Formula III

In Formulas II and III, $R^1$ can independently comprise the structure:

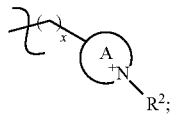

and

A is independently an optionally substituted N-heterocyclic aromatic ring; x is independently an integer from 0 to 6 (such as 0); $R^2$ is independently an aminoalkyl or an aminoaryl; a is 1 or 2; and M, if present, can be a metal selected from the group consisting of manganese, iron, copper, cobalt, nickel, magnesium, and zinc, and optionally is not present. In several such embodiments, M is manganese. In some such embodiments, M is manganese. In additional such embodiments, M is magnesium. In more embodiments, M is iron. In embodiments where M is not present, the surrounding nitrogen atoms can be fully, partially, or not, hydrogenated. For example, in Formula II, the nitrogen atoms at the center of the porphyrin are partially dehydrogenated (that is, only two of the four nitrogen atoms are hydrogenated). However, the amine-functionalized porphyrin of formula II can be further modified to include nitrogen atoms at the center of the porphyrin can be fully, partially, or not, hydrogenated.

In some embodiments of Formula II or III, A is independently an optionally substituted 4 to 7 membered N-heterocyclic aromatic ring. In some embodiments of Formulas II or III, A is independently an optionally substituted azetyl, an optionally substituted pyrrolyl, an optionally substituted pyridinyl, an optionally substituted azepinyl, or an optionally substituted azocinyl. In some embodiments of Formulas II or III, A is an optionally substituted pyridinyl.

In some embodiments of Formulas II or III,

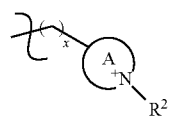

can be one of:

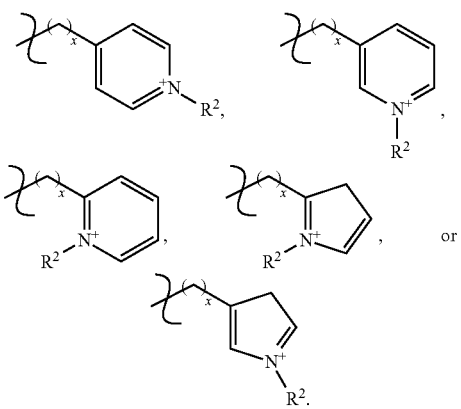

In several such embodiments, x can be 0 or 1.

In some embodiments of Formulas II or III, $R^2$ can be independently a lower aminoalkyl or lower aminoaryl. In some embodiments of Formulas II or III, $R^2$ can be aminoethyl. In some embodiments of Formulas II or III, $R^1$ is independently selected from one of:

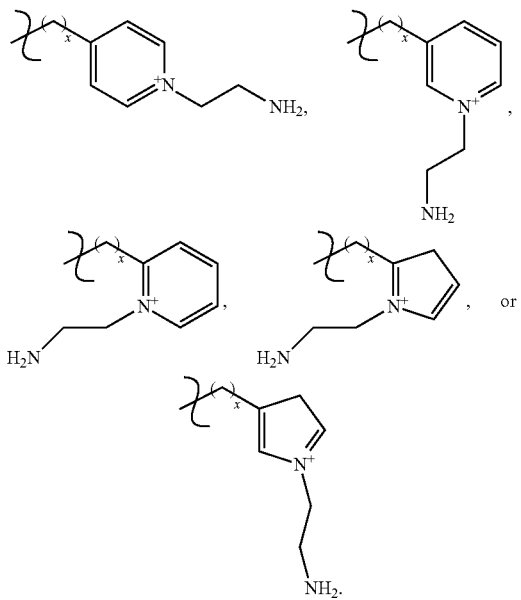

several such embodiments, x can be 0 or 1.

In some embodiments of Formulas II or III, $R^2$ can be

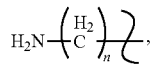

wherein n is from 0 to 10. For example, in some embodiments of Formulas II or III, $R^2$ can be any one of:

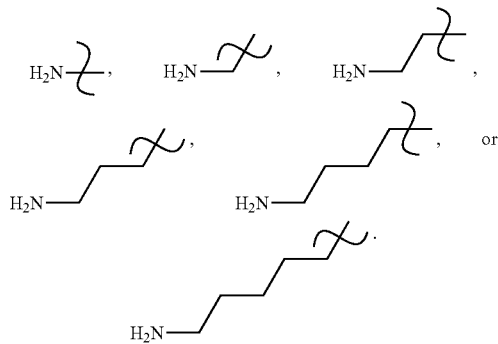

In some embodiments of Formulas II or III, $R^2$ can have a formula of

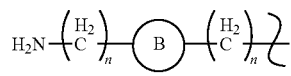

wherein n is independently 0 to 10 and B is selected from a 4 to 7 membered cycloaliphatic, optionally-substituted heterocycloaliphatic, optionally-substituted aryl, or optionally-substituted heteroaryl. In some embodiments of Formulas II or III, $R^2$ can have a formula of

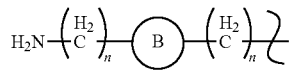

wherein n is independently 0 to 10 and B is selected from optionally-substituted pyrrolidine, optionally-substituted imidizolidine, optionally-substituted pryazolidine, optionally-substituted pyrrole, optionally-substituted diazole, optionally-substituted triazole, optionally-substituted piperidine, optionally-substituted pyridine, optionally-substituted diazine, optionally substituted triazine, optionally-substituted piperazine, optionally-substituted azepane, or optionally-substituted azepine.

In some embodiments of Formula II, the compound can have a structure set forth as one of:

Structure 5

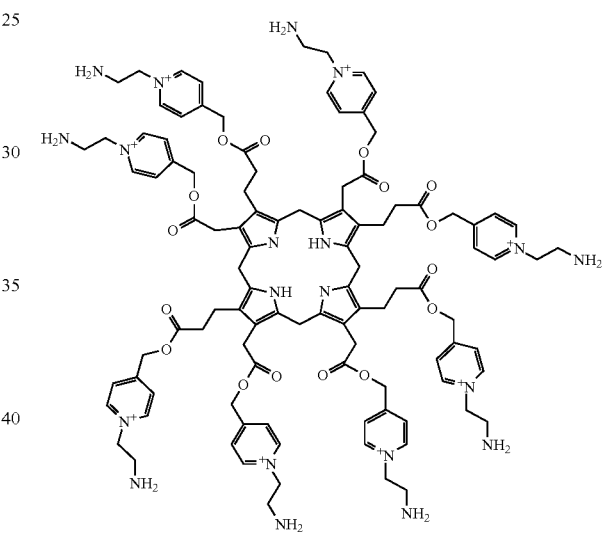

Structure 6

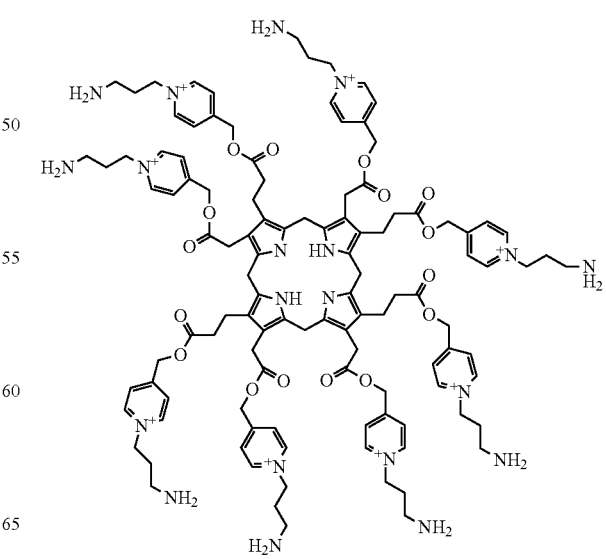

Structure 7
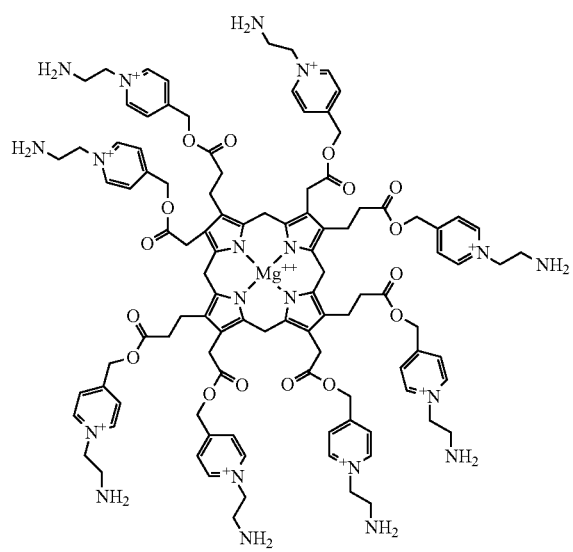
Structure 8
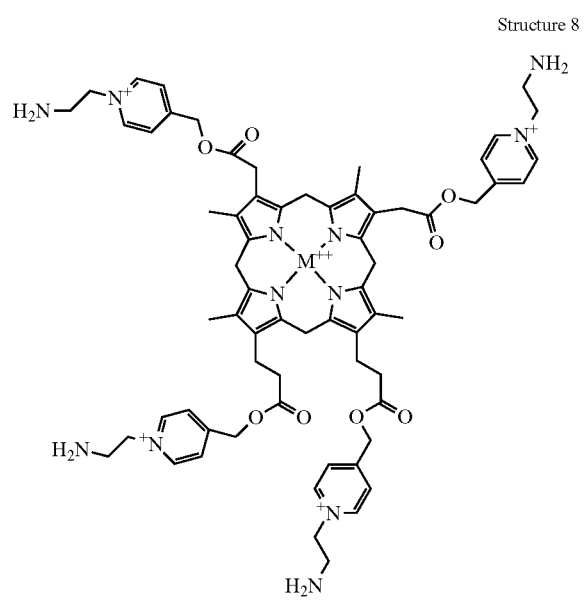
Structure 9
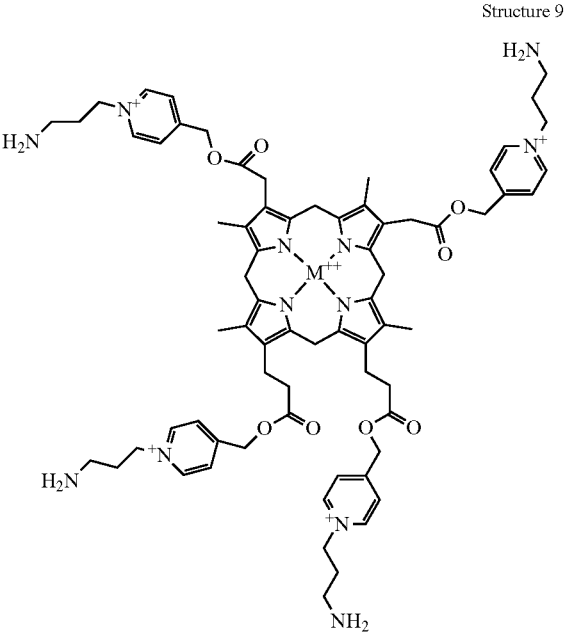
In some embodiments of Formula III, the compound can have a structure set forth as one of:
Structure 10
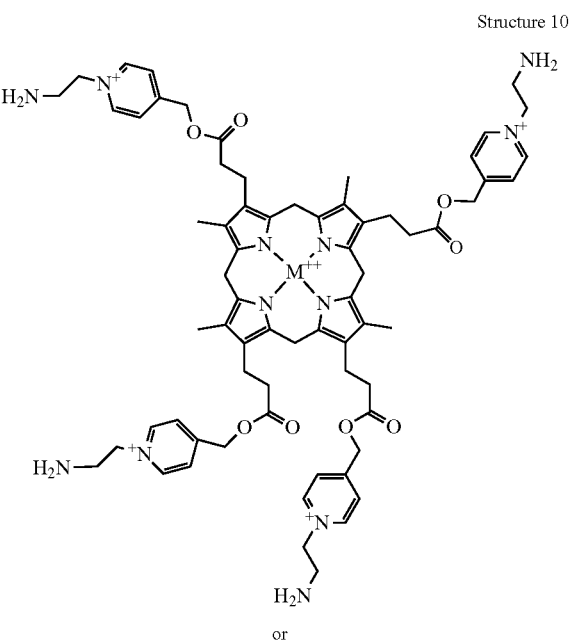
or Structure 11
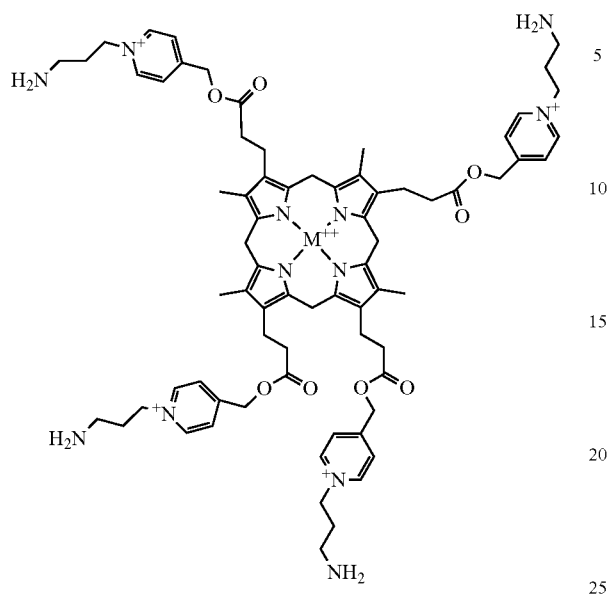
Structure 13
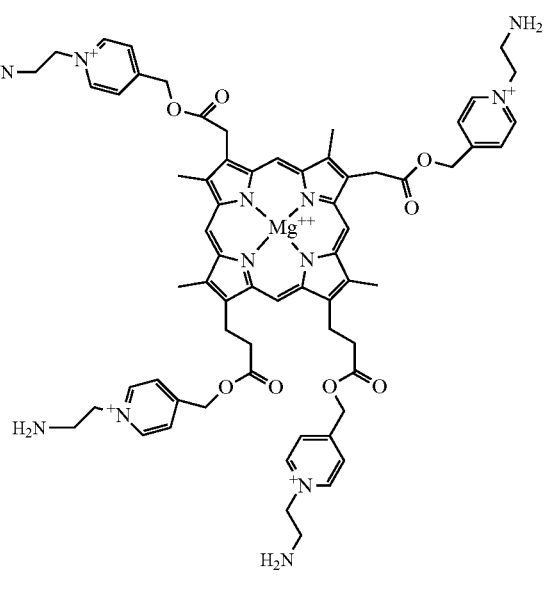
In several such embodiments, M can be magnesium. In some embodiments of Formula III, the compound can have a structure set forth as one of:
Structure 12
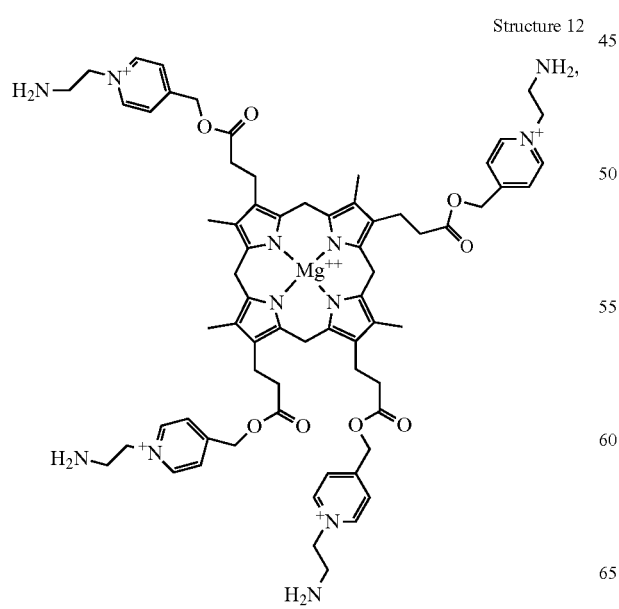
Structure 14
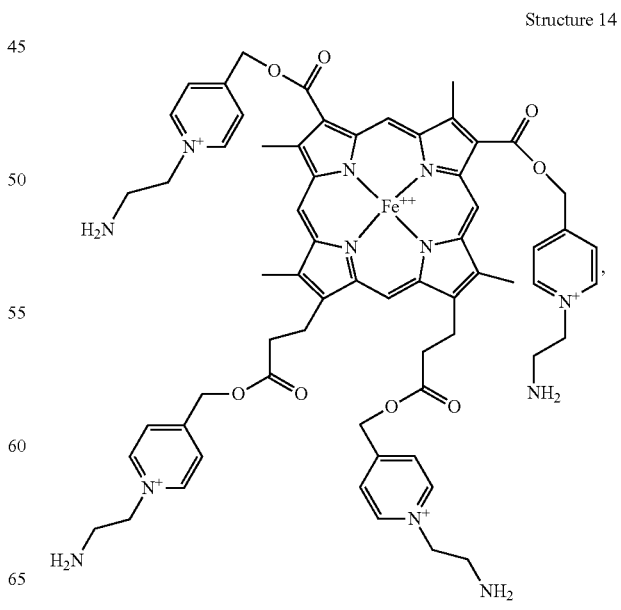

Structure 15

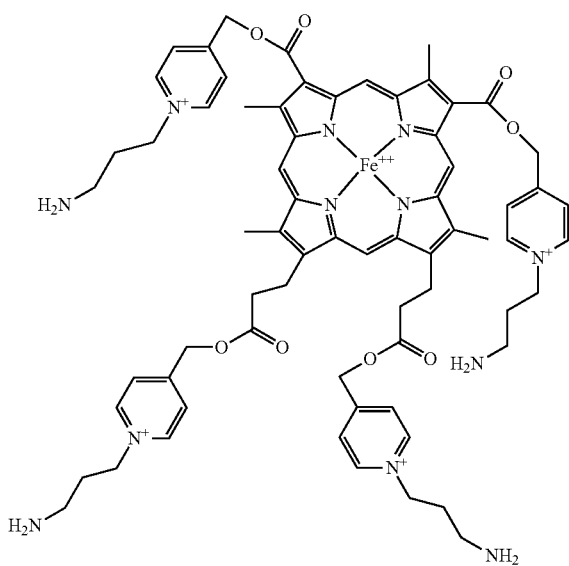

Amine-Functionalization of Chlorophyll

In some embodiments, the amine-functionalized porphyrin compound can be based on a Chlorophyll, such as Chlorophyll A, Chlorophyll B, Chlorophyll C1, Chlorophyll C2, Chlorophyll D, or Chlorophyll F. For example, in some embodiments, there is disclosed herein a compound, or a pharmaceutically acceptable salt or ester thereof, having a structure of one of:

Formula IV

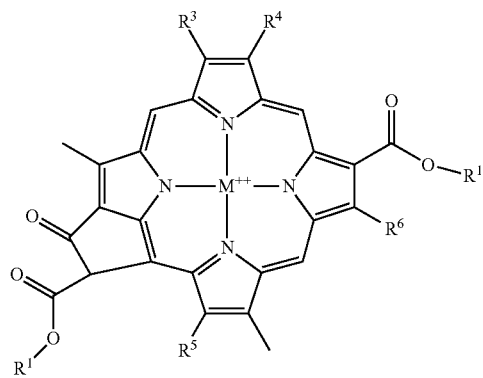

wherein $R^1$ independently comprises the structure:

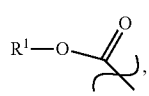

and
A is independently an optionally substituted N-heterocyclic aromatic ring; x is independently an integer from 0 to 6 (such as 0); $R^2$ is independently an aminoalkyl or an aminoaryl; wherein $R^3$, $R^4$, $R^5$, and $R^6$ are selected from one of:
(a) ethyl, methyl,

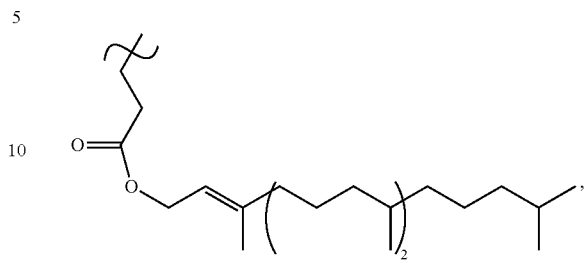

and methyl, respectively (Chlorophyll A, D);
(b) ethyl,

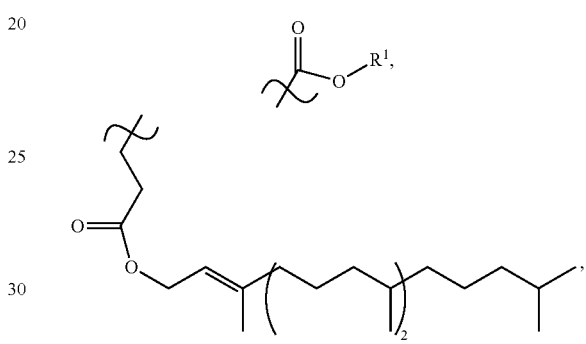

and methyl, respectively (Chlorophyll B);
(c) ethyl, methyl,

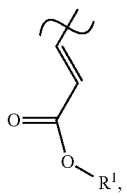

and methyl, respectively (Chlorophyll C1);
(d)

methyl,

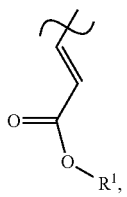

and methyl, respectively (Chlorophyll C2);
(e) ethyl, methyl,

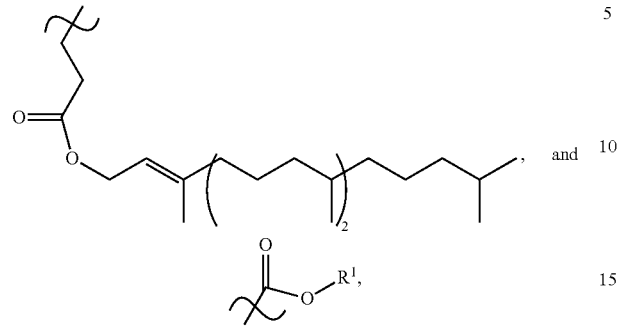

respectively (Chlorophyll F); and

M is a metal selected from the group consisting of manganese, iron, copper, cobalt, nickel, magnesium, and zinc, and optionally is not present. In embodiments where M is not present, the surrounding nitrogen atoms can be fully, partially, or not, hydrogenated. In several such embodiments, M is manganese. In some such embodiments, M is manganese. In additional such embodiments, M is magnesium. In more embodiments, M is iron. In some embodiments of Formula IV, A is independently an optionally substituted 4 to 7 membered N-heterocyclic aromatic ring. In some embodiments of Formula IV, A is independently an optionally substituted azetyl, an optionally substituted pyrrolyl, an optionally substituted pyridinyl, an optionally substituted azepinyl, or an optionally substituted azocinyl. In some embodiments of Formula IV, A is an optionally substituted pyridinyl.

In some embodiments of Formula IV,

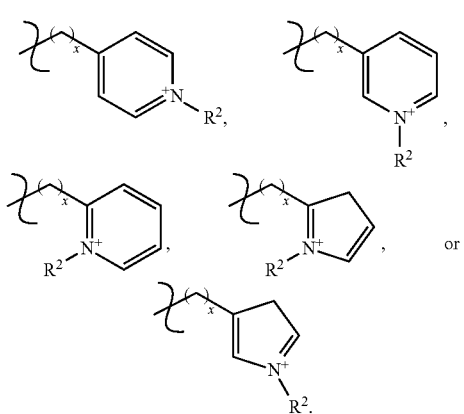

can be one of:

In several such embodiments, x can be 0 or 1.

In some embodiments of Formula IV, $R^2$ can be independently a lower aminoalkyl or lower aminoaryl. In some embodiments of Formula IV, $R^2$ can be aminoethyl. In some embodiments of Formula IV, $R^1$ is independently selected from one of:

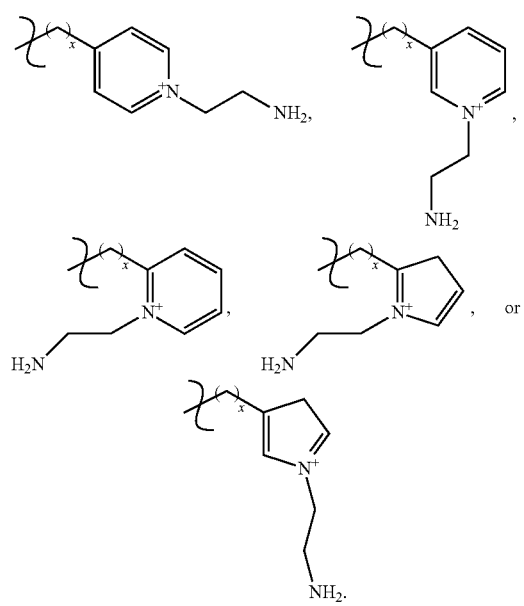

In several such embodiments, x can be 0 or 1.

In some embodiments of Formula IV, $R^2$ can be

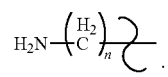

wherein n is from 0 to 10. For example, in some embodiments of Formula IV, $R^2$ can be any one of:

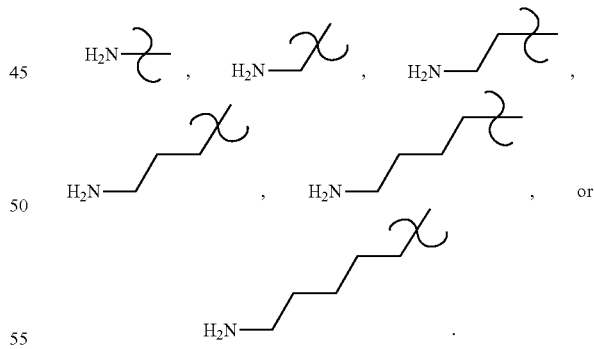

In some embodiments of Formula IV, $R^2$ can have a formula of

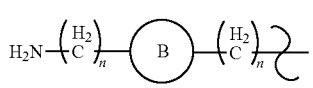

wherein n is independently 0 to 10 and B is selected from a 4 to 7 membered cycloaliphatic, optionally-substituted heterocycloaliphatic, optionally-substituted aryl, or optionally-substituted heteroaryl. In some embodiments of Formula IV, $R^2$ can have a formula of

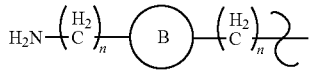

wherein n is independently 0 to 10 and B is selected from optionally-substituted pyrrolidine, optionally-substituted imidizolidine, optionally-substituted pryazolidine, optionally-substituted pyrrole, optionally-substituted diazole, optionally-substituted triazole, optionally-substituted piperidine, optionally-substituted pyridine, optionally-substituted diazine, optionally substituted triazine, optionally-substituted piperazine, optionally-substituted azepane, or optionally-substituted azepine.

In some embodiments of Formula IV, the compound can have a structure set forth as one of:

Structure 16

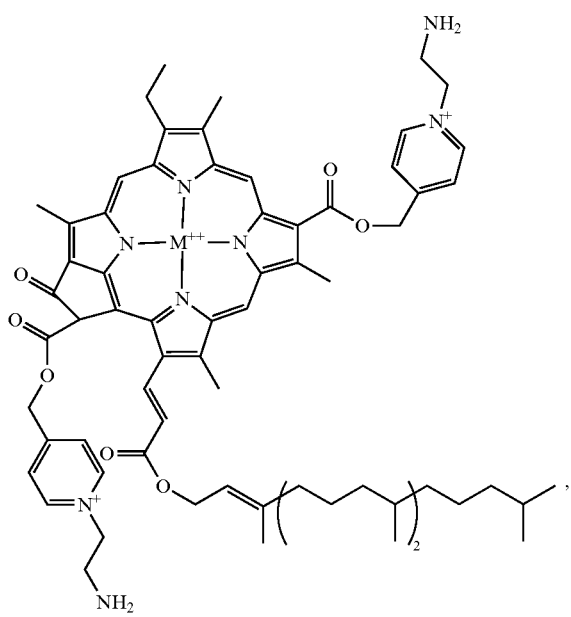

Structure 17

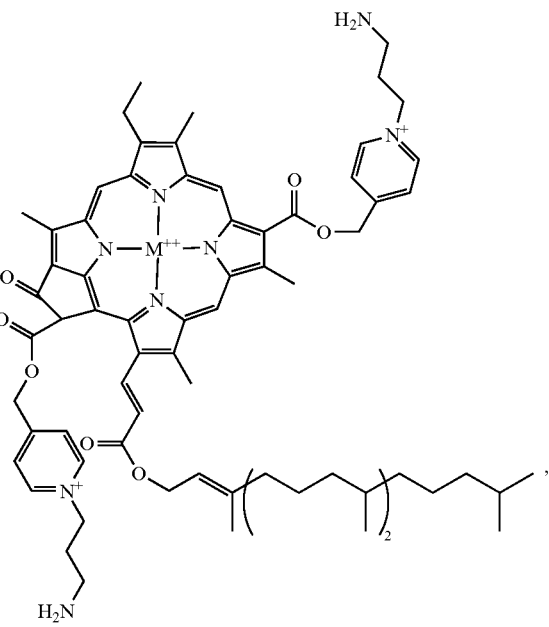

Structure 18

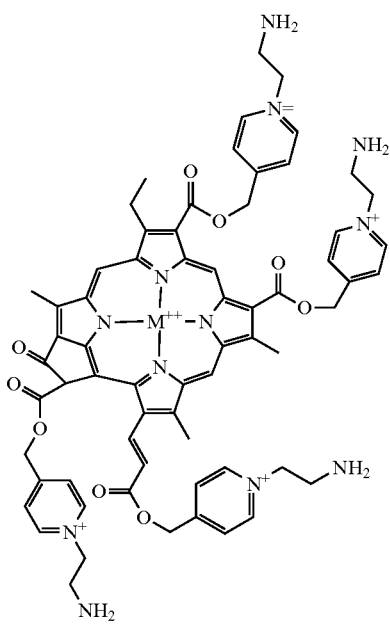

Structure 19
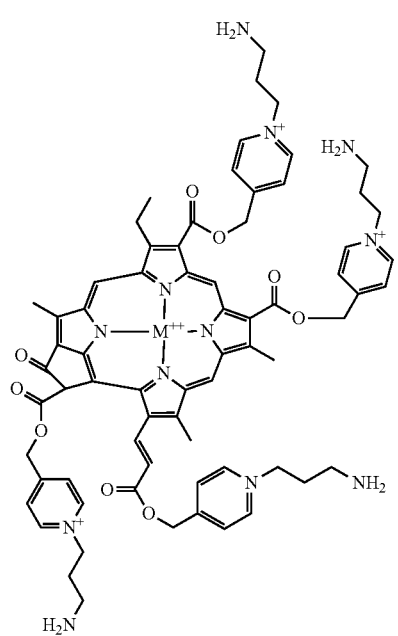
Structure 20
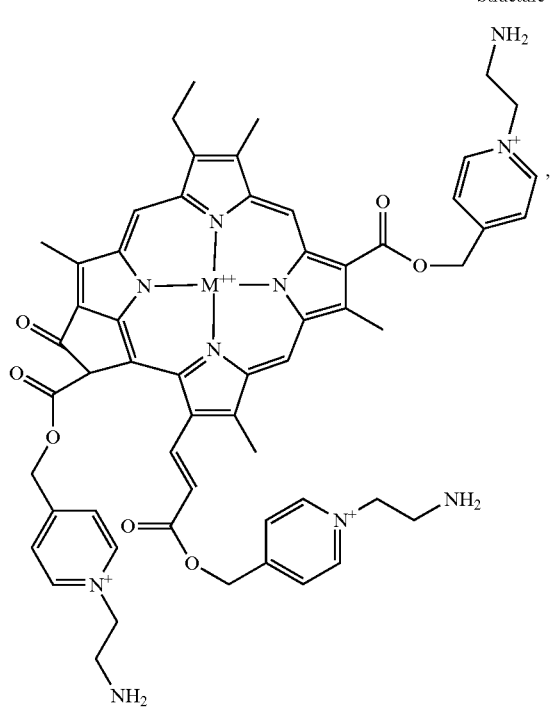
Structure 21
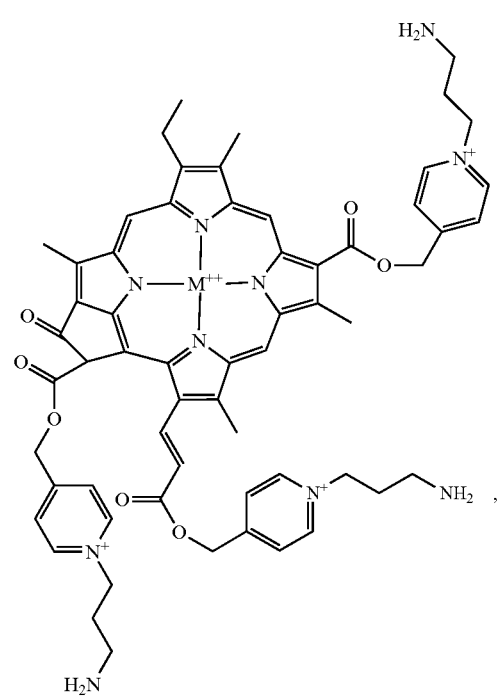
Structure 22
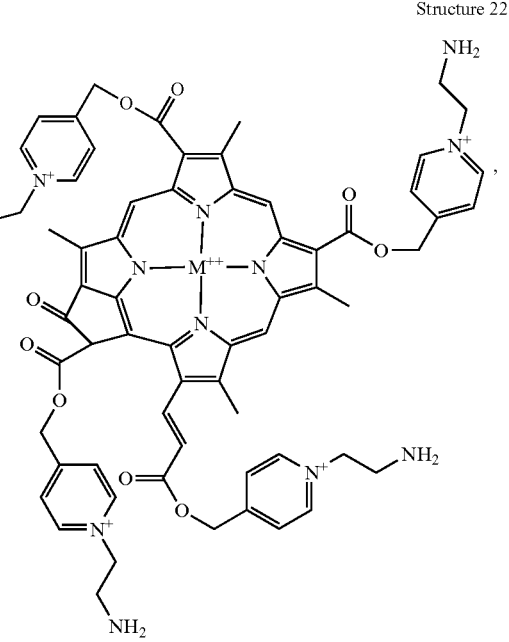

Structure 23
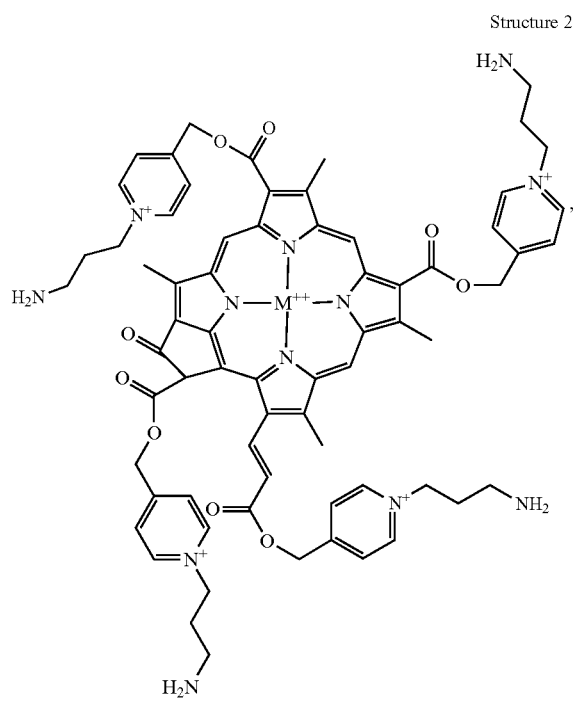
Structure 25
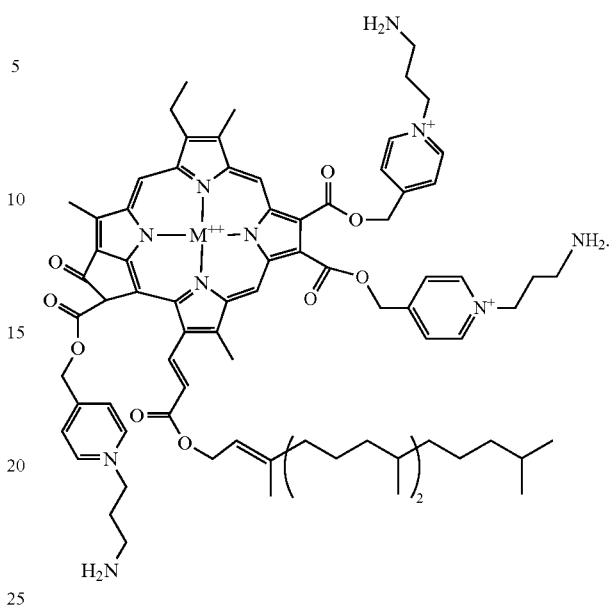
In some such embodiments of Formula IV, M can be magnesium. In some embodiments of Formula IV, the compound can have a structure set forth as one of:
Structure 24
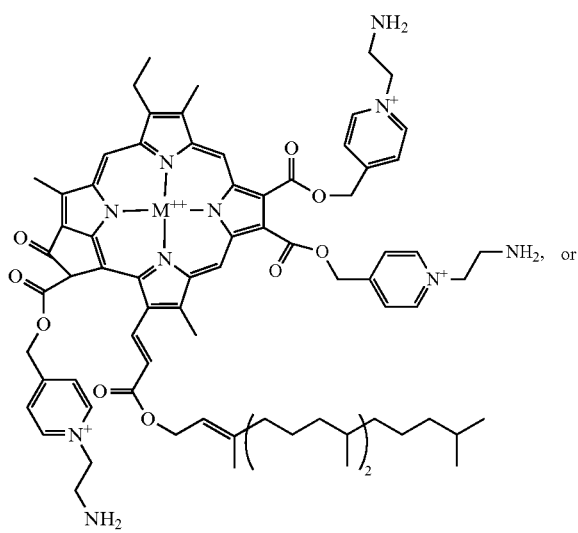
Structure 26
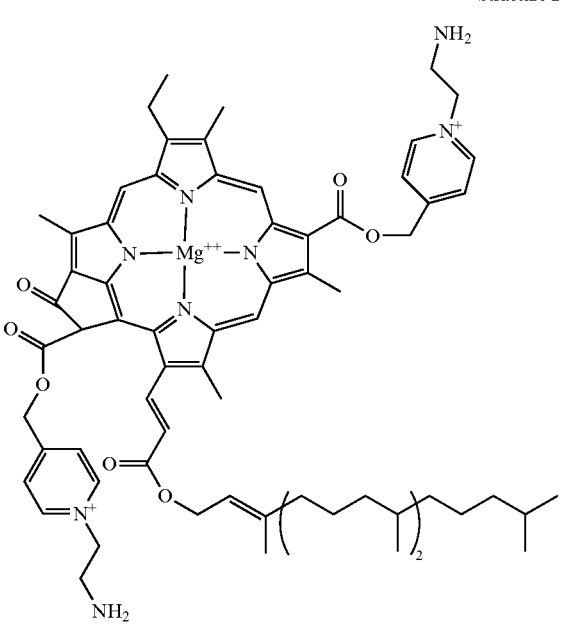

-continued
Structure 27
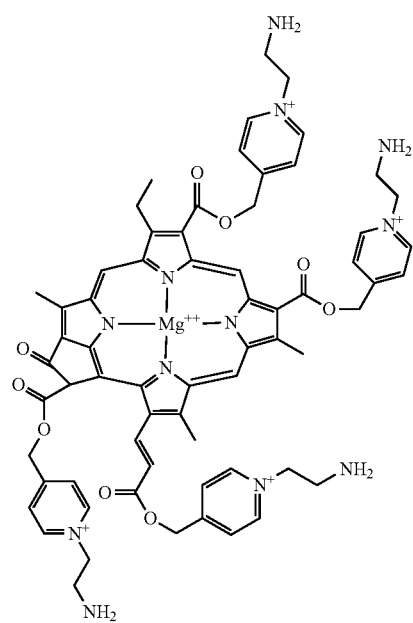
Structure 29
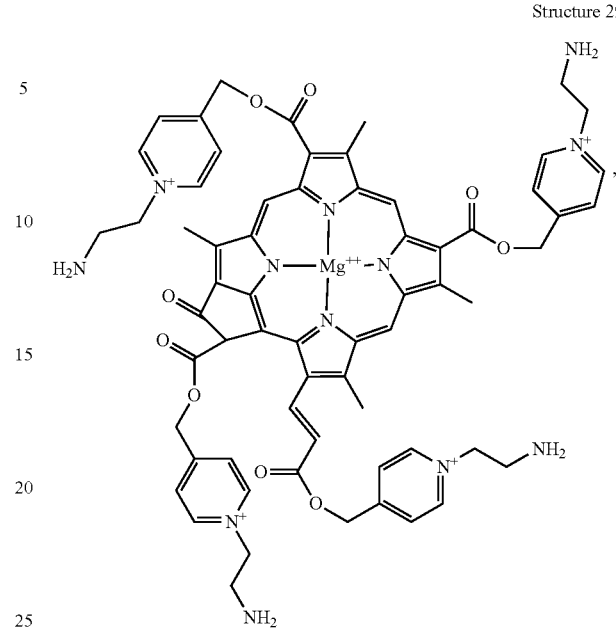
Structure 28
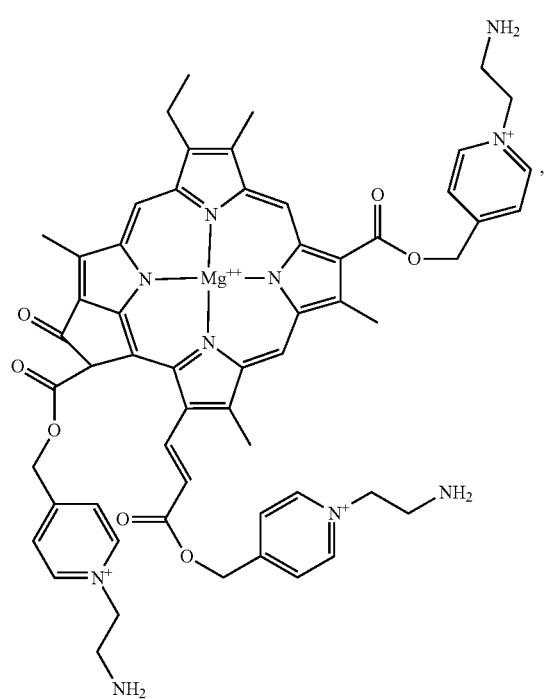
Structure 30
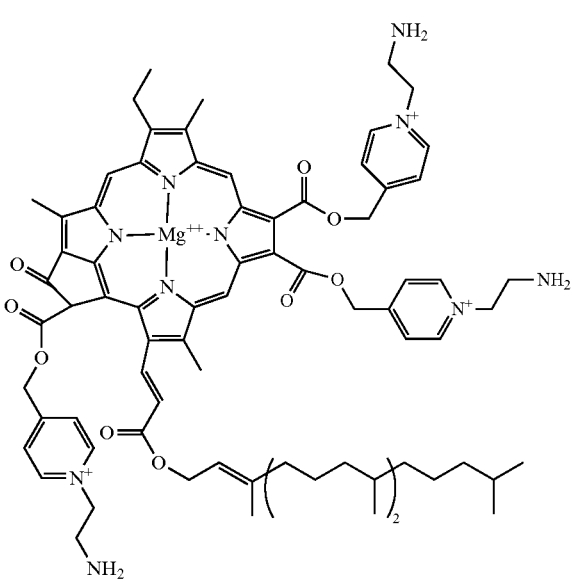

Structure 39

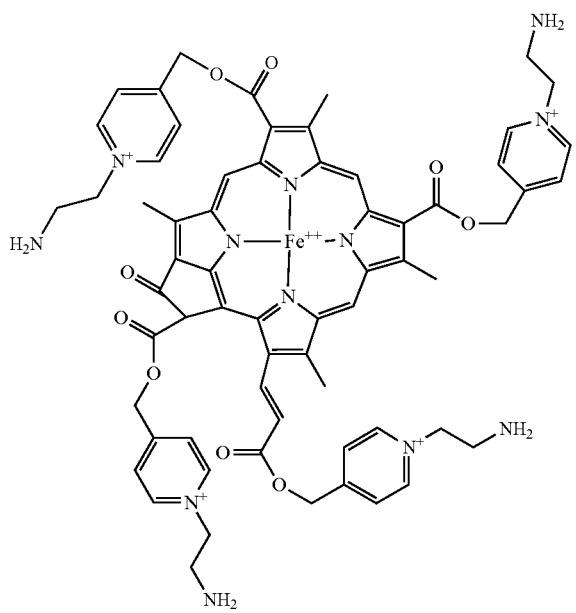

Amine Functionalization of Heme

In some embodiments, the amine-functionalized porphyrin compound can be based on a Heme, such as Heme A, Heme B, Heme C, or Heme O. For example, in some embodiments, there is disclosed herein a compound, or a pharmaceutically acceptable salt or ester thereof, having a structure of:

Formula V

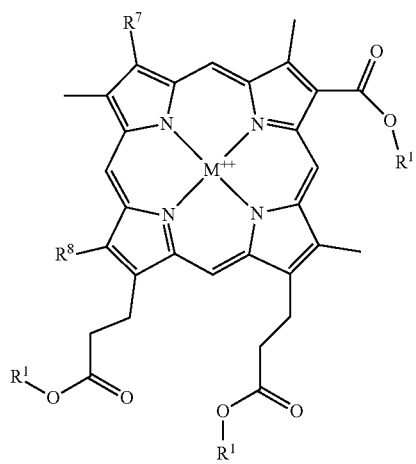

wherein $R^1$ independently comprises the structure:

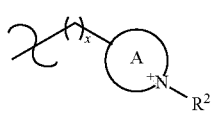

and A is independently an optionally substituted N-heterocyclic aromatic ring; x is independently an integer from 0 to 6 (such as 0); $R^2$ is independently an aminoalkyl or an aminoaryl; $R^7$ and $R^8$ are selected from one of:

(f)

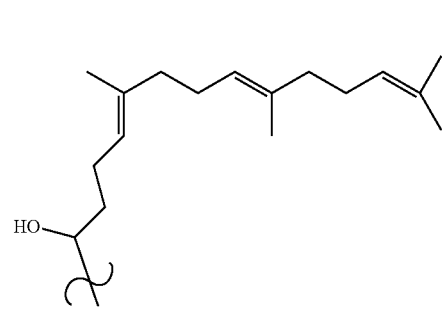

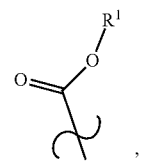

respectively (Heme A);

(g)

and methyl, respectively (Heme B);

(h)

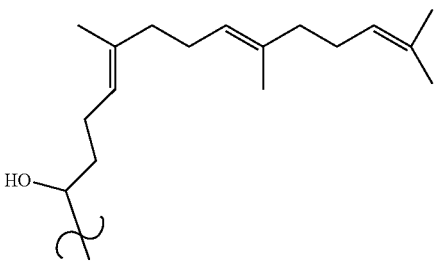 [SMILES: CC(C)=CCC/C(C)=C/CC/C(C)=C/CCC(C)O]

and methyl, respectively, (Heme O); and M is a metal selected from the group consisting of manganese, iron, copper, cobalt, nickel, magnesium, and zinc, and optionally is not present. In embodiments where M is not present, the surrounding nitrogen atoms can be fully, partially, or not, hydrogenated. In several such embodiments, M is manganese. In some such embodiments, M is manganese. In additional such embodiments, M is magnesium. In more embodiments, M is iron. In some embodiments of Formula V, A is independently an optionally substituted 4 to 7 membered N-heterocyclic aromatic ring. In some embodiments of Formula V, A is independently an optionally substituted azetyl, an optionally substituted pyrrolyl, an optionally substituted pyridinyl, an optionally substituted azepinyl, or an optionally substituted azocinyl. In some embodiments of Formula V, A is an optionally substituted pyridinyl. In some embodiments of Formula V, the compound can have a structure set forth as:

In some embodiments of Formula V,

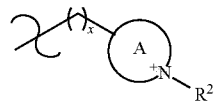

can be one of:

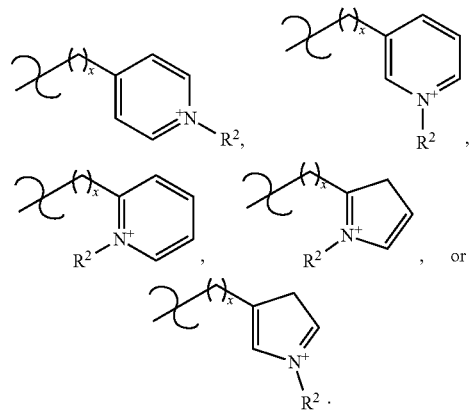

In several such embodiments, x can be 0 or 1.

In some embodiments of Formula V, $R^2$ can be independently a lower aminoalkyl or lower aminoaryl. In some embodiments of Formula V, $R^2$ can be aminoethyl. In some embodiments of Formula V, $R^1$ is independently selected from one of:

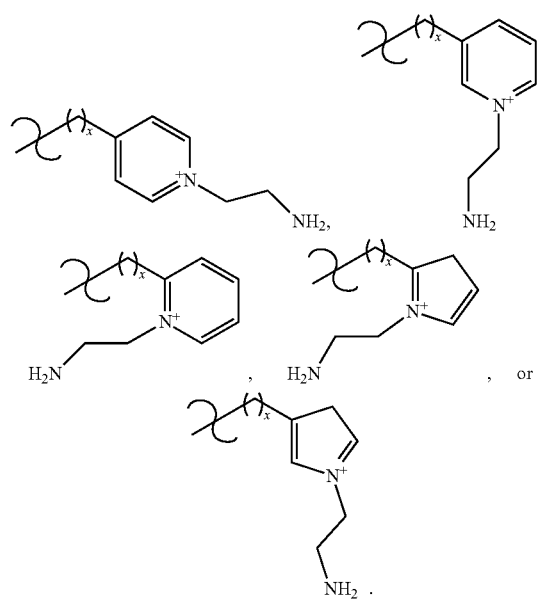

In several such embodiments, x can be 0 or 1.

In some embodiments of Formula V, $R^2$ can be

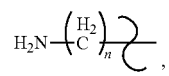

wherein n is from 0 to 10. For example, in some embodiments of Formula V, $R^2$ can be any one of:

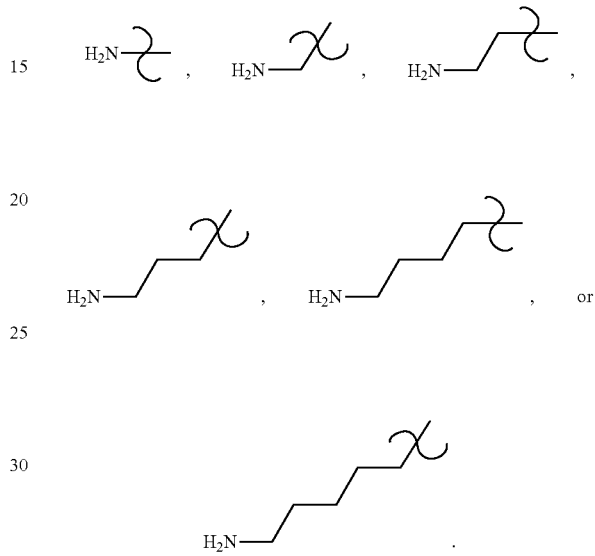

In some embodiments of Formula V, $R^2$ can have a formula of

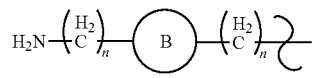

wherein n is independently 0 to 10 and B is selected from a 4 to 7 membered cycloaliphatic, optionally-substituted heterocycloaliphatic, optionally-substituted aryl, or optionally-substituted heteroaryl. In some embodiments of Formula V, $R^2$ can have a formula of

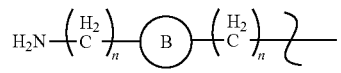

wherein n is independently 0 to 10 and B is selected from optionally-substituted pyrrolidine, optionally-substituted imidizolidine, optionally-substituted pryazolidine, optionally-substituted pyrrole, optionally-substituted diazole, optionally-substituted triazole, optionally-substituted piperidine, optionally-substituted pyridine, optionally-substituted diazine, optionally substituted triazine, optionally-substituted piperazine, optionally-substituted azepane, or optionally-substituted azepine.

In some embodiments of Formula V, the compound can have a structure set forth as one of:
Structure 31
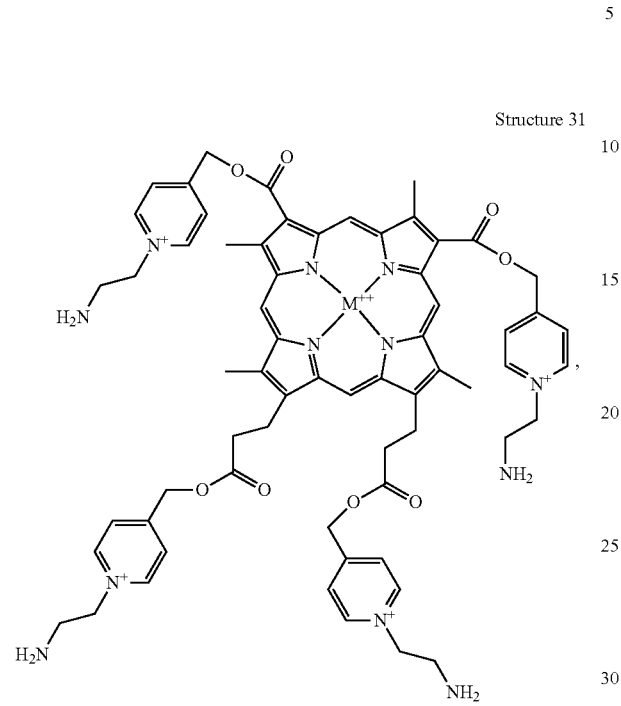
Structure 32
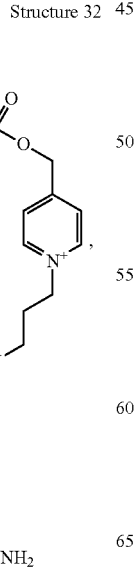
Structure 33
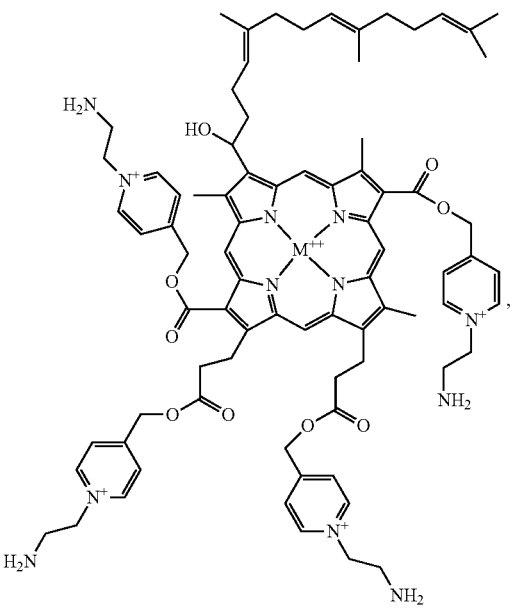
Structure 34
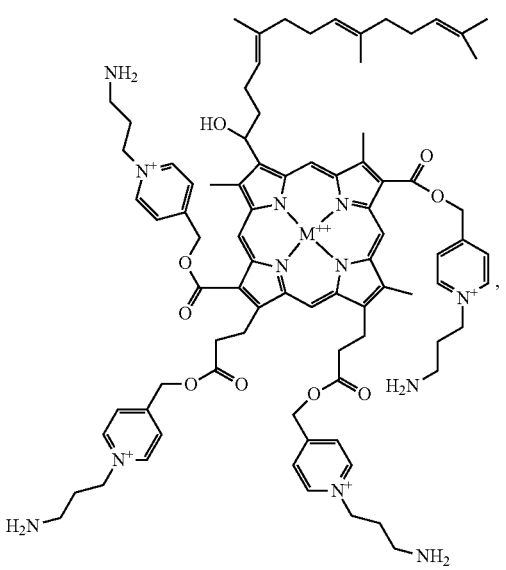

-continued

Structure 35
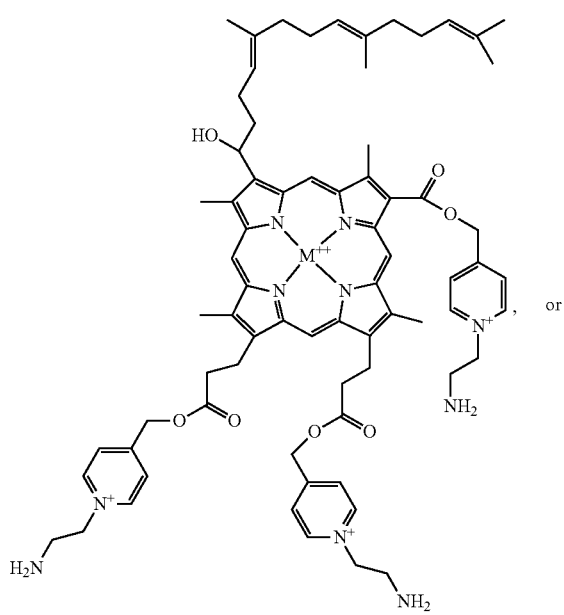

Structure 36
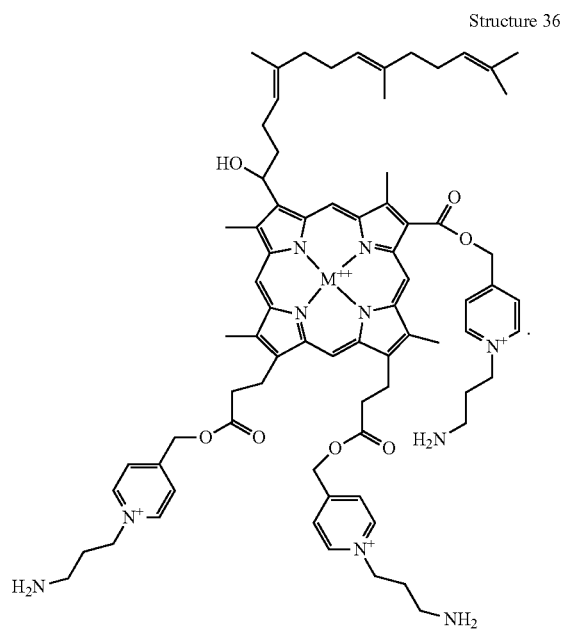

In some such embodiments of Formula V, M can be iron. In additional embodiments of Formula V, M can be manganese.

In some embodiments of Formula V, the compound can have a structure set forth as one of:

Structure 37
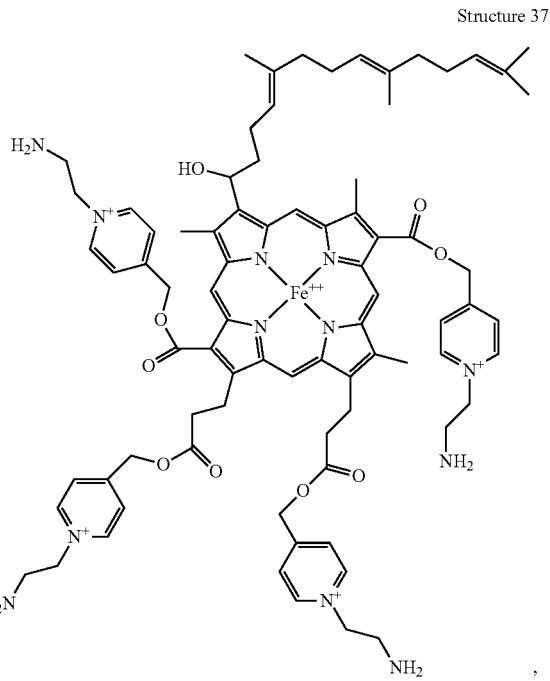

Structure 38
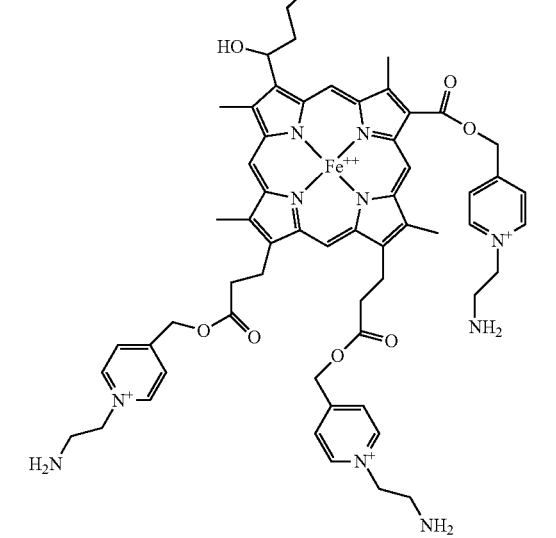

FIG. 1 depicts an exemplary synthesis method for making an embodiment of the amine-functionalized porphyrin compounds disclosed herein according (for example, according to Formula I). In FIG. 1, a method of converting a commercially available non-amine functionalized porphyrin (meso-Tetra(2-pyridyl) porphine) to an amine-functionalized porphyrin is shown. The synthesis procedure involves dissolving the non-amine functionalized porphyrin (such as meso-Tetra(2-pyridyl) porphine) in organic solvent (such as dimethylformamide (DMF) or dimethyl sulfoxide (DMSO)) with a molar excess of a primary amine donor (such as an ethylamine donor, for example, 2-bromoethylamine) under conditions for addition of the primary amine to the porphyrin. Following the amine-functionalization, a metal atom (such as manganese) can be added to the porphyrin by incubation with a molar excess of an appropriate metal ion donor under acidic conditions. As shown in FIG. 1, in some embodiments, the amine-functionalized porphyrin can be converted to a manganese-containing porphyrin by incubation with a molar excess of $MnCl_2$ in organic solvent (such as DMF) at high pH (such as pH 12). The resulting porphyrin can be further processed, for example, by precipitation with tetrahydrofuran, and washing with diethyl ether, and purified as needed.

Figure 13:
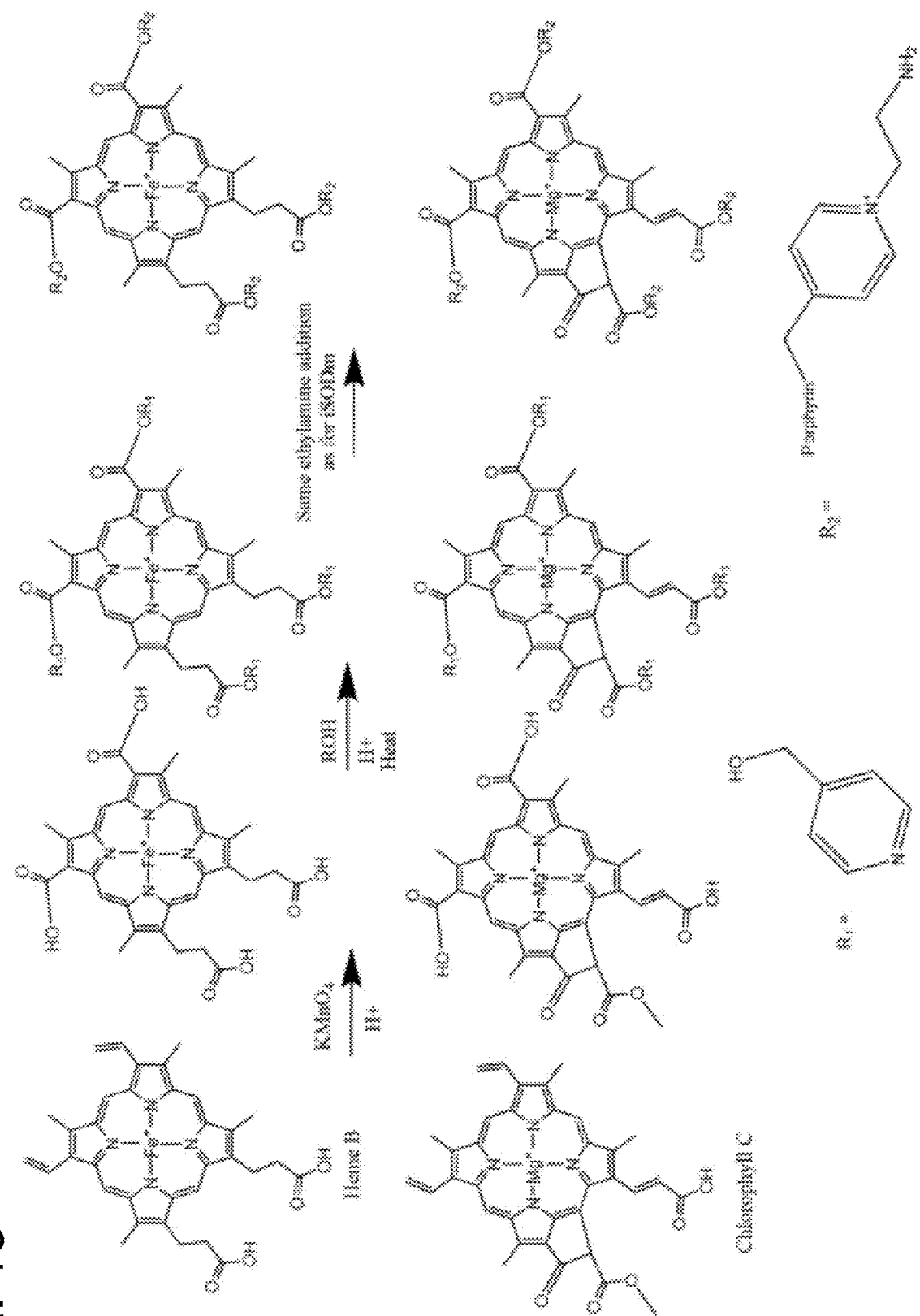
FIG. 13 is a diagram illustrating chemical modification of Heme B and Chlorophyll $C_2$ to generate amine-functionalized porphyrins based on these naturally occurring compounds.
Figure 15:
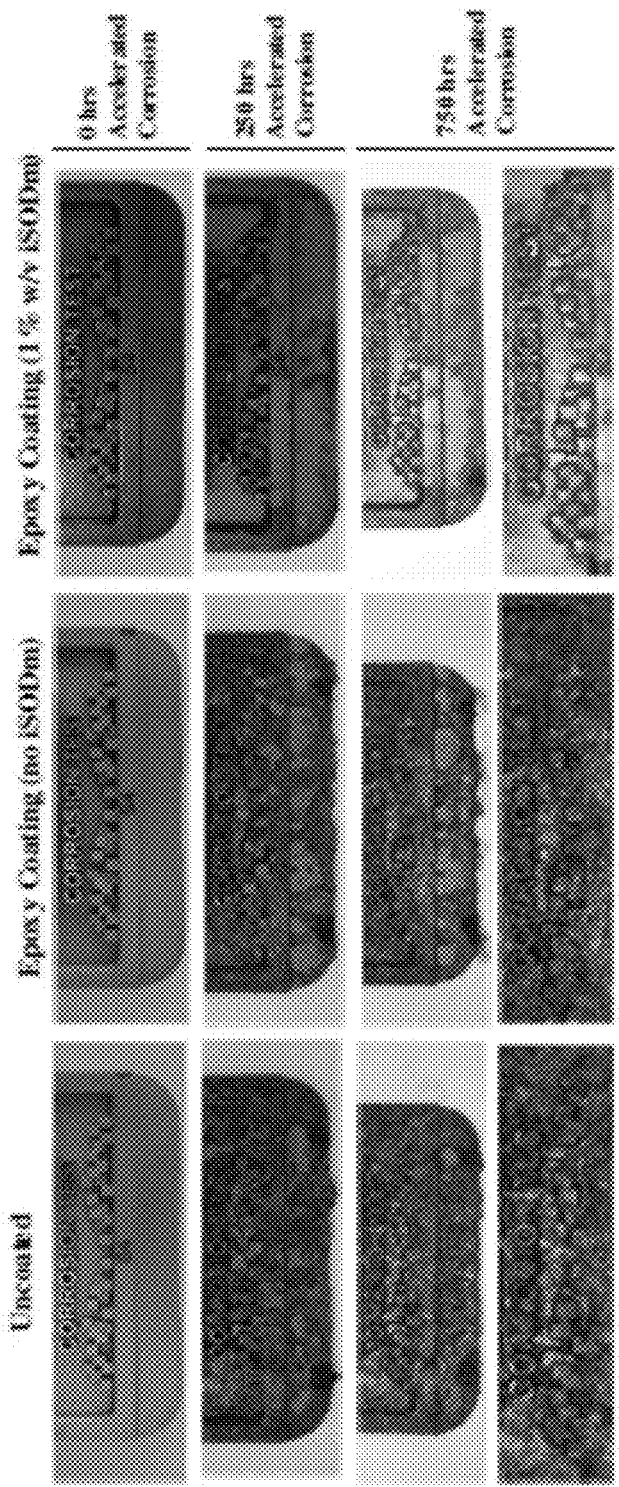
FIG. 15 is a set of digital images illustrating that an epoxy coating containing iSODm reduces corrosion of metal stainless steel bronze 3D printed substrates. 3D printed samples of stainless steel and bonze were coated with epoxy Araldite® 506 using Ethyleneamine curing agent with and without iSODm at 1% w/v. Samples that were untreated, coated with epoxy lacking iSODm, or epoxy with iSODm were subjected to corrosion testing in an ASTM B117 corrosion test chamber. After 250 hours and 750 hours accelerated corrosion in the test chamber, the resolution of text and images on the samples was substantially more clear on the epoxy/iSODm-coated samples than uncoated samples or samples coated with epoxy alone.

FIG. 13 illustrates an exemplary synthesis method for making an embodiment of the amine-functionalized porphyrin compounds disclosed herein. The formation of carboxylic acid functional groups at target terminal alkene sites occurs via the $KMnO_4$ oxidation under acidic conditions. The vinyl porphyrin molecules were dissolved in a mixture of methylene chloride, acetic acid, and water (5:1:4 v/v/v). Following the addition of the phase transfer agent (dimethyl polyethylene glycol) the solution was cooled using an ice bath. Four molar equivalents of potassium permanganate were added over the period of 1 hour, and the reaction was stirred for 6 hours, while maintaining a cooled ice bath. Excess oxidant was removed with sodium bisulfite and the reaction was acidified with concentrated HCl.

Esterification of carboxylic acid groups and transesterification of ester groups on the porphyrins were carried out under a single step Fischer esterification process. In brief the porphyrin is reacted with molar excess ROH (~20×) where R=N-heterocylic aromatic ring. The reactions is kept under reflux conditions in the presence of catalytic amount of sulfuric acid for 8-24 hour until the reaction is completed.

The aminoalkyl/aminoaryl substitution of the N-heterocyclic ring, as well as the metalation or transmetallation of the porphyrin complexes can be accomplished using is as described for the functionalization of the iSODm.

In some embodiments, a pharmaceutically acceptable salt or ester of a disclosed amine functionalized porphyrin is provided. The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include C1-C22 fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

In several embodiments, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Protected derivatives of the disclosed amine functionalized porphyrin compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

In some embodiments, the amine-functionalized porphyrin (such as iSODm) can be included in a composition, such as a composition including an anti-fouling compound. Non-limiting examples of anti-fouling compounds that can be included in the composition with the amine-functionalized porphyrin include heterocyclic and aromatic-based anti-fouling compounds, such as Igarol and/or Paraquat.

III. Applications

The disclosed amine-functionalized porphyrin compounds can be used to impart antioxidant, anti-inflammatory, anti-microbial, and/or cell-adhesion specificity to any surface or material in need thereof. In exemplary embodiments, an effective amount of a disclosed amine-functionalized porphyrin compound can be incorporated into or coated onto a surface of a medical implant, or a marine surface. In additional embodiments, an effective amount of a disclosed amine-functionalized porphyrin compound can be incorporated into a material of interest, such as an epoxy, a hydrogel, a nylon polymer, and/or an acrylate material. Additional description concerning exemplary applications of the disclosed amine-functionalized porphyrin compounds is provided below.

A. Medical Implants

In several embodiments, the amine-functionalized porphyrin can be included in or on a medical implant. For example, the medical implant can include one or more surfaces coated with or linked to an amount of the amine-functionalized porphyrin that is effective to reduce oxidation around the implant, or the implant can be constructed of a material containing an amount of the amine-functionalized porphyrin that is effective to reduce oxidation around the implant.

In some embodiments, the amine-functionalized porphyrin compound can be included on or in a medical implant designed for full or partial implantation into a subject, such as any mammal, including humans, non-human primates, pigs, sheep, cows, rodents and the like.

The medical implant can be any medical implant that would benefit from having an antioxidant compound on a surface that contacts a tissue in a subject. For example, the medical implant can be a dental implant, a heart valve, a vascular stent, a neural implant, an electoral lead, a neural probe for recording and/or stimulating a neural signal in a subject, and/or a medical catheter.

In some embodiments, the implant can be in the form of a screw, a plate, a nail, a pin, and specially formed parts and may be used as prostheses in medicine, more specifically in orthopedics, for replacing or strengthening broken or diseased bones, and in dentistry, for anchoring artificial teeth and for anchoring of bone anchored hearing prosthesis into the skeletal structure of humans and animals.

In some embodiments, the medical implant includes a metallic surface that can be coated with the amine-functionalized metalloporphyrin. The metallic surface can be made, for example, from titanium or a titanium alloy (for example, nitinol), such as an alloy of titanium and chromium, niobium, tantalum, vanadium, zirconium, aluminum, cobalt, nickel, and/or stainless steels.

In some embodiments, the effective amount of the amine-functionalized porphyrin can reduce inflammation around the medical implant, for example by at least 10%, at least 20%, at least 30%, at least 40%, at least 50%, at least 60%, at least 70%, at least 80%, at least 90%, or at least 100% compared to a control medical implant lacking the amine-functionalized porphyrin.

In some embodiments, the effective amount of the amine-functionalized porphyrin can reduce inflammation around the medical implant after it is implanted into a subject, for example by about 10%, about 20%, about 30%, about 40%, about 50%, about 60%, about 70%, about 80%, about 90%, or about 100% compared to a control medical implant lacking the amine-functionalized porphyrin.

In some embodiments, the effective amount of the amine-functionalized porphyrin can reduce the density of inflammatory cells around the medical implant after it is implanted into a subject, for example by about 10%, about 20%, about 30%, about 40%, about 50%, about 60%, about 70%, about 80%, about 90%, or about 100% compared to a control medical implant lacking the amine-functionalized porphyrin. In some embodiments, the effective amount of the amine-functionalized porphyrin can increase the density of non-inflammatory cells around the medical implant after it is implanted into a subject, for example by about 10%, about 20%, about 30%, about 40%, about 50%, about 60%, about 70%, about 80%, about 90%, or about 100% compared to a control medical implant lacking the amine-functionalized porphyrin.

In some embodiments, the effective amount of the amine-functionalized porphyrin can reduce biofilm accumulation (such as accumulation of microorganisms, for example bacteria) around the medical implant (such as an indwelling catheter), for example by about 10%, about 20%, about 30%, about 40%, about 50%, about 60%, about 70%, about 80%, about 90%, or about 100% compared to a control medical implant lacking the amine-functionalized porphyrin.

In some embodiments, the effective amount of amine-functionalized porphyrin compound on the surface of the medical implant includes from about 0.1 $ng/mm^2$ to about 20 $ng/mm^2$, such as from about 0.1 $ng/mm^2$ to about 0.5 $ng/mm^2$, from about 0.1 $ng/mm^2$ to about 1 $ng/mm^2$, from about 0.1 $ng/mm^2$ to about 5 $ng/mm^2$, from about 0.1 $ng/mm^2$ to about 10 $ng/mm^2$, from about 1 $ng/mm^2$ to about 5 $ng/mm^2$, from about 1 $ng/mm^2$ to about 10 $ng/mm^2$, from about 1 $ng/mm^2$ to about 20 $ng/mm^2$, from about 5 $ng/mm^2$ to about 10 $ng/mm^2$, from about 5 $ng/mm^2$ to about 20 $ng/mm^2$, or from about 10 $ng/mm^2$ to about 20 $ng/mm^2$.

Methods of determining the amount of amine-functionalized porphyrin on the exterior surface of the medical implant or other surface are known in the art, for example, using analytical X-ray Photoelectron Spectroscopy analysis (XPS) or nuclear magnetic resonance (NMR) assays.

Any appropriate method can be used to linking and/or coating the amine functionalized porphyrin compound to the external surface of the medical implant. Non-limiting examples include coating methods such as dipping, spraying, painting, vacuum deposition, conjugation to the external surface of the implant (e.g., by conjugation to hydroxyl or carboxyl groups on the external surface of the implant, or coating applied to the implant), or by any other method known to those of ordinary skill in the art.

In several embodiments, a surface on the medical implant can be modified or selected to have one or more functional groups (such as hydroxyl or carboxyl groups) that can be covalently linked to a primary amine group on the amine functionalized porphyrin compound. In some embodiments, silane chemistry and a GMBS crosslinker can be used to covalently attach the amine-functionalized porphyrin to the surface on the medical implant (for example, an implant with a glass surface). In additional embodiments, air plasma or plasma oxygen can be used to add polar hydroxyl groups to the surface of the medical implant, which can be then be covalently attached to primary amine functional groups (for example, via a crosslinker) on the amine-functionalized porphyrin to the surface on the medical implant. In an additional approach, treatment with succinic anhydride adds carboxylic acid groups to the surface of the medical implant, which can be then be covalently attached to primary amine functional groups on the amine-functionalized porphyrin (for example, via a crosslinker) to the surface on the medical implant. In further embodiments, treatment with polyethylenedioxythiophene (PEDOT) doped with graphene oxide (GO) adds carboxylic acid groups to the surface of the medical implant, which can be then be covalently attached (for example, via a crosslinker) to primary amine functional groups on the amine-functionalized porphyrin to the surface on the medical implant. In additional embodiments, the surface of the medical implant can be treated or coated with poly(acrylic acid) (PAA) and the amine-functionalized porphyrin can be covalently attached (for example, via a crosslinker to the carboxyl functional groups of the (PAA), resulting in a stable and soluble amine-functionalized porphyrin-polymer conjugate. Methods of conjugating primary amine containing compounds (such a peptide) to a solid support or surface are described, e.g., in Luo et al., J Mat. Chem. B, 2013. 1(1): p. 1340-1348; Azemi et al., Acta Biomaterialia, 2008. 4(5): p. 1208-1217; Chang et al., Langmuir, 2007. 23(23): p. 11718-25; Sia and Whitesides, Electrophoresis, 2003. 24(21): p. 3563-76; Zhang et al., Acta Biomater, 2011. 7(10): p. 3746-56; each of which is incorporated by reference herein in its entirety).

Dental Implants

In some embodiments, the medical implant is a dental implant coated with or made of a material containing an effective amount of a disclosed amine-functionalized metalloporphyrin. For example, the amine-functionalized porphyrin can be included in or on an external surface of the dental implant (such as a dental post) in any configuration that exposes the amine-functionalized porphyrin to tissue surrounding the implant when implanted in a subject. The effective amount of amine-functionalized porphyrin compound included in or on the dental implant can vary depending on the particular application.

Non-limiting examples of methods that can be used to apply the amine-functionalized porphyrin to the external surface of the dental implant include coating methods such as dipping, spraying, painting, vacuum deposition, conjugation to the external surface of the implant (e.g., by conjugation to hydroxyl or carboxyl groups on the external surface of a dental implant, or coating applied to the dental implant), or by any other method known to those of ordinary skill in the art. In some embodiments, the amine-functionalized porphyrin can be included in a composition used to partially or fully coat the dental implant.

The dental implant can be any medical implant intended to be implanted into the oral cavity of a vertebrate animal, in particular a mammal such as a human, such as in tooth restoration procedures. Generally, a dental implant is composed of one or several implant parts. For instance, a dental implant can include a dental fixture (such as a dental post) coupled to secondary implant parts, such as an abutment and/or a dental restoration such as a crown, bridge or denture.

In some embodiments, the dental implant can have reduced biofilm accumulation over time, such as over a year, when implanted into a subject. In some embodiments, the dental implant can have improved tissue integration (that is, there is improved tissue adherence to the implant) compared to dental implants that lack the amine-functionalized porphyrin when implanted into a subject. For example, the dental implant can have increased tissue integration with a hard and/or mineralized tissue, such as cartilage, bone, dental enamel, dentin, dental hard tissue, and dental cortical tissue. In additional embodiments, the tissue surrounding the dental implant following implantation can have a reduced concentration of inflammatory cells.

In some embodiments, an effective amount of amine-functionalized porphyrin compound is an amount of the amine-functionalized porphyrin compound (e.g., a surface density of amine-functionalized metalloporphyrin) sufficient to reduce biofilm accumulation on the implant over time (for example over a year) observed with a corresponding dental implant that is not conjugated to an effective amount of antioxidant compound.

In some embodiments, the exterior surface of the dental implant includes an amount of amine-functionalized porphyrin compound effective to reduce biofilm accumulation (such as by at least 10%, at least 20%, at least 30%, at least 40%, at least 50%, at least 60%, at least 70%, at least 80%, at least 90%, or more) over time (such as over one week, one month, six months, one year, two years, or more) compared to a dental implant without the amine-functionalized metalloporphyrin.

In some embodiments, the exterior surface of the dental implant includes an amount of amine-functionalized porphyrin compound effective to reduce the concentration of inflammatory cells proximal (such as within 100 µm) to the implant (such as by at least 10%, at least 20%, at least 30%, at least 40%, at least 50%, at least 60%, at least 70%, at least 80%, at least 90%, or more) over time (such as over one week, one month, six months, one year, two years, or more) compared to a dental implant without the amine-functionalized metalloporphyrin.

Neural Implants

In some embodiments, the medical implant is a neural implant coated with or made of a material containing an effective amount of a disclosed amine-functionalized metalloporphyrin. For example, the amine-functionalized porphyrin can be included in or on an external surface of the neural implant (such as a probe on the neural implant) in any configuration that exposes the amine-functionalized porphyrin to tissue surrounding the implant when implanted in a subject. Non-limiting examples of methods that can be used to apply the amine-functionalized porphyrin to the external surface of the neural implant include coating methods such as dipping, spraying, painting, vacuum deposition, conjugation to the external surface of the neural implant (e.g., by conjugation to an insulating layer on the surface of the neural implant, such as a paralyne C insulating layer), or by any other method known to those of ordinary skill in the art. In another embodiment, the amine-functionalized porphyrin can be included in a composition used to make the insulating layer of the neural implant, and the composition can be applied thereon (e.g., using coating methods) to form the insulating layer of the neural implant.

Numerous types and styles of neural implants including one or more electrodes for recording and/or stimulating a neural signal are available, and known to the person of ordinary skill in the art. Any neural implant for recording and/or stimulating neural signals in a subject may be used with the disclosed embodiments. In several embodiments, the neural implant includes more than one electrode, such as an array of electrodes. In additional embodiments, a device is provided that can include one or more probes, each of which can include one or more electrodes. Non-limiting examples include deep brain stimulators, EcoG grids, electrode arrays, microarrays (e.g., Utah and Michigan microarrays), and microwire electrodes and arrays. Neural implants (and devices including them) can be inserted into the body, for example transcutaneously, intervertebally, or transcranially, to a target site in the body (for example, in the brain) where neural signals are to be recorded or stimulated. Commercial sources of neural implants and devices for recording and/or stimulating neural signals in a subject, including implants coated with an insulating layer (such as Parylene C), are known. For example, such electrodes and devices are available commercially from Blackrock Microsystems (Salt Lake City, Utah) and NeuroNexus (Ann Arbor, Mich.).

The effective amount of amine-functionalized porphyrin compound can vary depending on the particular application. In some embodiments, an effective amount of amine-functionalized porphyrin compound is an amount of the amine-functionalized porphyrin compound (e.g., a surface density of amine-functionalized metalloporphyrin) sufficient to reduce the deleterious effects on neural recording quality over time (for example over a year), observed with a corresponding electrode that is not conjugated to an effective amount of antioxidant compound. In additional embodiments, an effective amount of amine-functionalized porphyrin compound includes an amount of amine-functionalized porphyrin compound on the exterior surface of the neural implant sufficient to allow recording of at least four sortable neural units from at least one electrode after the probe has been implanted for at least six months.

In some embodiments use of the disclosed neural implant (or device including the neural implant) allows for an increase in the recorded neural signal over time. For example, in some embodiments, use of the disclosed neural implant (or device including the neural implant) allows for an increase in the total number of sortable neural units over time; for example, an increase of at least 10%, 20%, 30%, 40%, 50%, 60%, 70%, 80%, 90%, or 100% or more of an increase in total number of sortable neural recording units over time. In some embodiments, use of the disclosed neural implant (or device including the neural implant) allows for an increase in the average number of sortable neural units per channel of the neural implant over time; for example, an increase of at least 10%, 20%, 30%, 40%, 50%, 60%, 70%, 80%, 90%, or 100% or more of an increase in the average number of sortable neural recording units per channel of the neural implant over time. In some embodiments the increase over time is measured at 4 weeks post implantation compared to 20 weeks post implantation.

Methods of identifying neural recording units in data recorded from an electrode (or array of electrodes) implanted in a subject are known to the person of ordinary skill in the art (see, e.g., Lewicki, "A review of methods for spike sorting: the detection and classification of neural action potentials," Network: Comput. Neural Syst., 9, R53-R78, 1998, which is incorporated by reference herein in its entirety). In some embodiments, raw neural recording data is first band passed filtered between 300 Hz to 10 kHz. Following data filtering, waveforms that cross the TDT automatic threshold are selected for further spike sorting analysis. Hoop-based spike discrimination is carried out online as the experimenter selects time-voltage windows based on waveform shape. Waveforms that fall within this selected window are classified as belonging to the same sort. Manual inspection of the sorted units in principal component analysis space is used to assess the appropriateness of the selected windows. Online spike sorting progresses by relying upon template matching to properly sort units that fall into one of the above mentioned time-voltage windows.

In several embodiments, a disclosed neural implant can be used for chronic recording and/or stimulation of neural signals from a subject. For example the neural implant can be implanted into neuronal tissue of the subject, and used to record and/or stimulate neural signals from the subject for a period of at least 1 month (such as at least 2, 6, 12, 18, 24, 30 or 36 or more months) without deterioration of quality or quantity of the recorded or stimulated neural signal.

The neural implant is typically linked to circuitry for recording and/or stimulating a neural signal via the one or more electrodes included on the implant. The person of ordinary skill in the art is familiar with circuitry for use with the disclosed devices. In some embodiments, the integrated circuits can be fully implanted (typically implantable in a subcutaneous pocket within a patient's body) or partially implanted in the patient, but are not limited thereto. The operable linkage to the neural implant or device can be by way of one or more leads, although any operable linkage capable of transmitting the measured neural signal from the electrodes to the circuitry, or a stimulation signal from the circuitry to the electrodes, can be used.

B. Epoxy

In some embodiments, an amine-functionalized porphyrin can be incorporated into an epoxy to generate an epoxy with anti-oxidative properties.

An exemplary procedure for making an epoxy including an amine-functionalized porphyrin is provided in Example 4. The amine-functionalized porphyrin (such as iSODm) can be included in any epoxy based on epoxy resins that can be crosslinked using a primary-amine containing curing agent. The ratio of the amine-functionalized porphyrin to epoxy resin, curing time, and need for additional curing agents may be altered as needed. The benefits of including the amine-functionalized porphyrin compound in the epoxy include (but are not limited to), improved curing time, improved mechanical properties, improved corrosion resistance (such as resistance to oxidative corrosion), and improved antioxidant properties.

For example, by adding the iSODm with four primary amines that can react with the epoxide groups the curing time is decreased compared to epoxy polymers formed with curing agents having only two amine reactive groups. Further, the ability of the amine-functionalized porphyrin to react with four different epoxide groups increases the amount of crosslinking in the epoxy polymer, thereby improving the mechanical properties, such as stiffness.

In some embodiments, the amine-functionalized porphyrin (such as iSODm) can be included in the epoxy at a concentration of about 0.1 mg/ml to about 10 mg/ml, such as about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 2.0 mg/ml, about 3.0 mg/ml, about 4.0 mg/ml, about 5.0 mg/ml, about 6.0 mg/ml, about 7.0 mg/ml, about 8.0 mg/ml, about 9.0 mg/ml, about 10.0 mg/ml.

Addition of the amine-functionalized porphyrin to the epoxy imparts antioxidant properties throughout the epoxy, which can increase the anti-corrosive properties of the epoxy, reduce photo-oxidation of the epoxy, reduce and/or prevent accumulation of biofilm or biofouling on the epoxy. Accordingly, epoxy containing an amine-functionalized porphyrin can be used in place of any other epoxy when anti-oxidative, anti-corrosive, anti-biofouling, and/or increased resistance to photo oxidation is desired, for example in medical or industrial epoxy applications.

In some embodiments, where the epoxy is used to coat the surface of a medical implant, it can reduce or prevent a foreign body response (for example, inflammation) elicited when the implant is implanted into a subject. For example, reactive oxygen species (ROS) and free radicals are often elicited in response to implantation of a medical implant. The anti-oxidative properties of the amine-functionalized porphyrin can reduce accumulation of the ROS and free-radicals, which can reduce any corresponding implantation response, ultimately improving tissue integration of the medical implant.

Further, because the amine-functionalized porphyrin is evenly distributed throughout the epoxy, a scratch or other defect on an epoxy coating will not reduce the anti-oxidative properties of the epoxy so long as the defect does not completely remove or go through the coating.

A non-limiting industrial use includes the coating of metal parts to prevent corrosion (such as oxidative corrosion), for example in a primer for coating metal surfaces before applying paint. Such a primer coating could be used on metal surfaces on an automobile to impart anti-oxidative properties to such surfaces.

Additionally, epoxy coatings are currently used in a variety of marine applications to prevent corrosion (such as oxidative corrosion of metal surfaces) and provide a protective layer. Utilizing an amine-functionalized porphyrin epoxy can prevent or reduce biofouling (preventing or reducing slime/algae build up as well as attachment of muscles and barnacles) on marine surfaces while improving corrosion protection of metal components. Exemplary applications include ship hulls, any component that would be below the waterline (both fresh and salt water vessels), and pipes bringing in water to the vessel for things like sinks, toilets, ballast tanks, and cooling various devices. Other anti-biofouling applications include the exterior of oilrigs, buoys, environmental sensors placed below the water, underwater cameras, piers (either floating or supported by pillars), and underwater power generating devices.

Other more specific biofouling issues that could be reduced or prevented with the amine-functionalized porphyrin epoxy coating include, biofouling of heat exchangers in industries such as power generation. Additionally, adding an amine-functionalized porphyrin epoxy can prevent or reduce biofouling of desalination filters, and because the coating is not designed to leech anything into the water, the water would be safe to move on to the next step of treatment. Both power generation and desalination industries have issues with biofouling inside water transport pipes. This issue can be reduced or prevented by coating the inside of the pipes with an amine-functionalized porphyrin epoxy. Further, biofouling of pipes, filters, and cages/tanks used in aquaculture can be reduced or prevented by coating or manufacturing such materials with the amine-functionalized porphyrin epoxy, without harming the creatures being farmed.

Epoxy coatings are also currently used in the electronic industry as an electrical insulator. By utilizing an amine-functionalized porphyrin epoxy, the life of the protective coating can be extended, and oxidation of underlying metal components can be reduced, which can increase the life of the device.

Epoxy coatings are also used in the food industry to provide wear and corrosion resistance to food shipping and storage containers. Addition of an amine-functionalized porphyrin epoxy to these containers can improve corrosion protection (such as protection against oxidative corrosion of metal surfaces) while affording an equivalent, if not better, level of wear protection.

Epoxy systems are also currently used in the aerospace industry alongside different fibers to make structural components. By utilizing an amine-functionalized porphyrin epoxy in such materials, the mechanical and anti-oxidative properties of these materials can be improved.

Lastly, the beneficial effects listed above may also be applicable to a wide variety of adhesive applications for the above industries as opposed to just coatings.

C. Hydrogel

In several embodiments, the amine-functionalized porphyrin can be included in a hydrogel, for example for use as a gel coating for medical or industrial use. The amine-functionalized porphyrin can be covalently linked to a polymer-based hydrogel (such as a poly(ethylene glycol) (PEG) or poly(dimethylsiloxane) (PDMS) based hydrogel) to impart antioxidant properties to the hydrogel.

The hydrogel typically includes at least four components. First, a polymer backbone (such as branched, 4-arm, 8-arm, or linear polyethylene glycol (PEG) or poly(dimethylsiloxane) (PDMS) end functionalized with acrylate or vinyl sulfone). Second, an amine-functionalized porphyrin (such as iSODm). The primary amines of the amine-functionalized porphyrin included in the hydrogel can be at about a 1:1 ratio to the end functional groups of the polymer backbone. Third, a radical initiator, such as potassium persulfate or ammonium persulfate. The radical initiator can be included in the hydrogel at about less than 1% weight concentration. Fourth, a polymer cross-linker, such as a branched, 4-arm, 8-arm, or linear PEG (homofunctionalized with amines), PDMS (homofunctionalized with amines), or polyethylenimine (PEI) with amines in about a 1:1 ratio to end function groups of the polymer backbone.

The amine-functionalized porphyrin (such as iSODm) can be included in the hydrogel at a concentration appropriate for the intended use of the hydrogel. In some embodiments, the amine-functionalized porphyrin (such as iSODm) can be included in the hydrogel at a concentration of about 0.1 mg/ml to about 10 mg/ml, such as about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 2.0 mg/ml, about 3.0 mg/ml, about 4.0 mg/ml, about 5.0 mg/ml, about 6.0 mg/ml, about 7.0 mg/ml, about 8.0 mg/ml, about 9.0 mg/ml, about 10.0 mg/ml.

In several embodiments, a hydrogel including an amine-functionalized porphyrin can be used for medical applications, such as in a wound sealant (for example, for ocular, neural, or cardiac surgery) or as a bulk material for disposable contact lenses. PEG and silicone based hydrogels have been used as wound sealants for ocular, neural, and cardiac surgery, as well as the bulk material for many disposable contact lenses. As sealants, they have advantages over sutures, staples, and tissue glues in fluid-filled surgical sites, such as the eye, dura mater, and blood vessels, as they form a water-tight seal with the wound margin, and generate minimal leachable byproducts. In some embodiments, the hydrogel can be used in a contact lens. As contact lenses, hydrogels provide excellent optical and mechanical properties, while being porous and wettable, limiting cell adhesion and mechanical irritation. Despite these intrinsic benefits, hydrogel based wound sealants and contact lenses are still subject to a foreign body response consisting of cellular and fibrous encapsulation, which incites reactive oxidative species mediated irritation and inflammation. By incorporating an amine-functionalized porphyrin (such as iSODm) into the polymer matrix of the hydrogel, reactive oxidative species are reduced upon contact, limiting irritation and discomfort to the user.

In additional embodiments, a hydrogel including an amine-functionalized porphyrin (such as iSODm) can be used for industrial applications, such as in an anti-fouling coating for recreational and commercial boats. Current anti-biofouling coatings for recreational and commercial boats rely upon either biocidal leachables from anti-fouling paints or low surface energy, hydrogel coatings that prevent microbes and shellfish from adhering to underwater boat components. By incorporating an anti-fouling compound into the matrix of a low surface energy hydrogel, both chemical and physical anti-fouling mechanism are engaged. Further, the intrinsic corrosion protection capability of an amine-functionalized porphyrin (such as iSODm) reduces oxidation and rusting of boat hulls and parts.

In some embodiments, a method is provided for preventing or reducing formation of a biofilm on a surface (such as a surface on a medical implant or a marine surface), comprising coating the surface with an amount of the hydrogel containing amine-functionalized porphyrin (such as iSODm) that is effective for reducing biofilm formation. In some embodiments, the hydrogel can be coated onto the inside or outside surface of a medical catheter to reduce or prevent biofilm accumulation on the catheter. In some embodiments, the hydrogel can be coated onto the inside or outside surface of a marine surface (such as all or part of the surface of a hull, a pipe, a heat exchanger, or a valve, of a ship) to reduce or prevent biofilm accumulation.

EXAMPLES

The following examples are provided to illustrate particular features of certain embodiments, but the scope of the claims should not be limited to those features exemplified.

Example 1

Immobilizable Superoxide Dismutase Mimic (iSODm) Design and Synthesis

This example illustrates design, production, and characterization of a novel amine-functionalized porphyrin compound termed iSODm. The iSODm compound includes four added primary amine functional groups compared to standard porphyrin compounds, and can be incorporated into materials of interest to impart antioxidant properties to those materials.

FIG. 1A illustrates the structure of the iSODm compound. As shown in FIG. 1, the iSODm includes a porphyrin with alkylation of the 'ortho' position pyridyl. This compound has a three dimensional structure that prevents intercalation with negatively charged biomolecules and subsequent toxicity.

An exemplary protocol for synthesizing the iSODm compound is as follows: The porphyrin, meso-Tetra(2-pyridyl) porphine was dissolved in DMF with excess 2-bromoethylamine (20× by mole) and the temperature is increased to 100° C. overnight. A solution of excess $MnCl_2$ in DMF (20×) was added directly to the reaction, which was kept under reflux for an additional 24 hours. The resulting porphyrin was precipitated by the addition of tetrahydrofuran and washed with diethyl ether. The complex was then purified by first dissolving in water and then crystallized using a saturated ammonium hexaflurophosphate solution. The final water soluble product was prepared by dissolving the hexafluorophosphate salt in acetone and precipitating with tetrabutylammonium chloride salt.

The presence of the primary amine groups on the iSODm compound facilitates conjugation and immobilization of the compound. The iSODm can be used for covalent incorporation into a wide variety of chemistries. Because of the four primary amines on each iSODm compound, iSODm is particularly useful in the preparation of polymers and polymer based coatings, including self-assembled monolayers, epoxy coatings, and hydro-gels.

Figure 1B:
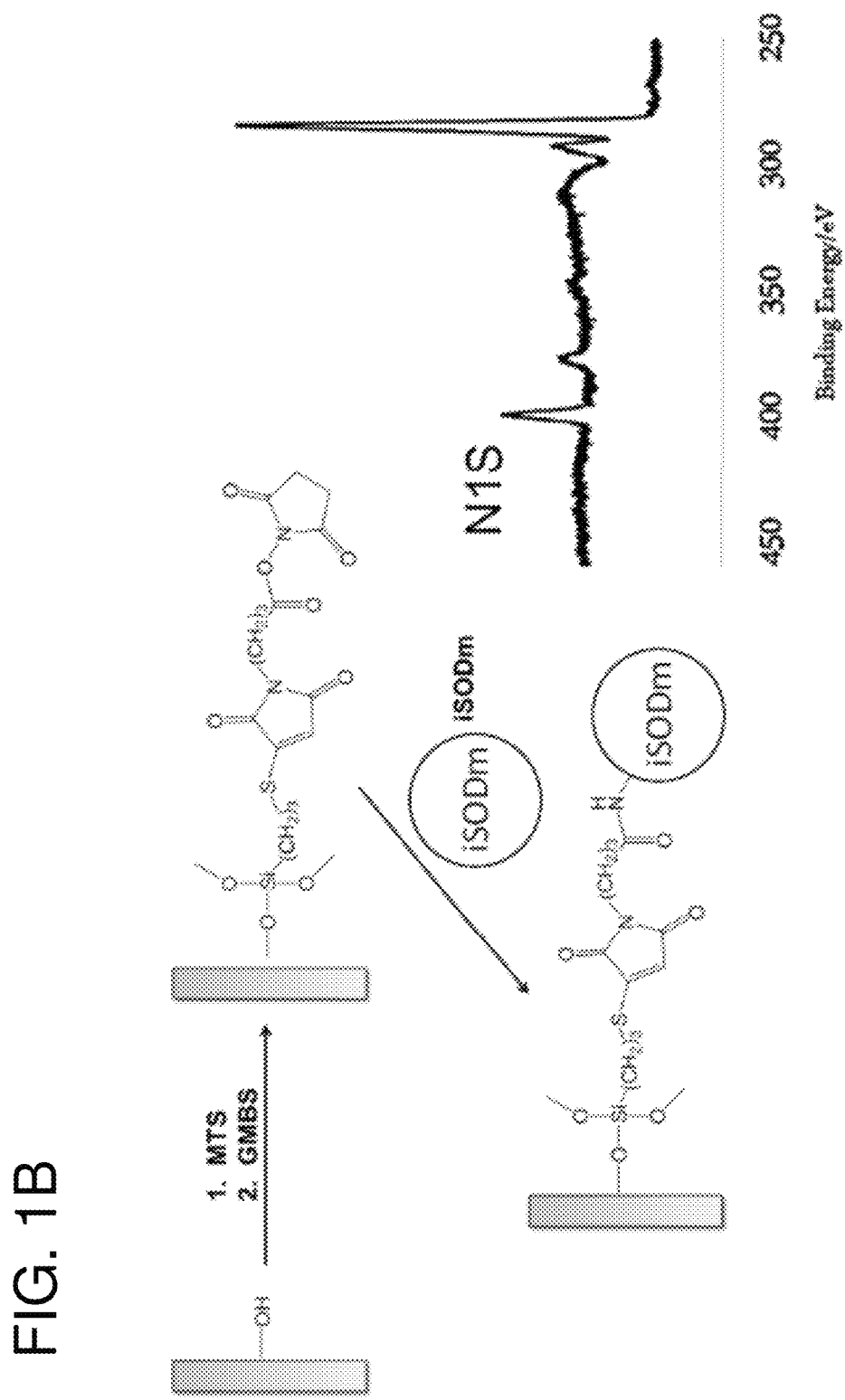
Figure 2:
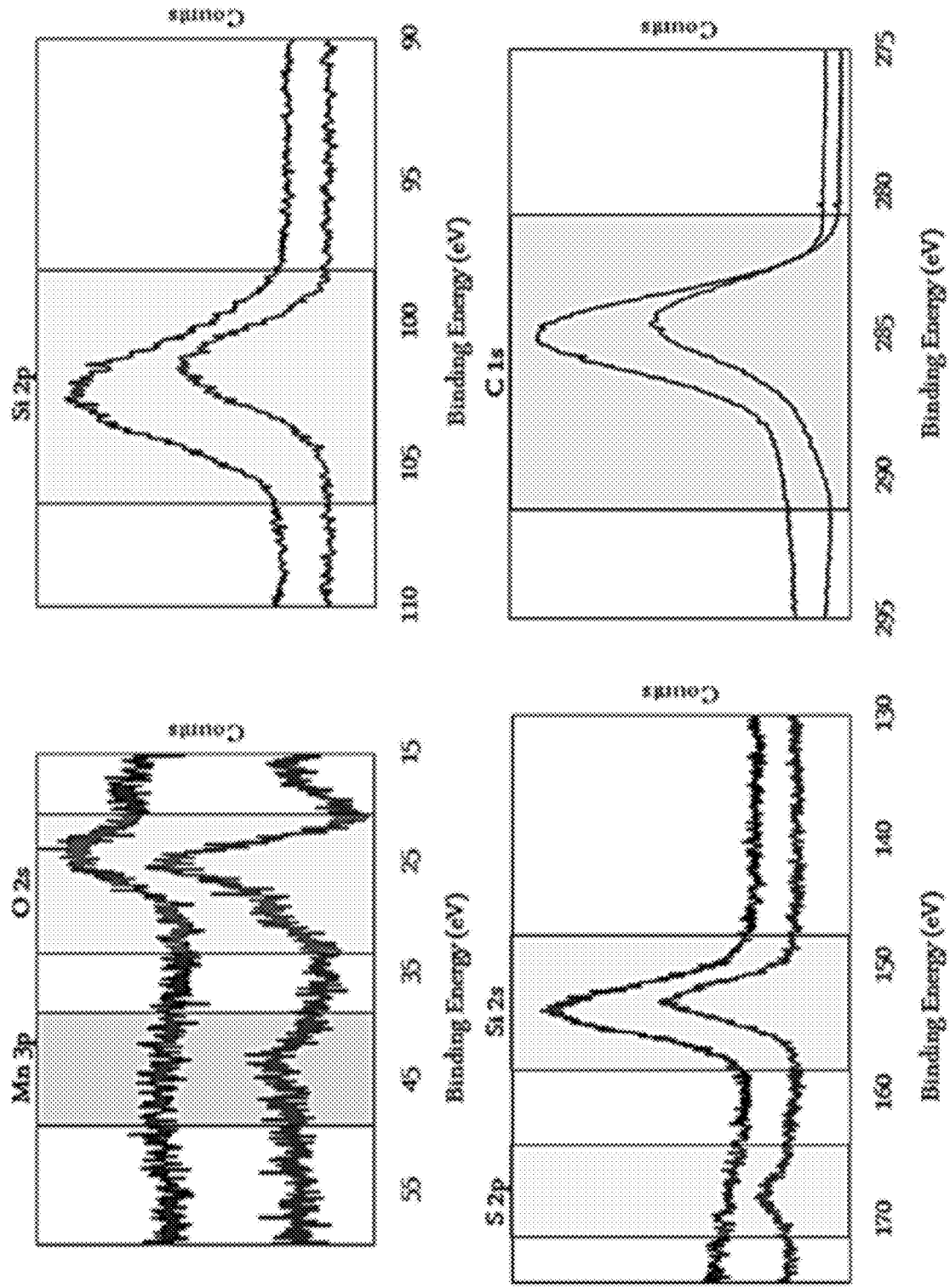
FIG. 2 illustrates results of X-Ray photoelectron spectroscopy (XPS) assays to detect manganese to verify the presence of a coating of iSODm covalently attached to a silica surface.
Figure 3:
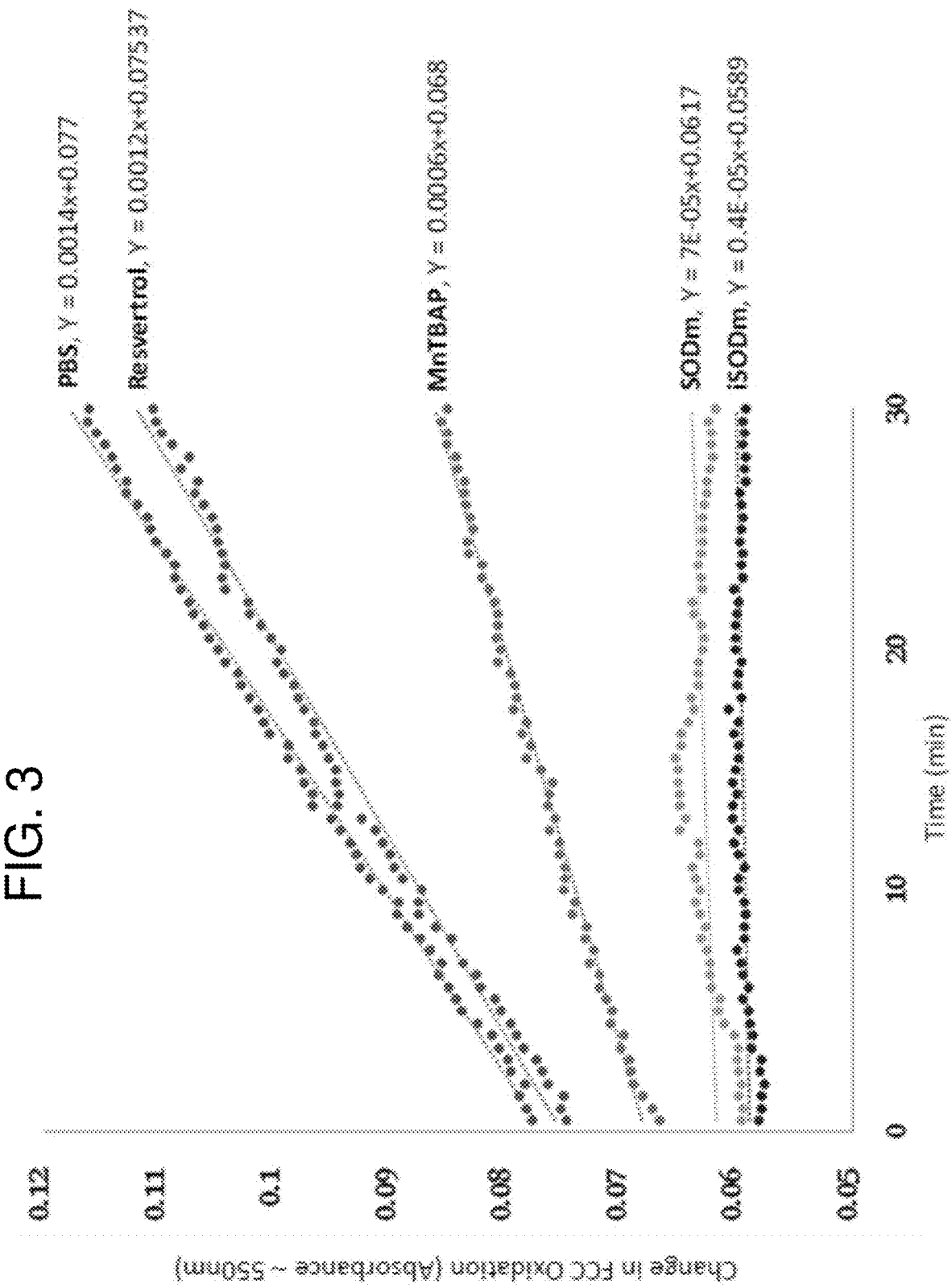
FIG. 3 is a graph illustrating that the iSODm compound effectively catalyzes dismutation of superoxide. Superoxide accumulation by the xanthine oxidase enzyme system in the presence of the indicated antioxidants was measured by the reduction of ferricytochrome C (measured spectrophotometrically at =550 nm). iSODm reduced superoxide accumulation to the same extent as free SODm and greatly outperformed the control antioxidants resveratrol and the anionic porphyrin MnTBAP.
Figure 4:
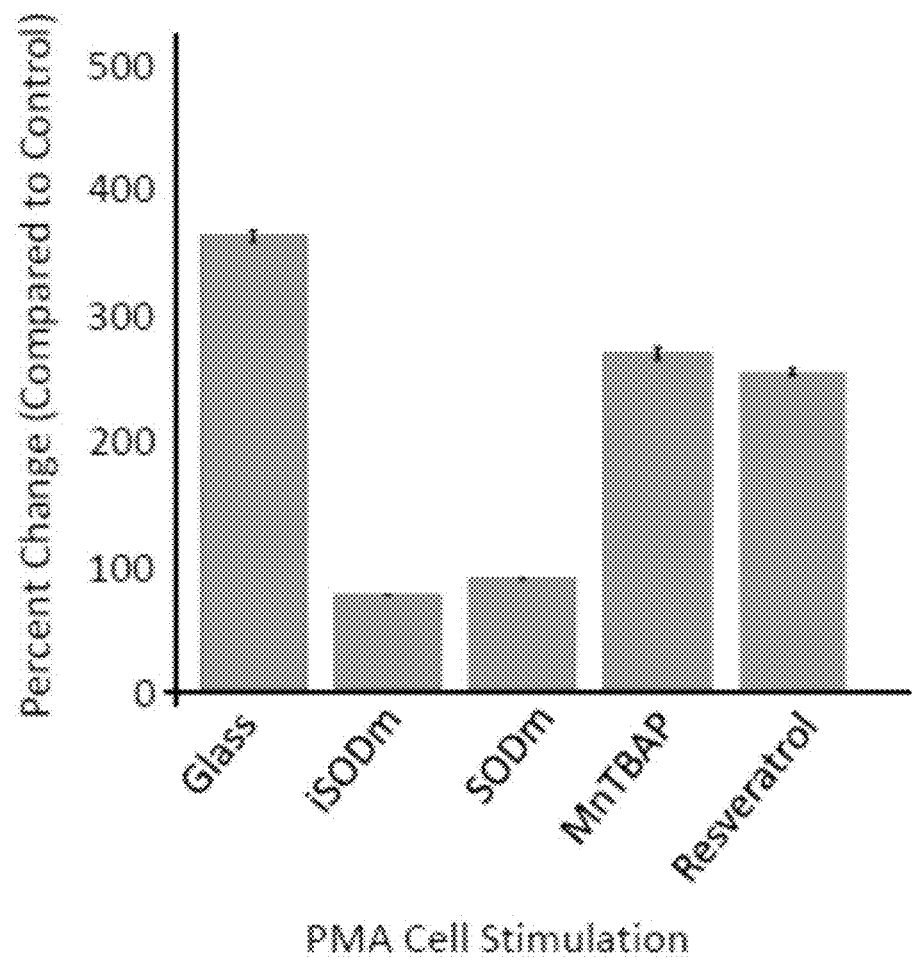
FIG. 4 is a graph illustrating that superoxide production from activated cells can be reduced by iSODm. Macrophage cells were cultured on a glass surface (control), on glass surface coated with iSODm, or in the presence of free SODm, resveratrol, or anionic porphyrin (MnTBAP). Superoxide generated via the stimulation of activated macrophage cells using PMA was measured by the reduction of ferricytochrome C (measured spectrophotometrically at $\lambda$=550 nm). iSODm reduced superoxide production relative to control (glass) and greatly outperformed the antioxidants resveratrol and MnTBAP.
Figure 5:
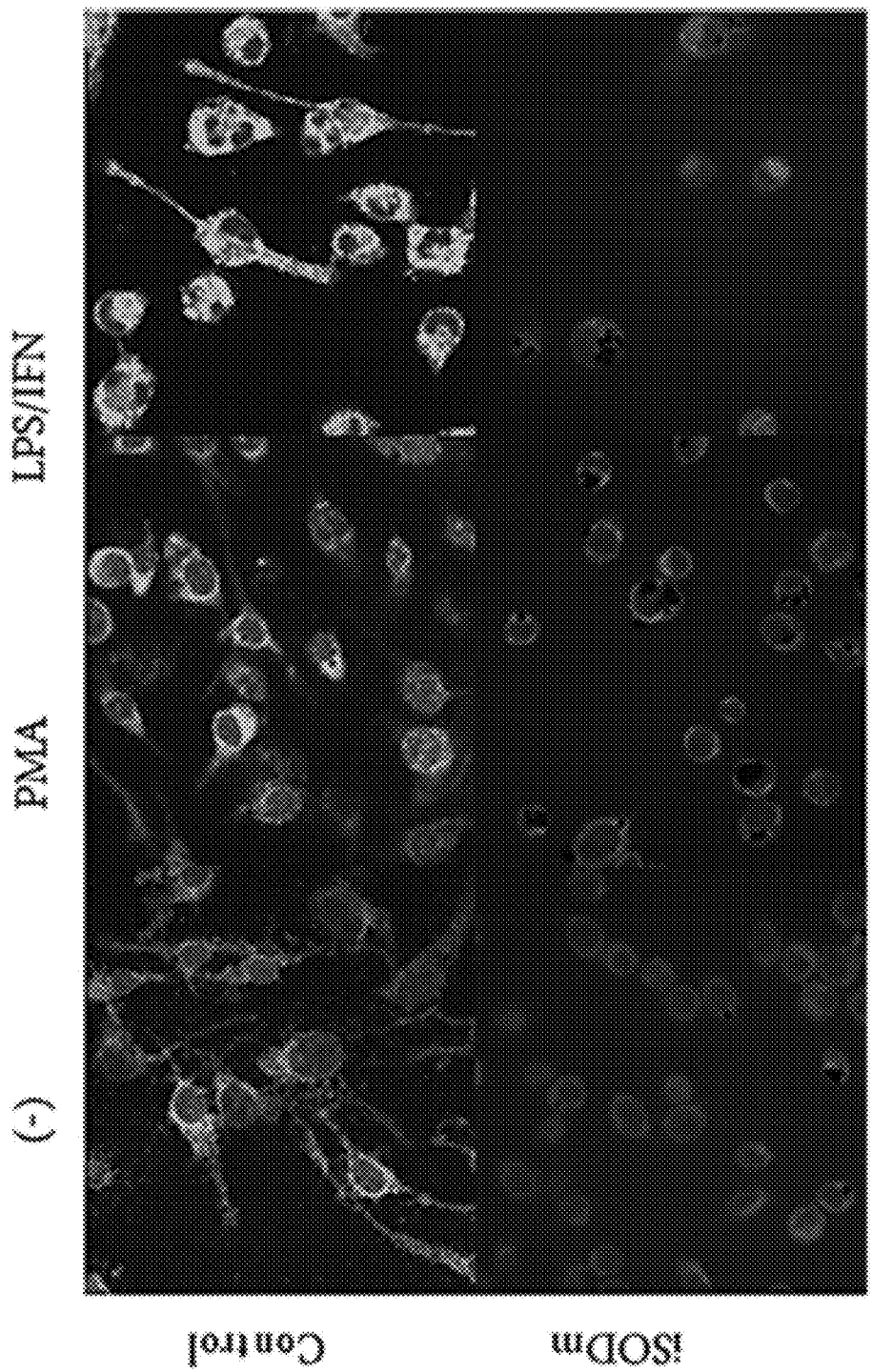
FIG. 5 is digital image illustrating that intracellular reactive oxygen species (ROS) accumulation is reduced in cells cultured on iSODm coated surfaces. An immortalized microglia cell line (Highly Aggressive Proliferating Immortalized cell line, HAPI cells) was grown on a glass surface (control) or an iSODm-coated glass surface. Intracellular oxidation of dihydrorhodamine 123 was assayed to evaluate intracellular ROS levels following stimulation of the HAPI cells by inflammatory agents phorbol myristate acetate PMA or lipopolysaccharide plus interferon-gamma (LPS/IFN).
Figure 6:
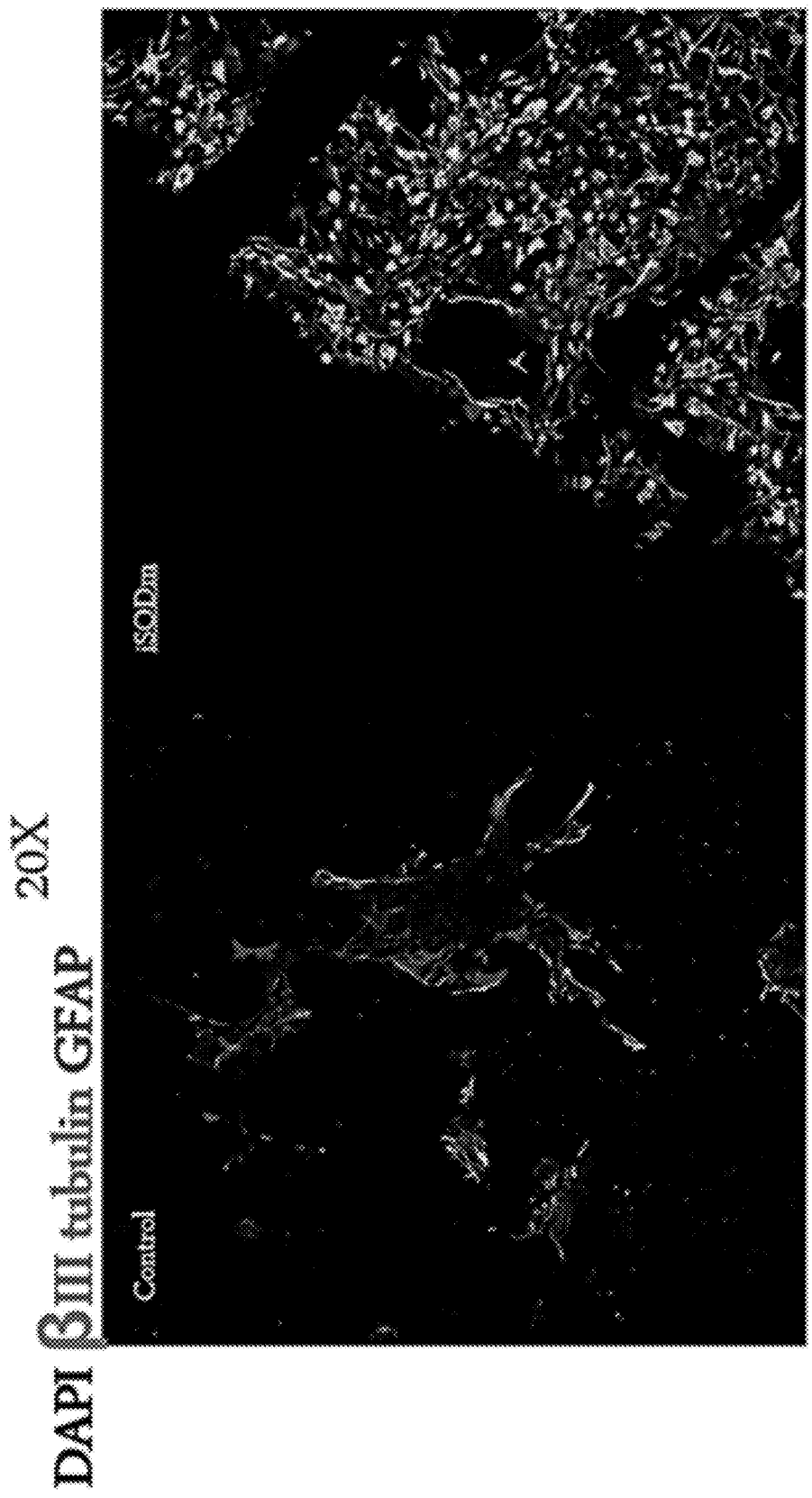
FIG. 6 is a digital image illustrating that attachment and growth of neurons and astrocytes on glass surfaces is increased by an iSODm coating. Primary neural tissue cultures were cultured for 3 days on glass surfaces or glass surfaces coated with iSODm. Surfaces coated with iSODm increased growth of neurons and astrocytes.
Figure 7:
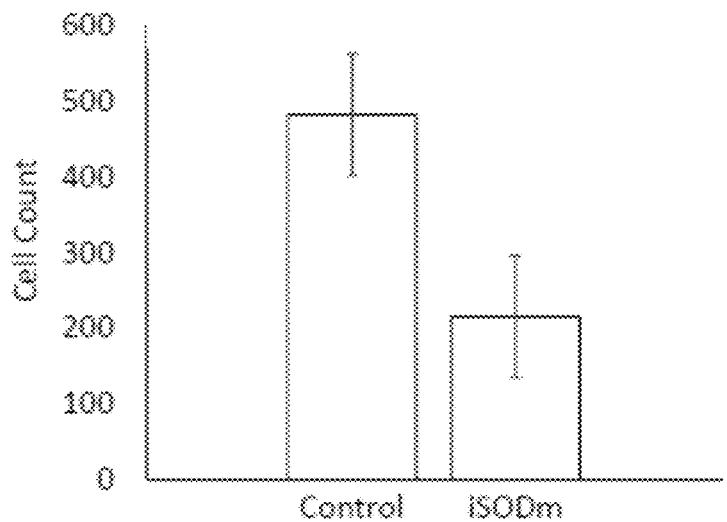
FIG. 7 is a graph illustrating that an iSODm coating reduces attachment of inflammatory cells to a glass surface. HAPI cells were grown on glass surfaces or surfaces coated with iSODm. The iSODm coating significantly reduced the number of adherent HAPI cells.
Figure 8:
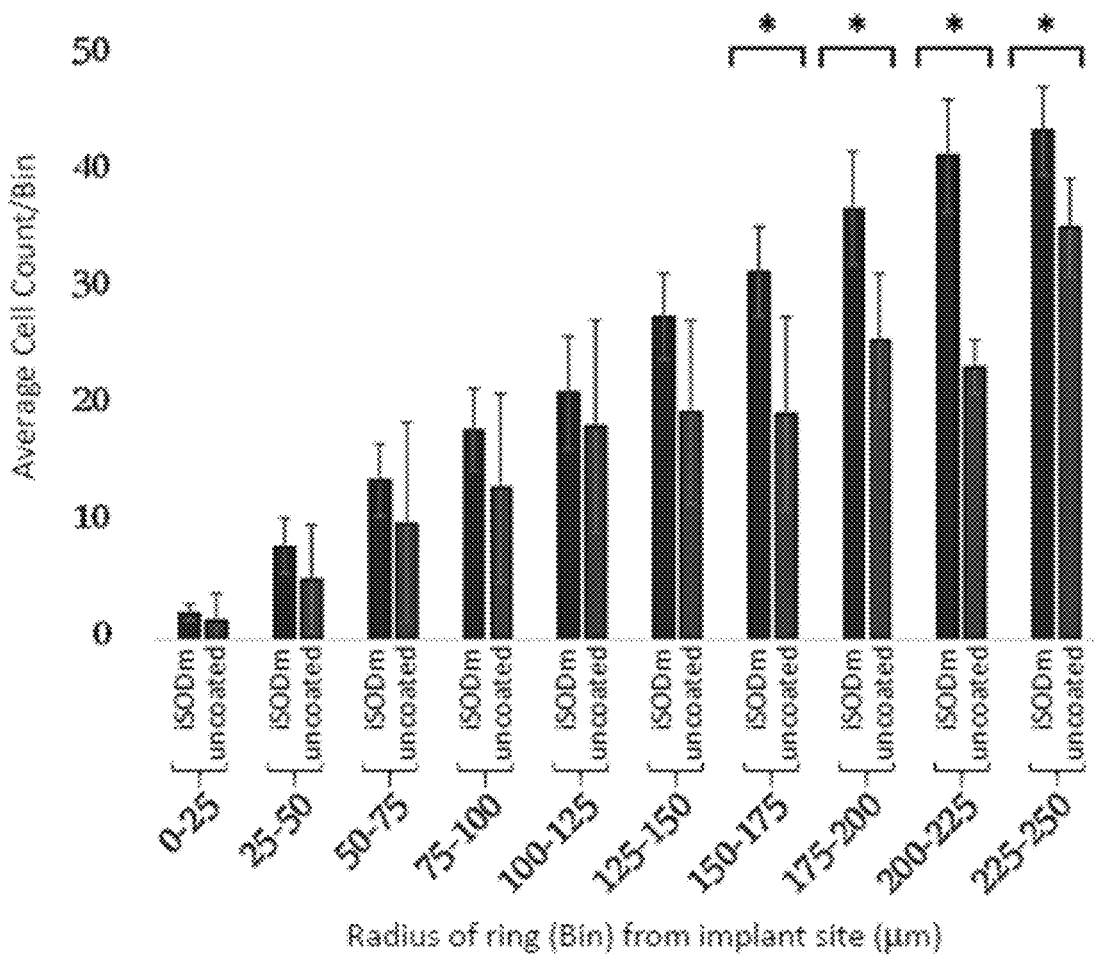
FIG. 8 shows a graph illustrating that an iSODm coating applied to a neural probe increases neural cell density around the probe following chronic implantation in an animal model. Silicon based electrodes coated with iSODm (iSODm) or uncoated control (uncoated) were implanted into rat cortex for one week, after which the surrounding tissue was evaluated for neuron density as indicated by neuron number (NeuN) staining. To evaluate cell density, cells within bins of concentric rings (each of 25 µm thickness) from the implant site were counted. Electrodes with the covalently attached iSODm demonstrated significantly greater neuron density around the probe.
Figure 9A:
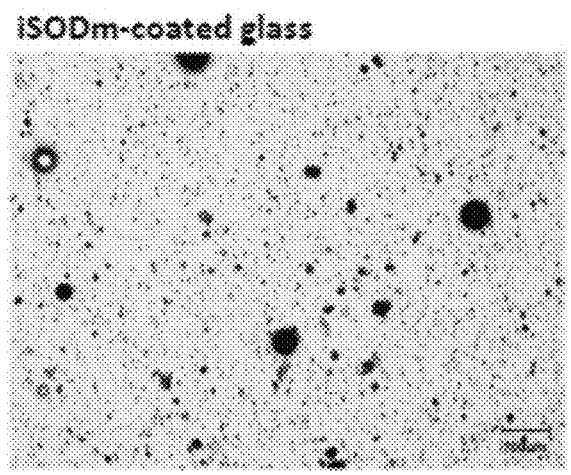
FIGS. 9A-9C are digital images illustrating that an iSODm coating reduces biofouling on a glass surface. Glass coverslips coated with iSODm or uncoated coverslips were submerged in water containing algae and fish waste for one week. Mold hyphae were not observed on the iSODm coated glass (FIG. 9A), but were observed on the control surfaces (FIG. 9C). An interface between the iSODm coating and the glass substrate illustrated the anti-fungal properties of the iSODm coating (FIG. 9B).
Figure 9B:
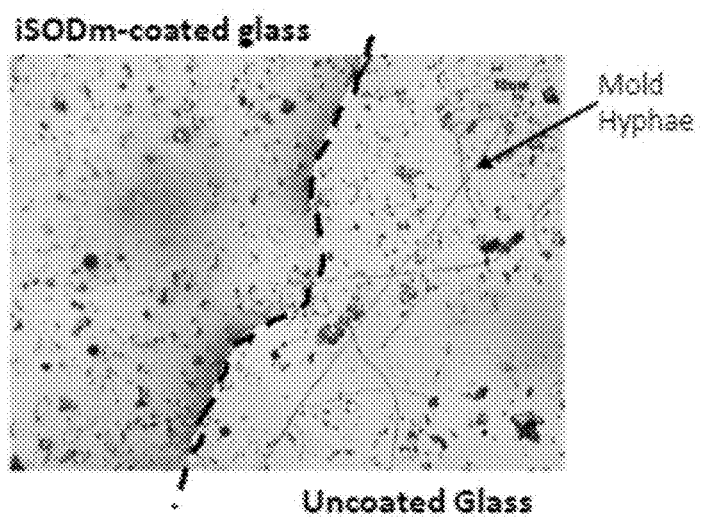
Figure 9C:
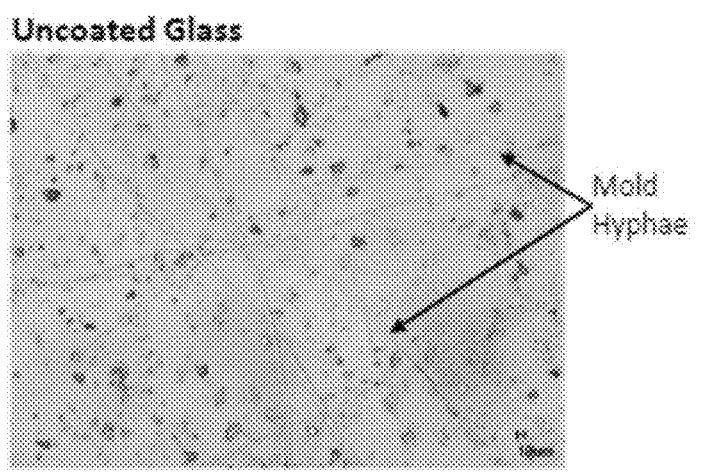
Figure 10:
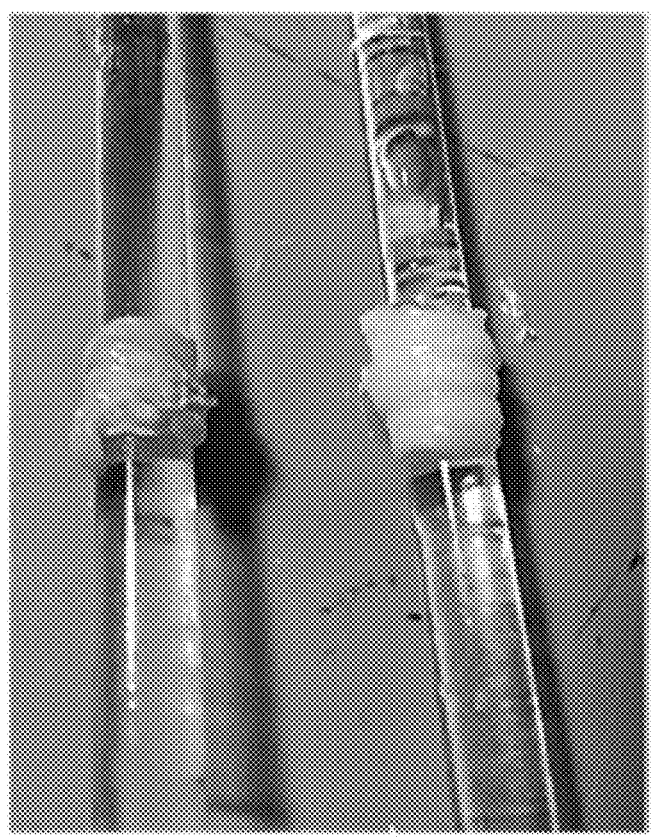
FIG. 10 is a digital image of a nylon polymer including the iSODm compound. iSODm was incorporated into polyamide based polymers to create an antioxidant nylon material. Shown are nylon strands with (left) and without (right) the iSODm.

The primary amine group on the iSODm compound was linked to a silica surface using heterobifunctional crosslinker chemistry to coat the silica surface with the iSODm compound (see FIG. 1B). Briefly, glass substrates to be coated were submerged in a 1:1 MeOH:HCl solution for 30 min. After rinsing with deionized water, concentrated $H_2SO_4$ was pipetted onto glass and allowed to sit for 30 min. All samples were then rinsed with deionized water and dried under $N_2$ flow overnight. The pre-treated samples were then submerged in 2.5% MPTS solution (v/v in toluene) and shaken for two hours inside a glove bag in $N_2$. Afterwards the samples were rinsed with toluene, sonicated for ten minutes, and allowed to dry under $N_2$ flow. The heterobifunctional crosslinker sulfo-GMBS (N-γ-maleimidobutyryl-oxysulfosuccinimide ester) was dissolved in minimal amounts of DMF and diluted to 0.5 mg/mL in absolute ethanol. The silanized surfaces were submerged into the sulfo-GMBS solution for one hour, then rinsed with absolute ethanol and dried. Finally, the iSODm complex was covalently attached to the activated surface by submerging the substrates in 1 mg/mL iSODm solutions (PBS).

Verification that the iSODm coating was present was performed using X-Ray photoelectron spectroscopy (XPS) observation of manganese (FIG. 2).

iSODm effectively catalyzed dismutation of superoxide in a cell free assay. Superoxide accumulation by the xanthine oxidase enzyme system was evaluated in the presence of non-immobilized iSODm, immobilized iSODm, phosphate-buffered saline (negative control), or the known antioxidants resveratrol or anionic porphyrin MnTBAP. Superoxide accumulation was measured by the reduction of ferricytochrome C (measured spectrophotometrically at λ=550 nm). As shown in FIG. 3, iSODm reduced superoxide accumulation to the same extent as free SODm and greatly outperformed the control antioxidants resveratrol and the anionic porphyrin MnTBAP.

Further, iSODm effectively catalyzed dismutation of superoxide in a cell-based assay. Macrophage cells were cultured on a glass surface (control), on glass surface coated with iSODm (iSODm), or in the presence of non-immobilized iSODm (SODm), resveratrol, or anionic porphyrin (MnTBAP). Superoxide generated following the stimulation of activated macrophage cells was measured by the reduction of ferricytochrome C (measured spectrophotometrically at λ=550 nm). As shown in FIG. 4, iSODm reduced superoxide production relative to control (glass) and greatly outperformed the antioxidants resveratrol and MnTBAP.

Intracellular reactive oxygen species (ROS) accumulation is reduced in cells cultured on iSODm coated surfaces. An immortalized microglia cell line (Highly Aggressive Proliferating Immortalized cell line, HAPI cells) was grown on a glass surface (control) or an iSODm-coated glass surface. Intracellular oxidation of dihydrorhodamine 123 was assayed to evaluate intracellular ROS levels following stimulation of the HAPI cells by inflammatory agents phorbol myristate acetate PMA or lipopolysaccharide plus interferon-gamma (LPS/IFN). As shown in FIG. 5, the iSODm coating significantly reduced intracellular ROS.

iSODm Coating Increases Neuron and Astrocyte Attachment

Primary neural tissue cultures were cultured for three days on glass surfaces (control) or glass surfaces coated with iSODm. The iSODm coating increased cellular attachment and growth of both neurons and astrocytes. As shown in FIG. 6, surfaces coated with a 1 mg/ml solution of iSODm showed increased attachment of neurons (green) and astrocytes (red), compared to uncoated surfaces. The density of iSODm on the surface was approximately 10 μg/cm$^2$.

iSODm Coating Decreases Inflammatory Cell Attachment

Additionally, surfaces coated with a 1 mg/ml solution of iSODm showed decreased attachment of inflammatory cells. As shown in FIG. 7, Highly Aggressive Proliferating Immortalized (HAPI) cells showed significantly reduced attachment to glass surfaces coated with iSODm compared to uncoated glass surfaces. The density of iSODm on the surface was approximately 10 μg/cm$^2$.

iSODm Coating Increases Neuron Cell Density Around Implanted Probes

Silicon based electrodes coated with a 1 mg/ml solution of iSODm-coated (iSODm) or uncoated (uncoated) were implanted into rat cortex for one week, after which the surrounding tissue was evaluated for neuron density as indicated by neuron number (NeuN) staining. As shown in FIG. 8, the iSODm coating significantly increased neural cell density around the implanted neural electrodes.

To evaluate cell density, tissue was stained with neuron identifier (NeuN), and cells within bins of concentric rings (each of 25 μm thickness) from the implant site were counted. FIG. 8 shows the cell count for each of these bins. The X axis is the distance from the electrode center (in 25 micron bins) and the Y axis is the cell count within the bins.

The radius of effect was much greater than anticipated. Implant coatings thus far in the literature have had little effect on neuron density, or if effective were limited in range to within 50-100 μM from the coated implant. Thus, it is particularly surprising that the iSODm coated probe can increase neuron density in vivo to greater than 150 μM near an implant which is a much greater effect radius than expected.

Example 2

Amine-Functionalized Metalloporphyrin Coating Reduces Biofouling

This example illustrates that surfaces coated with an amine-functionalized metalloporphyrin have reduced biofouling.

Glass coverslips coated with iSODm as described above or uncoated coverslips were submerged in water containing algae and fish waste for one week. Mold hyphae uniformly adhered to control glass samples following one week submersion (FIG. 9C). In contrast, mold hyphae were not observed on the iSODm coated coverslip (FIG. 9A). An interface between the iSODm coating and the glass substrate illustrated the anti-fungal properties of the iSODm coating (FIG. 9B).

Example 3

Nylon Material Containing an Amine-Functionalized Metalloporphyrin

This example illustrated that an amine-functionalized metalloporphyrin can be incorporated into a nylon material to create an antioxidant nylon material.

The amine-functionalized metallopoprhyrin was readily incorporated into a nylon material using the traditional synthesis for nylon rope. The amine-functionalized metalloporphyrin was dissolved in water and combined with 1,6-diaminohexane in 1:1 ratio. A second solution of sebacoyl chloride was prepared in heptane and gently poured onto the first metalloporphyrin containing solution forming a two layer mixture. Using fine tweezers, nylon rope was pulled from the interface of the two liquids and the fibers were subsequently pulled onto a glass stirring rod. The metallorphyrin containing nylon was noticeably different in color.

Example 4

Epoxy Containing Amine-Functionalized Metalloporphyrin

This example illustrates manufacture and characterization of an epoxy containing an amine-functionalized metalloporphyrin compound.

An epoxy containing iSODm was manufactured. To make the epoxy, dried iSODm was added epoxy resin at 1 mg iSODm/1 ml Epoxy resin. The sample was mixed using a glass stirring rod for five minutes. Primary amines present on iSODm can react with the epoxy resin and begin crosslinking the epoxy groups. To facilitate this, samples were allowed to react at room temperature for 12 hours. Following this reaction, the commercial curing agent was added at 170 µl curing agent/ml epoxy resin/iSODm mixture according to package instructions and stirred for 5 minutes.

Figure 12:
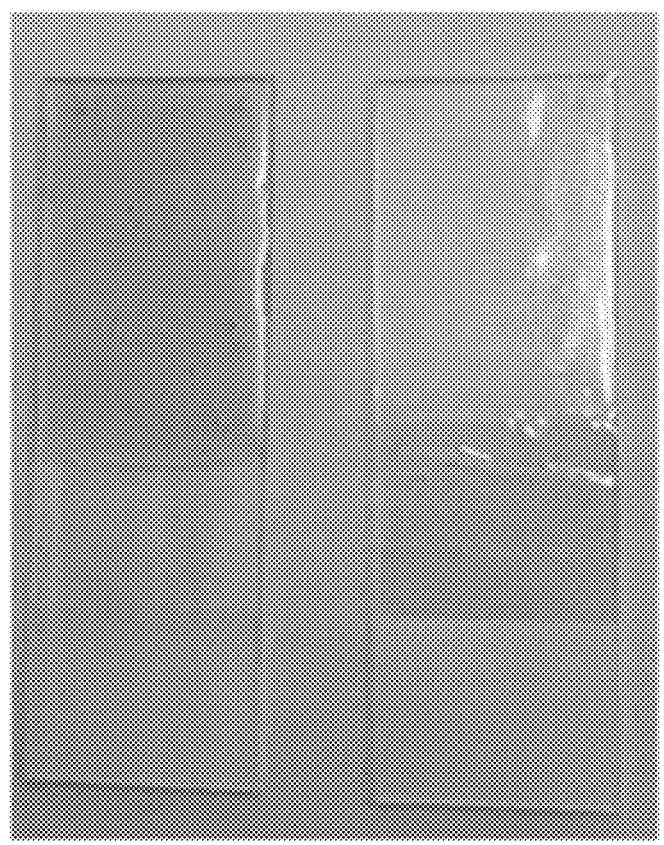
FIG. 12 is a digital image of an epoxy-based resin including the iSODm compound. Glass slides were coated with an epoxy containing iSODm (left) or control epoxy lacking the iSODm (right).

Following addition of the curing agent, the epoxy coating was manually painted on glass microscope slides (FIG. 12). Samples were then cured under two conditions. Slides were placed in an oven at 90° C. and cured for 2 hours or allowed to cure at room temperature for 8 hours.

The benefits of including the iSODm compound in the epoxy include (but are not limited to):
1) Improve curing time: By adding the iSODm with four primary amines that can react with the epoxide groups the curing time is decreased compared to epoxy polymers formed with curing agents having only two amine reactive groups.
2) Improved mechanical properties: The ability of the iSODm to react with 4 different epoxy groups increases the amount of crosslinking in the epoxy polymer, thereby improving the mechanical properties, such as stiffness.
3) Antioxidant properties: Addition of the iSODm to the epoxy imparts antioxidant properties throughout the epoxy. This adds at least the following features to the epoxy that would not be present without the iSODm:
   First, the epoxy coating can better prevent corrosion by reacting with the reactive oxygen that can contribute to corrosion of metal components the coating is placed on.
   Second, photo-oxidation of epoxies can result in color change as well as decreased mechanical properties. The iSODm's antioxidant properties can decrease the deleterious effects of light exposure on the epoxy.
   Third, the addition of iSODm to the epoxy can reduce and/or prevent biofouling. Biofouling occurs on many levels, micro-biofouling from microorganisms (such as bacteria and algae), and macrofouling from mussels and barnacles. By adding the antioxidant properties of the iSODm to the epoxy it is possible to reduce biofouling on multiple levels and in a way that is not detrimental to the organism.
   Fourth, adding the iSODm to the epoxy allows the coating to mitigate the foreign body response elicited by the body when a device or object is surgically implanted. Reactive oxygen and free radicals are common components used by the body's immune system to degrade away any foreign body. These chemicals however also make the environment surrounding the device uninhabitable for cells. This is problematic if you want a device to be chronically present. By mitigating these harmful chemicals the iSODm can make the area around the implant much more hospitable to surrounding tissue cells improving the tissue interaction with the device and ultimately the success of the implanted device.
4) Not just a surface coating: The iSODm compound is uniformly distributed throughout the epoxy polymer. Therefore, no difference in performance is observed in the event of a scratch or chip that does not go completely through the epoxy coating. The beneficial effects of including the iSODm compound in the epoxy polymer cannot be removed in the case of partial removal of the epoxy polymer.

To assay the anti-fouling properties of the iSODm epoxy, coated microscope slides were tested for zebra mussel attachment and algae accumulation (FIG. 14). Zebra mussels were placed on microscope slides coated with a marine epoxy coating (Interlux® InterProtect two part self-priming epoxy barrier coating, "IL" FIG. 14A) or the same coating with 1% w/v iSODm additive (mixed in to the epoxy as described above, "H" in FIG. 14A) and were incubated in a freshwater tank. After 24 hours, the zebra mussels remained attached to the IL-coated slides, but not the H coated-slides (FIG. 14A). Additionally, when the coated microscope slides were placed in a freshwater tank populated with zebra mussels and algae, algae was allowed to accumulate over time (one month), slides coated with epoxy containing iSODm accumulated substantially less algae growth than the slides coated with epoxy lacking iSODm (FIG. 14B).

To assay the anti-corrosive properties of the iSODm epoxy, 3D printed samples of stainless steel and bronze were coated with epoxy Araldite® 506 using Ethyleneamine curing agent or the epoxy resin and curing agent with the addition of 1% w/v iSODm (the iSODm was mixed into the epoxy as described above). Samples that were untreated, coated with epoxy lacking iSODm, or epoxy with iSODm, were subjected to corrosion testing in an ASTM B117 corrosion test chamber. After 250 hours and 750 hours accelerated corrosion in the test chamber, the resolution of text and images on the samples was substantially more clear on the epoxy/iSODm-coated samples than uncoated samples or samples coated with epoxy alone. Therefore, the epoxy coating containing iSODm can inhibit corrosion of metal.

Example 5

Hydrogel with Amine-Functionalized Metalloporphyrin

This example illustrates rapid, in situ curing, poly(ethylene glycol) (PEG)- and poly(dimethylsiloxane) (PDMS)-based hydrogels with iSODm covalently grafted into the polymer matrix to provide anti-inflammatory and anti-biofouling support for medical implants and marine surfaces (such as boat hulls and parts).

The hydrogel includes four components:
1) Polymer backbone: Branched, 4-arm, 8-arm, or linear polyethylene glycol (PEG) or poly(dimethylsiloxane) (PDMS) end functionalized with acrylate or vinyl sulfone
2) iSODm, with iSODm primary amines in a 1:1 ratio to end functional groups of the polymer backbone
3) Radical initiator, such as potassium persulfate or ammonium persulfate at <1% weight concentration 4) Polymer crosslinker: branched, 4-arm, 8-arm, or linear PEG (homofunctionalized with amines), PDMS (homofunctionalized with amines), or polyethylenimine (PEI) with amines in a 1:1 ratio to end function groups of the polymer backbone.

Figure 11:
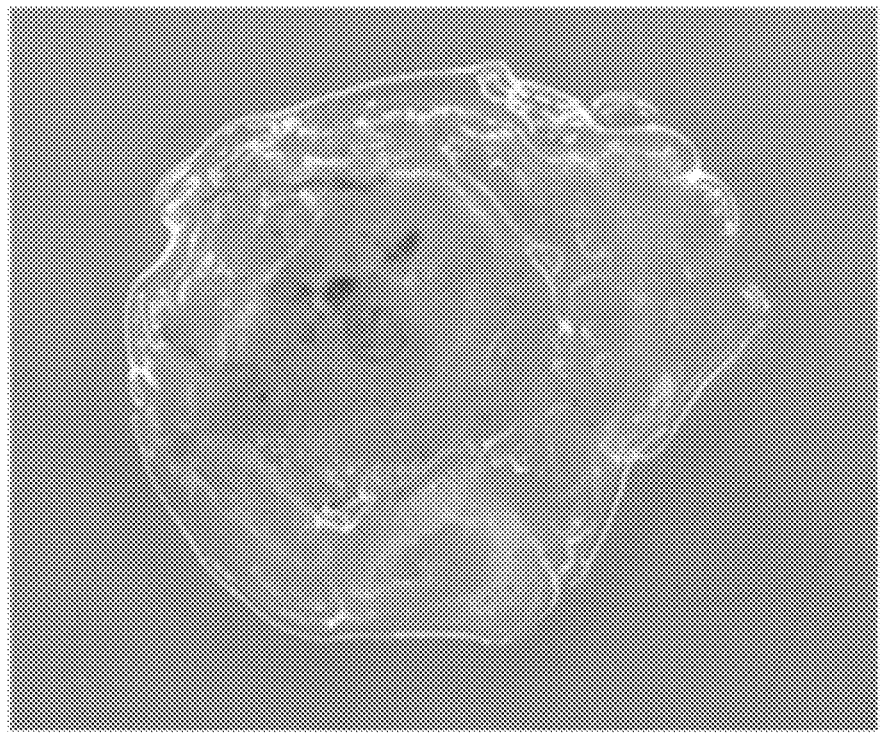
FIG. 11 is a digital image of a hydrogel including the iSODm compound. A hydrogel was formulated PEG-vinyl sulfone initiated with potassium persulfate and mixed with the iSODm compound to create an antioxidant hydrogel.

Components 1-3 are mixed and allowed to sit for 1 hour. During this time, amines of the iSODm will graft onto the vinyl groups of the polymer back bone (without adding Component 4, the solution will form a gel within 18 hours). After adding Component 4, gelation will occur within 1 minute. The hydrogel was allowed to sit for an hour to fully cure (see FIG. 11)

Example 6

Additional Amine Functionalized Porphyrin Compounds

This example illustrates production of additional amine-functionalized compounds based on Heme- and Chlorophyll-type porphyrins. Briefly, native heme and/or chlorophyll compounds can be modified to include primary amine groups as described above for iSODm.

The native Heme and chlorophyll structures include functional groups (such as terminal alkene sites) that can be modified to carboxylic acid functional groups via $KMnO_4$ oxidation under acidic conditions. The vinyl porphyrin molecules can be dissolved in a mixture of methylene chloride, acetic acid, and water (5:1:4 v/v/v). Following the addition of a phase transfer agent (e.g., dimethyl polyethylene glycol) the solution can be cooled using an ice bath. Four molar equivalents of potassium permanganate can be added over the period of 1 hour, and the reaction stirred for 6 hours, while maintaining a cooled ice bath. Excess oxidant can be removed with sodium bisulfite and the reaction acidified with concentrated HCl.

Esterification of carboxylic acid groups and transesterification of ester groups on the porphyrins can be carried out under a single step Fischer esterification process. In brief, the porphyrin can be reacted with molar excess ROH (~20×) where R=N-heterocylic aromatic ring. The reactions can be kept under reflux conditions in the presence of catalytic amount of sulfuric acid for 8-24 hours until the reaction is completed.

The aminoalkyl/aminoaryl substitution of the N-heterocyclic ring, as well as the metalation or transmetallation of the porphyrin complexes is as described for the functionalization of the iSODm.

It will be apparent that the precise details of the methods or compositions described may be varied or modified without departing from the spirit of the described embodiments. We claim all such modifications and variations that fall within the scope and spirit of the claims below.

We claim:

1. A method of reducing formation of a biofilm on a surface, reducing biofouling of a surface, and/or reducing corrosion of a metal surface, comprising coating the surface with an effective amount of a compound comprising the structure set forth as Structure 3:

Structure 3

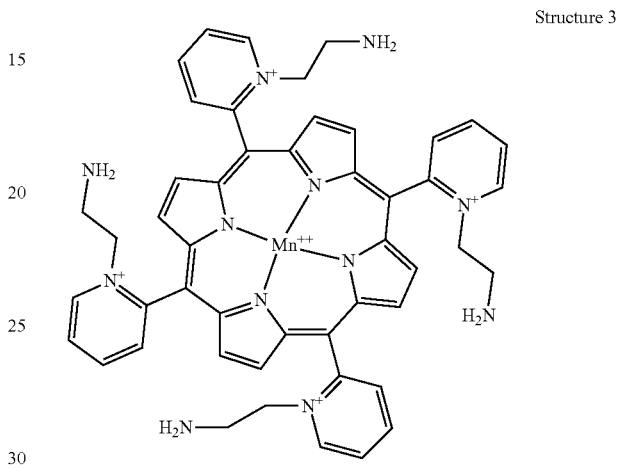

2. The method of claim 1, wherein the surface is a medical implant surface for contacting a tissue in a subject or a marine surface.

3. The method of claim 2, wherein the medical implant surface for contacting a tissue in a subject comprises the exterior surface of a medical catheter.

4. The method of claim 2, wherein the marine surface comprises all or part of the surface of a hull, a pipe, a heat exchanger, or a valve, of a ship.

5. The method of claim 1, wherein the coating comprises from about 0.1 mg/ml to about 10 mg/ml of the compound.

6. The method of claim 1, wherein the surface is coated with an epoxy containing the compound.

7. The method of claim 1, wherein the surface is coated with a hydrogel containing the compound.

* * * * *